| United States Patent [19] | [11] | 4,225,508 |
| Sih | [45] | Sep. 30, 1980 |

[54] 19-HYDROXY-PGI$_2$ COMPOUNDS

[75] Inventor: John C. Sih, Kalamazoo, Mich.

[73] Assignee: The Upjohn Company, Kalamazoo, Mich.

[21] Appl. No.: 54,811

[22] Filed: Jul. 5, 1979

[51] Int. Cl.$^2$ .......................................... C07D 307/93
[52] U.S. Cl. ............................. 260/346.22; 260/345.2; 260/346.73; 260/556 A; 260/556 AR; 260/570.5 CA; 260/573; 260/574; 260/577; 260/584 R; 260/584 A; 542/421; 542/422; 542/426; 548/250; 560/121; 560/504; 568/838; 568/374; 568/373; 568/445; 542/416; 542/431
[58] Field of Search ...................... 260/346.22, 346.73; 542/416, 420, 422, 426, 431

[56] References Cited

PUBLICATIONS

Johnson et al., Prostaglandins 12, 915–928, (1978).

*Primary Examiner*—Henry R. Jiles
*Assistant Examiner*—Bernard Dentz
*Attorney, Agent, or Firm*—Robert A. Armitage; Morris L. Nielsen

[57] ABSTRACT

Prostacyclin and prostacyclin-type derivatives having a 19-hydroxy feature are disclosed, including processes for preparing them and the appropriate intermediates. The compounds are useful for pharmacological purposes such as inhibition of blood platelate aggregation.

12 Claims, No Drawings

19-HYDROXY-PGI$_2$ COMPOUNDS

BACKGROUND OF THE INVENTION

This invention relates to prostacyclin derivatives and to processes for preparing them.

The prostacyclins are a group of organic compounds, including for example prostacyclin itself, also named as prostaglandin I$_2$(PGI$_2$), represented by formula 1. Prostacyclin is (5Z)-9-deoxy-6,9α-epoxy-Δ5-PGF$_{1α}$ (using prostaglandin nomenclature) or (5Z, 9α, 11α, 13E, 15S)-6,9-epoxy-11,15-dihydroxyprosta-5,13-dien-1-oic acid. The atom numbering of the carbon skeleton is shown in that formula. Also defined by this structure are the absolute configurations (5Z, 8R, 9S, 11R, 12R, 13E, and 15S) for the potentially isomeric centers of this molecule.

For background on prostacyclin, see for example R. A. Johnson et al., Prostaglandins 12, 915–928 (1976) and R. A. Johnson et al., J. Am. Chem. Soc. 100, 7690–7704 (1978), and, as to pharmacological activity, the references cited therein. For analogs of prostacyclin, see, for example, J. Fried et al., Proc. Natl. Acad. Sci. U.S.A. 74, 2199–2203, K. C. Nicolaou et al., J.C.S. Chem. Comm. 1977, 331–332, N. A. Nelson, J. Am. Chem. Soc. 99, 7362–7363 (1977), and K. Kojima et al., Tetra. Letters, 1978, 3743–3746. Regarding the nomenclature for analogs of PGI$_2$, see R. A. Johnson et al., Prostaglandins 15, 737–740 (1978).

Prostacyclins are related to prostaglandins which are in turn related to prostanoic acid which has the structure and atom numbering of formula 2. There is extensive literature on prostaglandins, but for background see for example Bergstrom et al., Pharmacol. Rev. 20, 1 (1968). PGF$_{2α}$ is represented by formula 3.

As drawn herein the formulas represent a specific optically active isomer having the same absolute configuration as PGE$_1$ obtained from mammalian tissues.

In the formulas, broken line attachments to the cyclopentane ring or side chain indicate substituents in alpha configuration, i.e. below the plane of the ring or side chain. Heavy solid line attachments indicate substituents in beta configuration, i.e. above the plane. With respect to "R" and "S" usage, see R. S. Cahn, J. Chem. Ed. 41, 116 (1964). As to "Z" and "E" nomenclature for stereoisomerism about a double bond see J. E. Blackwood et al., J. Am. Chem. Soc. 90, 509 (1968).

SUMMARY OF THE INVENTION

It is the purpose of this invention to provide novel products having pharmacological activity. It is a further purpose to provide a process for preparing these products and their intermediates. More specifically, there are provided various prostacyclin derivatives having a 19-hydroxy or 19-hydroxy-19-methyl feature.

Accordingly there are provided 19-hydroxy compounds of formula 4, wherein 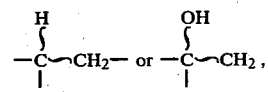 is a radical represented by loss of C$_{19}$ and C$_{20}$ from a prostacyclin-type compound of one of the following groups comprising respectively (I) compounds of formula 5
(II) compounds of formula 6
(III) compounds of formula 7
(IV) compounds of formula 8
(V) compounds of formula 9
(VI) compounds of formula 10
(VII) compounds of formula 11
(VIII) compounds of formula 12
(IX) compounds of formula 13
(X) compounds of formula 14

For formulas 5–14 the terms A$_1$, E$_1$, L$_1$, M$_1$, and the like are defined in the TABLE of Definition of Terms for Formulas herein, together with other terms used hereinafter.

TABLE

Definition of Terms for Formulas

A$_1$ is oxa (—O—).
A$_2$ is —CH$_2$O—.
Ac is acetyl (CH$_3$C(O)—).
E$_1$ is methylene (—CH$_2$—).
E$_2$ is ethylene (—CH$_2$CH$_2$—).
G is nitrato, iodo, chloro, bromo, acetato, trifluoroacetato, or benzoato.
Hal is chloro, bromo, or iodo.
L$_1$ is
 (1) —(CH$_2$)$_n$— wherein n is one to 5, inclusive, or
 (2) —(CH$_2$)$_p$—CF$_2$— wherein p is 2, 3, or 4, with the proviso that, when M$_1$ is $$-\overset{H}{\underset{|}{C}}\frown CH_2- \text{ or } -\overset{OH}{\underset{|}{C}}\frown CH_2,$$

L$_1$ also includes —CH$_2$—CH=CH—.
L$_2$ is
 (1) —(CH$_2$)$_j$— wherein j is one to 4, inclusive,
 (2) —(CH$_2$)$_q$—CF$_2$— wherein q is one, 2, or 3, or
 (3) —CH=CH—.
L$_3$ is
 (1) —(CH$_2$)$_n$— wherein n is one to 5, inclusive,
 (2) —(CH$_2$)$_p$—CF$_2$— wherein p is 2, 3, or 4, or
 (3) —CH$_2$—CH=CH—.
L$_4$ is
 (1) —(CH$_2$)$_n$— wherein n is one to 5, inclusive, or
 (2) —(CH$_2$)$_p$—CF$_2$— wherein p is 2, 3, or 4.
L$_5$ is
 (1) —(CH$_2$)$_p$— wherein p is 2, 3, or 4, or
 (2) —CH$_2$—CF$_2$—
L$_6$ is
 (1) —(CH$_2$)$_n$— wherein n is one to 5, or
 (2) —CH$_2$CH=CH—.
L$_7$ is
 (1) —(CH$_2$)$_j$— wherein j is one to 4, inclusive, or
 (2) —(CH$_2$)$_q$—CF$_2$— wherein q is one, 2, or 3.
M$_1$ is

 (1)

 (2)

 (3)

 (4)

with bonds to $A_1$ and L as shown, and wherein ~ indicates attachment in alpha or beta configuration.

$M_2$ is

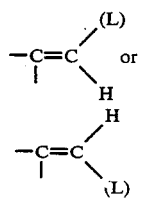

with bonds to L as shown.

Ms is mesyl ($CH_3—SO_2—$).

Q is

wherein $R_4$ is hydrogen or alkyl of one to 4 carbon atoms, inclusive.

$Q_1$ is

wherein $R_4$ is hydrogen or alkyl of one to 4 carbon atoms, inclusive, and wherein $R_{25}$ is a blocking group as defined below.

$Q_2$ is

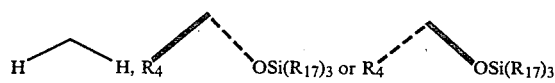

wherein $R_4$ is hydrogen or alkyl of one to 4 carbon atoms, inclusive, and $R_{17}$ is alkyl of one to 4 carbon atoms, inclusive, phenyl, phenyl substituted with one to 2 fluoro, chloro, or alkyl of one to 4 carbon atoms, inclusive, or aralkyl of 7 to 12 carbon atoms, inclusive, the $R_{17}$ groups being the same or different.

$Q_3$ is

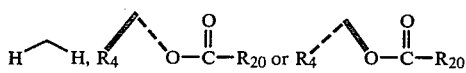

wherein $R_{20}$ is alkyl of one to 7 carbon atoms, inclusive.

$Q_4$ is

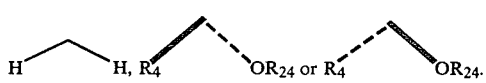

wherein $R_{24}$ is carboxyacyl as defined below.

$Q_5$ is

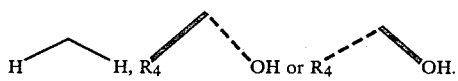

$R_1$ is
(1) —$COOR_3$
(2) —$CH_2OH$
(3) —$CH_2N(R_7)(R_8)$

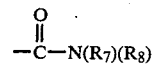

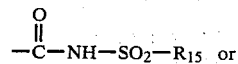

wherein $R_3$ is (a) hydrogen, (b) alkyl of one to 12 carbon atoms, inclusive, (c) cycloalkyl of 3 to 10 carbon atoms, inclusive, (d) aralkyl of 7 to 12 carbon atoms, inclusive, (e) phenyl, (f) phenyl substituted with one, 2, or 3 chloro or alkyl groups of one to 3 carbon atoms, inclusive:

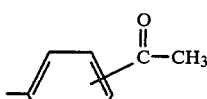

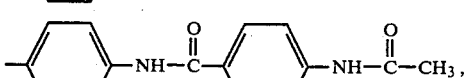

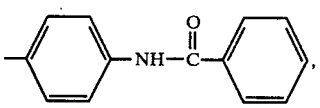

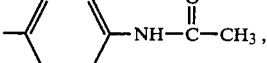

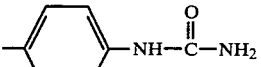

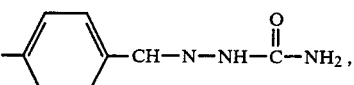

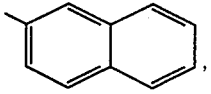

wherein $R_{16}$ is phenyl, p-bromophenyl, p-biphenylyl, p-nitrophenyl, p-benzamidophenyl, or 2-naphthyl, or (o) a pharmacologically acceptable cation; wherein $R_7$ and $R_8$ are hydrogen, alkyl of one to 12 carbon atoms, inclusive, benzyl, or phenyl, being the same or different, and wherein $R_{15}$ is hydrogen, alkyl of one to 12 carbon atoms, inclusive, phenyl, phenyl substituted with one, 2, or 3 chloro or alkyl groups of one to 3 carbon atoms, inclusive, or phenyl substituted with hydroxycarbonyl or alkoxycarbonyl of one to 4 carbon atoms, inclusive, $R_2$ is hydrogen, hydroxyl, or hydroxymethyl $R_3$ is as defined above for $R_1$ $R_4$ is hydrogen or alkyl of one to 4 carbon atoms, inclusive.

$R_5$ and $R_6$ are hydrogen, alkyl of one to 4 carbon atoms, inclusive, or fluoro, being the same or different, with the proviso that one of $R_5$ and $R_6$ is fluoro only when the other is hydrogen or fluoro.

$R_7$ and $R_8$ are hydrogen, alkyl of one to 12 carbon atoms, inclusive, benzyl, or phenyl, being the same or different, and wherein $R_{15}$ is hydrogen, alkyl of one to 12 carbon atoms, inclusive, phenyl, phenyl substituted with one, 2, or 3 chloro or alkyl groups of one to 3 carbon atoms, inclusive, or phenyl substituted with hydroxycarbonyl or alkoxycarbonyl of one to 4 carbon atoms, inclusive.

$R_9$ is hydrogen or hydroxyl.

$R_{10}$ is straight-chain alkyl of one to 6 carbon atoms, inclusive.

$R_{11}$ is hydrogen, $-OR_{25}$ or $-CH_2OR_{25}$ wherein $R_{25}$ is a blocking group, as defined below.

$R_{12}$ is chloro, bromo, or iodo.

$R_{13}$ is hydrogen or methyl.

$R_{14}$ is hydrogen, $-O-Si(R_{17})_3$, or $-CH_2OSi(R_{17})_3$ wherein $R_{17}$ is as defined below.

$R_{15}$ is hydrogen, alkyl of one to 12 carbon atoms, inclusive, aralkyl of 7 to 12 carbon atoms, inclusive, phenyl, phenyl substituted with one, 2, or 3 chloro or alkyl groups of one to 3 carbon atoms, inclusive, or phenyl substituted with hydroxycarbonyl or alkoxycarbonyl in which the alkoxy group consists of one to 4 carbon atoms, inclusive.

$R_{16}$ is phenyl, p-bromophenyl, p-biphenylyl, p-nitrophenyl, p-benzamidophenyl, or 2-naphthyl.

$R_{17}$ is alkyl of one to 4 carbon atoms, inclusive, phenyl, phenyl substituted with one to 2 fluoro, chloro, or alkyl of one to 4 carbon atoms, inclusive, or aralkyl of 7 to 12 carbon atoms, inclusive, the $R_{17}$ groups being the same or different.

$R_{18}$ is the same as $R_1$ but excluding $-COOH$ $R_{19}$ is hydrogen,

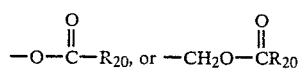

wherein $R_{20}$ is as defined below.

$R_{20}$ is alkyl of one to 7 carbon atoms, inclusive.

$R_{21}$ is the same as $R_1$, but replacing $-COOR_3$ with $-COOR_{26}$ wherein $R_{26}$ is an alkali metal cation.

$R_{22}$ is hydrogen or $-OSi(R_{17})_3$ wherein $R_{17}$ is as defined above.

$R_{23}$ is hydrogen or $-OR_{24}$ wherein $R_{24}$ is carboxyacyl as defined below.

$R_{24}$ is carboxyacyl including

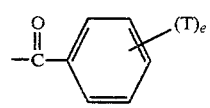

wherein "T" is alkyl of one to 4 carbon atoms, inclusive, bromo, phenylalkyl of 7 to 10 carbon atoms, inclusive, or nitro, and "e" is zero to 5, inclusive, provided that not more than two T's are other than alkyl, and that the total number of carbon atoms in the T's does not exceed 10 carbon atoms,

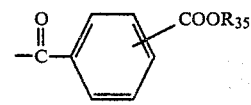

wherein $R_{35}$ is alkyl of one to 4 carbon atoms, inclusive,

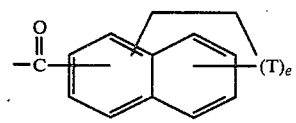

wherein "T" and "e" are as defined above, or

wherein $R_{36}$ is hydrogen, alkyl of one to 19 carbon atoms, inclusive, or aralkyl of 7 to 12 carbon atoms, inclusive, wherein alkyl or aralkyl are substituted with zero to 3 halo atoms.

$R_{25}$ is a blocking group including tetrahydropyranyl, tetrahydrofuranyl, or a group of the formula

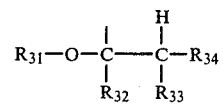

wherein $R_{31}$ is alkyl of one to 18 carbon atoms, inclusive, cycloalkyl of 3 to 10 carbon atoms, inclusive, aralkyl of 7 to 12 carbon atoms, inclusive, phenyl, or phenyl substituted with one, 2, or 3 alkyl of one to 4 carbon atoms, inclusive, wherein $R_{32}$ and $R_{33}$ are the same or different, being hydrogen, alkyl of one to 4 carbon atoms, inclusive, phenyl or phenyl substituted with one, 2, or 3 alkyl of one to 4 carbon atoms, inclusive, or, when $R_{32}$ and $R_{33}$ are taken together, $-(CH_2)_a-$ or $-(CH_2)_b-O-(CH_2)_c-$ wherein a is 3, 4, or 5, b is one, 2, or 3, and c is one, 2, or 3 with the proviso that b plus c is 2, 3, or 4, and wherein $R_{34}$ is hydrogen or phenyl.

$R_{26}$ is an alkali metal cation.

$R_{27}$ is hydrogen, $-OR_{24}$, or $-CH_2OR_{24}$ wherein $R_{24}$ is carboxyacyl as defined above.

$R_{28}$ is hydrogen or methyl.

$R_{29}$ is straight-chain alkyl of 3 to 7 carbon atoms.

$R_{30}$ is alkyl of one to 4 carbon atoms, inclusive.

$R_{31}$, $R_{32}$, $R_{33}$, and $R_{34}$ are as defined for $R_{25}$ above.

$R_{35}$ and $R_{36}$ are as defined for $R_{24}$ above.

$R_{37}$ is alkyl of one to 4 carbon atoms, inclusive.

$R_{38}$ is hydrocarbyl of one to 18 carbon atoms, inclusive.

SePh is phenylselenidyl ($-Se-C_6H_5$).

$(T)_e$ is alkyl of one to 4 carbon atoms, inclusive, phenylalkyl of 7 to 10 carbon atoms, inclusive, or nitro, and e is zero to 5, inclusive, provided that not more than two T's are other than alkyl, and that the total number of carbon atoms in the T's does not exceed 10 carbon atoms.

THP is tetrahydropyranyl.

X is
(1) trans$-CH=CH-$
(2) cis$-CH=CH-$ (3) —C≡C— or
(4) —CH₂CH₂—,

X₁ is
(1) trans—CH=CH—
(2) cis—CH=CH—
(3) —CH₂CH₂— or
(4) —CH=C(Hal)—
wherein Hal is chloro, bromo, or iodo.

e is zero to 5, inclusive.
j is one to 4, inclusive.
m is 2 to 5, inclusive.
n is one to 5, inclusive.
p is 2, 3, or 4.
q is one, 2, or 3.
~ (wavy line) indicates attachment in cis or trans (or alpha or beta) configuration. (END OF TABLE).

There are further provided 19-hydroxy-19-methyl compounds of formula 15 wherein (PC) is as defined above for formula 4.

Among the compounds of formulas 4 and 15, for group I as represented by formula 5 there are PGI₂ compounds
when M₁ is

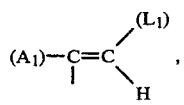

there are PGI₁ compounds when M₁ is

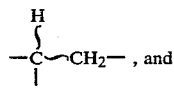

there are 6-hydroxy-PGI compounds (in equilibrium with 6-oxo-PGF₁α compounds) when M₁ is

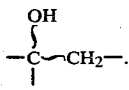

For group II, represented by formula 6, there are 5,9-epoxy analogs of PGI₂ or PGI₁. For background see U.S. Pat. No. 4,123,441.

For group III, represented by formula 7 there are 6,9-epoxymethano analogs of PGI₂ or PGI₁. For background see U.S. Pat. No. 4,124,599.

For group IV, represented by formula 8, there are 5-hydroxy-PGI₁ compounds. For background see U.S. Pat. No. 4,110,532.

For group V, represented by formula 9, there are 4-didehydro ("Δ⁴")-PGI₁ compounds. For background see U.S. Pat. No. 4,109,082.

For group VI, represented by formula 10, there are 6-alkoxy-PGI₁ compounds.

For group VII, represented by formula 11, there are 4-oxo-PGI₁ compounds. For background see U.S. Pat. No. 4,126,744.

For group VIII, represented by formula 12, there are Δ⁶-PGI₁ compounds. For background see U.S. Pat. No. 4,128,713.

For group IX, represented by formula 13, there are Δ⁷-PGI₁ compounds. For background see U.S. Pat. No. 4,151,351.

For group X, represented by formula 14, there are 6a-carba prostacyclin analogs.

Furthermore, there are 11-deoxy compounds when R₂ is hydrogen, and
there are 11-deoxy-11-hydroxymethyl compounds when R₂ is hydroxymethyl.

There are included acids, esters, and salts when R₁ is —COOR₃,
there are C-1 alcohols, i.e. 2-decarboxy-2-hydroxymethyl derivatives when R₁ is —CH₂OH,
there are C-1 amines, i.e. 2-decarboxy-2-aminomethyl derivatives when R₁ is —CH₂N(R₇)(R₈).
there are C-1 amides, when R₁ is

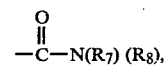

there are sulfonylamides, when R₁ is

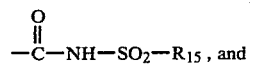

there are C-1 tetrazole derivatives when R₁ is

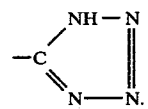

For those compounds of formulas 4 and 15 wherein Q is

i.e. wherein the C-15 hydroxyl group is attached to the side chain in alpha configuration, the configuration at C-15 is identical with that of the naturally occuring prostaglandins such as PGE₁ obtained from mammalian tissues. The 15-epimer compounds are represented by formulas 4 and 15 when Q is

and are identified variously as "15-epi" or "15β" or "15R" by the appropriate prefix in the name. As is known in the art, "R" and "S" designations depend on the neighboring substituents. See R. S. Cahn, J. Chem. Ed. 41, 116 (1964).

The cis-13 prostaglandin derivatives are generally represented herein with a lower side chain shown partially as follows

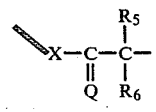

wherein X is cis-CH=CH— and, for the S configuration, Q is

This is intended to be equivalent to the representation

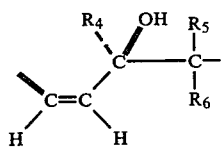

for the S configuration with the C-15 hydroxy in the 15β configuration as drawn (cf. U.S. Pat. No. 4,026,909 column 13).

A typical example of the formula-4 compounds is represented by formula 228 and is named herein "(19R,S)-19hydroxy-PGI$_2$, methyl ester". The full chemical name is (5Z,9α,11α,13E,15S,19R,S)-6,9-epoxy-11,15,19-trihydroxy-prosta-5,13-dien-1-oic acid, methyl ester. The formula-228 compound is a species of the formula-4 compounds wherein $\widehat{PQ}$ is of Group I represented by formula 5 wherein L$_1$ is —(CH$_2$)$_3$—, M$_1$ is

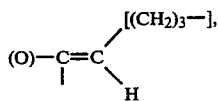

Q is

R$_1$ is —COOCH$_3$, R$_2$ is hydroxyl, R$_5$ and R$_6$ are hydrogen, and X is trans-CH=CH—.

The nomenclature of these compounds follows that of the prostacyclins. For example, compounds having longer or shorter side chains are named as "homo" or "nor" compounds, respectively.

The products of this invention within the scope of formula 4 and 15 are extremely potent in causing various biological responses. For that reason, these compounds are useful for pharmacological purposes. A few of these biological responses are: inhibition of blood platelet aggregation, inhibition of gastric secretion and reduction of undesirable gastrointestinal effects from systemic administration of prostaglandin synthetase inhibitors, controlling spasm and facilitating breathing in asthmatic conditions, and decongesting nasal passages.

Because of these biological responses, these novel compounds are useful to study, prevent, control, or alleviate a wide variety of diseases and undesirable physiological conditions in mammals, including humans, useful domestic animals, pets, and zoological specimens, and in laboratory animals, for example, mice, rats, rabbits and monkeys.

These compounds are useful whenever it is desired to inhibit platelet aggregation, to reduce the adhesive character of platelets, and to remove or prevent the formation of thrombi in mammals, including man, rabbits, and rats. For example, these compounds are useful in the treatment and prevention of myocardial infarcts, to treat and prevent post-operative surgery, and to treat conditions such as arthrosclerosis, arteriosclerosis, blood clotting defects due to lipemia, and other clinical conditions in which the underlying etiology is associated with lipid imbalance or hyperlipidemia. Other in vivo applications include geriatric patients to prevent cerebral ischemic attacks and long-term prophylaxis following myocardial infarcts and strokes. For these purposes, these compounds are administered systemically, e.g., intravenously, subcutaneously, intramuscularly, and in the form of sterile implants for prolonged action. For rapid response, especially in emergency situations, the intravenous route of administration is preferred. Doses in the range of about 0.01 to about 10 mg. per kg. of body weight per day are used, the exact dose depending on the age, weight, and condition of the patient or animal, and on the frequency and route of administration.

The addition of these compounds to whole blood provides in vitro applications such as storage of whole blood to be used in heart-lung machines. Additionally whole blood containing these compounds can be circulated through limbs and organs, e.g. heart and kidneys, whether attached to the original body, detached and being preserved or prepared for transplant, or attached to a new body. Blocking of aggregated platelets is avoided by the presence of these compounds. For this purpose, the compound is added gradually or in single or multiple portions to the circulating blood, to the blood of the donor person or animal, to the perfused body portion, attached or detached, to the recipient, or to two or all of those at a total steady state dose of about 0.001–1.0 μg./ml. of whole blood. These compounds are also useful in preparing platelet-rich concentrates from blood for use in treating thrombocytopenia or in chemotherapy.

These compounds are also useful in mammals, including man and certain useful animals, e.g. dogs and pigs, to reduce and control excessive gastric secretion, thereby to reduce or avoid gastrointestinal ulcer formation, and accelerate the healing of such ulcers already present in the gastrointestinal tract. For this purpose, these compounds are injected or infused intravenously, subcutaneously, or intramuscularly in an infusion dose range of about 0.01 to about 10 mg. per kg. of body weight per day, the exact dose depending on the age, weight, and condition of the patient or animal, and on the frequency and route of administration.

These compounds are also useful in reducing the undesirable gastrointestinal effects resulting from systemic administration of anti-inflammatory prostaglandin synthetase inhibitors, and are used for that purpose by concomitant administration of the formula-4 or -15 compound and the anti-inflammatory prostaglandin synthetase inhibitor. See Partridge et al., U.S. Pat. No. 3,781,429, for a disclosure as to the administration of certain prostaglandins of the E and A series. The anti-inflammatory synthetase inhibitor, for example indomethacin, aspirin, or phenylbutazone is administered in any of the ways known in the art to alleviate an inflammatory condition, for example, in any dosage regimen and by any of the known routes of systemic administration. The formula-4 or -15 compound is administered along with the anti-inflammatory prostaglandin synthetase inhibitor either by the same route of administration or by a different route. The dosage regimen for the formula-4 or -15 compound in accord with this treatment will depend upon a variety of factors, including the type, age, weight, sex and medical condition of the mammal, the nature and dosage regimen of the anti-inflammatory synthetase inhibitor being administered to the mammal, and the sensitivity of the particular formula-4 or -15 compound to be administered. For example, not every human in need of an anti-inflammatory substance experiences the same adverse gastrointestinal effects when taking the substance. The gastrointestinal effects will frequently vary substantially in kind and degree. But it is within the skill of the attending physician or veterinarian to determine that administration of the anti-inflammatory substance is causing undesirable gastrointestinal effects in the human or animal subject and to prescribe an effective amount of the formula-4 or -15 compound to reduce and then substantially to eliminate those undesirable effects.

These compounds are also useful in the treatment of asthma. For example they are useful as bronchodilators or as inhibitors of mediators, such as SRS-A, and histamine which are released from cells activated by an antigen-antibody complex. Thus, these compounds control spasm and facilitate breathing in conditions such as bronchial asthma, bronchitis, bronchiectasis, pneumonia and emphysema. For these purposes, these compounds are administered in a variety of dosage forms, e.g., orally in the form of tablets, capsules, or liquids; rectally in the form of suppositories; parenterally, subcutaneously, or intramuscularly, with intravenous administration being preferred in emergency situations; by inhalation in the form of aerosols or solutions for nebulizers; or by insufflation in the form of powder. Doses in the range of about 0.01 to 5 mg. per kg. of body weight are used 1 to 4 times a day, the exact dose depending on the age, weight, and condition of the patient and on the frequency and route of administration. For the above use the compound can be combined advantageously with other anti-asthmatic agents, such as sympathomimetics (isoproterenol, phenylephrine, ephedrine, etc.), xanthine derivatives (theophylline and aminophylline), and corticosteroids (ACTH and prednisolone).

These compounds are effectively administered to human asthma patients by oral inhalation or by aerosol inhalation. For administration by the oral inhalation route with conventional nebulizers or by oxygen aerosolization it is convenient to provide the formula-4 or -15 ingredient in dilute solution, preferably at concentrations of about 1 part of medicament to from about 100 to 200 parts by weight of total solution. Entirely conventional additives may be employed to stabilize these solutions or to provide isotonic media, for example, sodium chloride, sodium citrate, citric acid, and the like can be employed. For administration as a self-propelled dosage unit for administering the active ingredient in aerosol form suitable for inhalation therapy the composition can comprise the active ingredient suspended in an inert propellant (such as a mixture of dichlorodifluoromethane and dichlorotetrafluoroethane) together with a co-solvent, such as ethanol, flavoring materials and stabilizers. Instead of a co-solvent there can also be used a dispensing agent such as oleyl alcohol. Suitable means to employ the aerosol inhalation therapy technique are described fully in U.S. Pat. No. 2,868,691 for example.

These compounds are useful in mammals, including man, as nasal decongestants and are used for this purpose in a dose range of about 10 μg to about 10 mg. per ml. of a pharmacologically suitable liquid vehicle or an an aerosol spray, both for topical application.

These compounds are also useful in treating peripheral vascular disease in humans. The term peripheral vascular disease are used herein means disease of any of the blood vessels outside of the heart and to disease of the lymph vessels, for example, frostbite, ischemic cerebrovascular disease, arteriovenous fistulas, ischemic leg ulcers, phlebitis, venous insufficiency, gangrene, hepatorenal syndrome, ductus arteriosus, non-obstructive mesenteric ischemia, arteritis lymphangitis and the like. These examples are included to be illustrative and should not be construed as limiting the term peripheral vascular disease. For these conditions the compounds are administered orally or parenterally via injection or infusion directly into a vein or artery. The dosages of such compounds are in the range of 0.01-1.0 μg. administered by infusions at an hourly rate or by injection on a daily basis, i.e. 1-4 times a day, the exact dose depending on the age, weight, and condition of the patient and on the frequency and route of administration. Treatment is continued for one to five days, although three days is ordinarily sufficient to assure long-lasting therapeutic action. In the event that systemic or side effects are observed the dosage is lowered below the threshold at which such systemic or side effects are observed. These compounds are accordingly useful for treating peripheral vascular diseases in the extremities of humans who have circulatory insufficiencies in said extremitites, such treatment affording relief of rest pain and induction of healing of ulcers. For a complete discussion of the nature of and clinical manifestations of human peripheral vascular disease and the method previously known of its treatment with prostaglandins see South African Pat. No. 74/0149 referenced as Derwent Farmdoc No. 58400V. See Elliott et al., Lancet, Jan. 18, 1975, pp. 140-142.

These compounds are also useful as hypotensive agents to reduce blood pressure in mammals, including man. For this purpose, the compounds are administered by intravenous infusion at the rate of about 0.01 to about 50 μg. per kg. of body weight per miute or in single or multiple doses of about 25 to 500 μg. per kg. of body weight total per day. The exact dosages for this purpose depend upon the age, weight, and condition of the patient or animal.

There are further provided the various processes for preparing the compounds of formulas 4 and 15. Thus, for the Group-I type compounds of either formula 4 or 15 (i.e. 19-hydroxy or 19-hydroxy-19-methyl compounds, respectively) one process illustrated by Chart 1 herein comprises the steps of starting with a $PGF_{2\alpha}$ compound of formula 16 and (a) transforming that starting compound to a halo compound of formula 17, (b) subjecting the product of step "a" to dehydrohalogenation with a tertiary amine or a reagent selected from the group consisting of sodium or potassium superoxide, sodium or potassium carbonate, sodium or potassium hydroxide, sodium or potassium benzoate, sodium or potassium acetate, sodium or potassium trifluoroacetate, sodium or potassium bicarbonate, silver acetate, and a tetraalkylammonium superoxide of the formula $(R_{37})_4NO_2$ wherein $R_{37}$ is alkyl of one to 4 carbon atoms, inclusive to form an enol ether of formula 18 and (c) separating the products.

Transformation at C-1 and C-2 to ester, alcohol, amine, amide, sulfonamide, or tetrazolyl groups within the scope of $R_1$ are made by methods known in the art or disclosed herein. Likewise, transformations or substitutions for $L_4$, Q, $R_2$, $R_5$, $R_6$, and X are made by methods known in the art or disclosed herein.

Reference to the CHARTS herein will make clear the processes for preparing the compounds of this invention. Charts 1–31, in general, relaive principally to the compounds within the scope of Groups I–X as defined above and as further illustrated in the Examples below. Charts 32–45 relative to intermediates or starting materials for those compounds as elucidated in the Preparations below. Those processes not illustrated in the charts are based on chemical procedures generally known to those skilled in the art. The steps of the charts will be discussed in detail below.

With regard to Charts 1–45, examples of alkyl of one to 4 carbon atoms, inclusive, are methyl, ethyl, propyl, butyl, and isomeric forms thereof. Examples of alkyl of one to 7 carbon atoms, inclusive, are those given above and pentyl, hexyl, heptyl, and isomeric forms thereof. Examples of alkyl of one to 19 carbon atoms, inclusive, are those given above and octyl, nonyl, decyl, undecyl, dodecyl, tridecyl, tetradecyl, pentadecyl, hexadecyl, heptadecyl, octadecyl, nonadecyl, and isomeric forms thereof. Examples of cycloalkyl of 3 to 10 carbon atoms, inclusive, which includes alkyl-substituted cycloalkyl, are
cyclopropyl,
2-methylcyclopropyl,
2,2-dimethylcyclopropyl,
2,3-diethylcyclopropyl,
2-butylcyclopropyl,
cyclobutyl,
2-methylcyclobutyl,
3-propylcyclobutyl,
2,3,4-triethylcyclobutyl,
cyclopentyl,
2,2-dimethylcyclopentyl,
2-pentylcyclopentyl,
3-tert-butylcyclopentyl,
cyclohexyl,
4-tert-butylcyclohexyl,
3-isopropylcyclohexyl,
2,2-dimethylcyclohexyl,
cycloheptyl,
cyclooctyl,
cyclononyl, and
cyclodecyl.
Examples of aralkyl of 7 to 12 carbon atoms, inclusive are
benzyl,
phenethyl,
1-phenylethyl,
2-phenylpropyl,
4-phenylbutyl,
3-phenylbutyl,
2-(1-naphthylethyl), and
1-(2-naphthylmethyl).
Examples of phenyl substituted with one, 2, or 3 chloro or alkyl groups of one to 3 carbon atoms, inclusive, are
p-chlorophenyl,
m-chlorophenyl,
o-chlorophenyl,
2,4-dichlorophenyl,
2,4,6-trichlorophenyl,
4-chloro-2-methylphenyl,
2,4-dichloro-3-methylphenyl,
(o-, m-, or p-)tolyl,
p-ethylphenyl, and
2,5-dimethylphenyl.

Examples of phenyl substituted with hydroxycarbonyl or alkoxycarbonyl in which the alkoxy group consists of one to 4 carbon atoms, inclusive, are (o-, m-, p-)-carboxyphenyl, methyl (o-, m-, p-) carboxymethyl, and isopropyl (o-, m-, p-)-carboxyphenyl.

Examples of hydrocarbyl of one to 18 carbon atoms, inclusive, are any of the examples of alkyl of one to 18 carbon atoms, cycloalkyl of 3 to 10 carbon atoms, and aralkyl of 7 to 12 carbon atoms given above.

To obtain the optimum combination of biological response specificity, potency, and duration of activity, certain compounds within the scope of formulas 4 and 15 are preferred. For example it is preferred that Q be

wherein it is especially preferred that $R_4$ be hydrogen or methyl.

When Q is

it is preferred that $R_4$ be methyl.

Another preference for the compounds of formulas 4 and 15, as to $R_1$, is that $R_3$ in —$COOR_3$ be either hydrogen or alkyl of one to 12 carbon atoms, inclusive, or a salt of a pharmacologically acceptable cation. Further, when $R_3$ is alkyl, it is more preferred that it be alkyl of one to 4 carbon atoms, and especially methyl or ethyl.

Still another preference for the 19-hydroxy compounds of formulas-4 and 15 is that the 19-hydroxy configuration be "R".

Because of their relative instability, enol ethers of formulas 18, 39, 51, and 96 are preferably not stored for protracted periods as their free acids wherein $R_1$ is —COOH, but preferably as salts, esters, or other C-1 derivatives.

Group I Compounds

Chart relates to Group I compounds, as defined above, wherein $M_1$ is

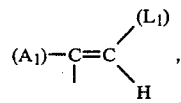

i.e., $PGI_2$-type compounds. In Chart 1, starting materials of formula 16 are $PGF_{2\alpha}$-type compounds having the 19-hydroxy group with or without the 19-methyl group. For background on 19-hydroxy-PGF's, see for example J. C. Sih, Prostaglandins 13, 831–835 (1977) and references cited therein. These formula-16 compounds are not the subject of the present invention, but they are available by processes disclosed in the Preparations herein and accompanying Charts 32–45 which will be discussed below.

Continuing with Chart 1, in step (a) the starting material 16 is subjected to halogenation and cyclization to yield the formula-17 halo compounds. For this purpose there are various methods available. For the iodo compounds there may be used an aqueous system containing iodine, potassium iodide, and an alkali carbonate or bicarbonate, or an organic solvent system such as dichloromethane containing iodine in the presence of an alkali metal carbonate. The reaction is carried out at temperatures below 25° C., preferably about 0°–5° C. for 10–20 hours. Thereafter the reaction is quenched with sodim sulfite and sodium carbonate and the formula-17 compound separated from the reaction mixture.

For the bromo compounds, N-bromosuccinimide or N-bromoacetamide are useful. See Fieser et al., Reagents for Organic Synthesis, Vol. I, pp. 74 and 78, Vol. IV, p. 51, John Wiley and Sons, Inc., N.Y. For the chloro compound various methods are available, for example exchange of bromo with chloro with the silver salt of chlorodifluoroacetic acid. See I. T. Harrison et al., Compendium of Organic Synthetic Methods, p. 346, 1971, Wiley Interscience, N.Y.

The formula-17 halo compounds are obtained as two isomers, one in minor and the other in major quantity, differing in their chromatographic mobility. Normally these isomers need not be separated, as either one yields the desired products in step "b" of Chart 1.

In step "b" of Chart 1, compound 17 is converted to the formula-18 enol ether compound by contacting it with a dehydrohalogenation reagent. For such reagents see, for example, Fieser and Fieser, "Reagents for Organic Synthesis" p. 1308, John Wiley and Sons, Inc., New York, N.Y. (1967). Preferred for the reaction of step "b" are tertiary amines and reagents selected from the group consisting of sodium or potassium superoxide, sodium or potassium carbonate, sodium or potassium hydroxide, sodium or potassium benzoate, sodium or potassium acetate, sodium or potassium trifluoroacetate, sodium or potassium bicarbonate, silver acetate, and a tetraalkylammonium superoxide of the formula $R_{37})_4NO_2$ wherein $R_{37}$ is alkyl of one to 4 carbon atoms, inclusive.

Of the tertiary amines, preferred amines are
1,5-diazabicyclo[4.3.9]nonene-5 ("DBN"),
1,4-diazabicyclo[2.2.2]octane ("DABCO"),
1,5-diazabicyclo[5.4.0]undecene-5 ("DBU").
Other preferred reagents are sodium or potassium superoxide and tetramethylammonium superoxide. For further information on the superoxide see Johnson and Nidy, J. Org. Chem. 40, 1680 (1975). For larger scale preparation the electrochemical generation of superoxide is recommended. See Dietz et al. J. Chem. Soc. (B), 1970, pp. 816–820.

The dehydrohalogenation step is carried out in an inert organic medium such as dimethylformamide and is followed by TLC to show the disappearance of starting material. The reaction proceeds at 25° C. and can be accelerated at 40°–50° C.

In working up the reaction mixture it is advantageous to maintain basic conditions, e.g. with triethylamine, to avoid acidic decomposition or structural changes of the product. Purification is achieved by crystallization and consequent separation from impurities or starting material left in the mother liquor, or by column chromatography. For chromatographic separation a column of magnesium silicate ("Florisil R") is preferred over silica gel. Decomposition of the product is avoided by pretreating the column with triethylamine.

Group-I (5E) compounds in which $M_1$ is

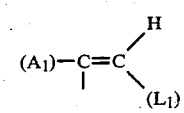

are prepared by substituting corresponding 5,6-trans-PGF$_2$-type starting materials for the formula-16 compounds of Chart 1.

Ester groups such as the p-phenylphenacyl group on the C-1 carboxyl are unchanged by the transformations of Chart 1, and, if present on the formula-16 starting material, are also present on the formula-18 product. For the final products of formula 18 which are esters or amides the preferred method of preparation is from formula-17 halo compounds which are corresponding esters or amides.

Other transformations at C-1 in general are performed either on the starting material, the intermediate or intermediates, or on the final product by chemical processes which are known to those skilled in the art. For example, if a lower alkyl ester is available or produced according to Chart 1, as well as successive Charts 2–31, that ester is readily converted to the acid form by saponfication. The acid is then used to prepare various esters of formulas 4 and 15 within the scope of $R_3$ by methods known in the art. For example, the alkyl, cycloalkyl, and aralkyl esters are prepared by interaction of said acids with the appropriate diazohydrocarbon. For example, when diazomethane is used, the methyl esters are produced. Similar use of diazoethane, diazobutane, 1-diazo-2-ethylhexane, diazocyclohexane, and phenyldiazomethane, for example gives the ethyl, butyl, 2-ethylhexyl, cyclohexyl, and benzyl esters, respectively. Of these esters, the methyl or ethyl are preferred.

Esterification with diazohydrocarbons is carried out by mixing a solution of the diazohydrocarbon in a suitable inert solvent, preferably diethyl ether, with the acid reactant, advantageously in the same or a different inert diluent. After the esterification reaction is complete, the solvent is removed by evaporation, and the ester purified, if desired, by conventional methods, preferably by chromatography. It is preferred that contact of the acid reactants with the diazohydrocarbon be no longer than necessary to effect the desired esterification, preferably about one to about ten minutes, to avoid undesired molecular changes. Diazohydrocarbons are known in the art or can be prepared by methods known in the art. See, for example Organic Reactions, John Wiley & Sons, Inc., New York, N.Y., Vol. 8, pp. 389–394 (1954).

An alternative method for esterification of the carboxyl moiety of the acid compounds of formulas 4 and 15 or their intermediates comprises transformations of the free acid to the corresponding silver salt, followed by interaction of that salt with an alkyl iodide. Examples of suitable iodides are
methyl iodide,
ethyl iodide,
butyl iodide,
isobutyl iodide,
tert-butyl iodide,
cyclopropyl iodide,
cyclopentyl iodide,
benzyl iodide,
phenethyl iodide, and the like. The silver salts are prepared by conventional methods, for example, by dissolving the acid in cold dilute aqueous ammonia, evaporating the excess ammonia at reduced pressure, and then adding the stoichiometric amount of silver nitrate.

The phenyl and substituted phenyl esters of the formula 4 and 15 compounds or their intermediates are prepared by silylating the acid to protect the hydroxy groups, for example, replacing each —OH with —O—Si—(CH$_3$)$_3$. Doing that may also change —COOH to —COO—Si—(CH$_3$)$_3$. A brief treatment of the silylated compound with water will change —COO—Si(CH$_3$)$_3$ back to —COOH. Procedures for this silylation are known in the art and are available. Then, treatment of the silylated compound with oxalyl chloride gives the acid chloride which is reacted with phenol or the appropriate substituted phenol to give a silylated phenyl or substituted phenyl ester. Then the silyl groups, e.g., —O—Si—(CH$_3$)$_3$ are changed back to —OH by treatment with dilute acetic acid. Procedures for these transformations are known in the art.

A preferred method for substituted phenyl esters is that disclosed in U.S. Pat. No. 3,890,372 in which a mixed anhydride is reacted with an appropriate phenol or naphthol. The anhydride is formed from the acid with isobutylchloroformate in the presence of a tertiary amine.

Phenacyl-type esters are prepared from the acid using a phenacyl bromide, for example p-phenylphenacyl bromide, in the presence of a tertiary amine. See for example U.S. Pat. No. 3,984,454, German Offenlag. 2,535,693, and Derwent Farmdoc No. 16828X.

Charts 36–40 relate to transformations at C-1 for these 19-hydroxy compounds of formulas 4 and 15 or their intermediates.

When a 2-decarboxy-2-hydroxymethyl product is desired, i.e., when R$_1$ is —CH$_2$OH, the acid or lower alkyl ester form is reduced (see Chart 36 formula 177 to 178) using reagents known to reduce carboxylic acids to corresponding primary alcohols. See for example U.S. Pat. No. 4,028,419, as to lithium aluminum hydride or diisobutylaluminum hydride. Useful solvents include diethyl ether, tetrahydrofuran or dimethoxyethane. The reaction may be run at −78° C. to 100° C., although preferably at about 0° C. to 50° C. Other carbonyl groups in the molecule will also be reduced unless suitably protected as oximes, ketals, or similar carbonyl derivatives which are readily restored to carbonyls after the reduction has been accomplished.

A 2-decarboxy-2-hydroxymethyl-PGE type compound may also be prepared by blocking the C-1 alcohol groups as shown in Chart 36, formula 180. Thereafter the C-9 hydroxy is oxidized to form 181 and finally the —Si(R$_{17}$)$_3$ blocking group is removed by hydrolysis. It is preferred that —Si(R$_{17}$)$_3$ be tert-butyl-dimethylsilyl.

Compounds in which R$_1$ is

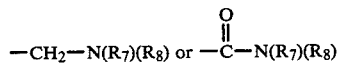

are conveniently prepared from the formula-4 or 15 products or intermediates which are acids, i.e. R$_1$ is —COOH. For background see U.S. Pat. No. 4,085,139. The compounds are simply converted to a mixed anhydride using an alkyl, aralkyl, phenyl, or substituted phenyl chloroformate in the presence of a tertiary amine. A preferred reagent is isobutylchloroformate.

The anhydride is then reacted with ammonia or the appropriate amine (R$_7$)(R$_8$)NH to form the amide wherein R$_1$ is

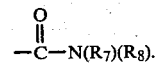

The 2-decarboxy-2-aminomethyl compound is prepared from the amide by carbonyl reduction using methods known in the art, for example lithium aluminum hydride reduction. See Chart 37.

Compounds in which R$_1$ is

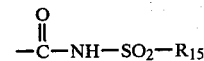

i.e. the N-sulfonylamides, are prepared from the formula-16 compounds in their acid form. In Chart 38 are shown the steps by which those compounds, represented by formula 183, are transformed to the sulfonylamides of formula 189. In step (a) the acid is converted to a mixed anhydride, here shown at 188, by reaction with isobutylchloroformate in the presence of a tertiary amine such as triethylamine. Other mixed anhydrides are also useful. In step (b) the anhydride is then reacted with the sodium derivative of a sulfonylamide of the formula Na—NH—SO$_2$R$_{15}$ obtained for example by reaction of methanolic sodium methoxide with an equimolar amount of the sulfonylamide. The reaction of step (b) is promoted by the addition of a small amount of hexamethylphosphoramide to insure homogeneity.

Compounds in which R$_1$ is

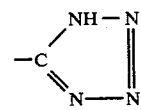

are obtained by either the process of Chart 39 or Chart 40. In Chart 39 the starting lactone 190 is available above, for example by reduction of 170. Applying the Wittig reaction and using the ylid prepared from a phosphonium compound of formula 239, the formula-191 compound is obtained. See U.S. Pat. No. 3,928,391. Replacement of blocking groups R$_{25}$ then yields the products of formula 192. The 191 compounds are transformed by methods disclosed herein or known in the art to tetrazolyl compounds within the scope of formula 4.

In Chart 40 the process goes stepwise from an amide to a nitrile to a tetrazolyl compound. The starting materials 193 are available herein, for example from an acid blocked preferentially with R$_{25}$ at C-11 and C-15 and converted to an amide by way of a mixed anhydride, then blocked with silyl groups at C-9.

In step (a) the formula-194 nitrile is prepared by dehydration of amide 193 with a carbodiimide. See C. Ressler et al., J. Org. Chem. 26, 3354 (1961). For example, N.N'-dicyclohexylcarbodiimide (DCC) is useful in pyridine at about room temperature.

In step (b) the tetrazolyl group in 195 is formed from the above nitrile by reaction with sodium azide and ammonium chloride in a medium such as dimethylformamide. See "Heterocyclic Compounds", R. C. Elderfield., ed., John Wiley and Sons, Inc., N.Y., Vol. 8, pages 11–12.

In steps (c) and (d) the blocking groups —Si(R$_{17}$)$_3$ and R$_{25}$ are replaced by desilylation and mild acid hydrolysis in the usual manner to yield 196 and then 197. Compound 196 is useful as an intermediate for preparing tetrazolyl compounds within the scope of formula 4.

Included in the compounds of formulas 4 and 15 are the salts when R$_3$ is a pharmacologically acceptable cation. Such pharmacologically acceptable salts useful for the purposes described above are those with pharmacologically acceptable metal cations, ammonium, amine cations, or quaternary ammonium cations.

Especially preferred metal cations are those derived from the alkali metals, e.g., lithium, sodium and potassium, and from the alkaline earth metals, e.g., magnesium and calcium, although cationic forms of other metals, e.g., aluminum, zinc, and iron are within the scope of this invention.

Pharmacologically acceptable amine cations are those derived from primary, secondary, or tertiary amines. Examples of suitable amines are:
methylamine,
dimethylamine,
trimethylamine,
ethylamine,
dibutylamine,
triisopropylamine,
N-methylhexylamine,
decylamine,
dodecylamine,
allylamine,
crotylamine,
cyclopentylamine,
dicyclohexylamine,
benzylamine,
dibenzylamine,
α-phenylethylamine,
β-phenylethylamine,
ethylenediamine,
diethylenetriamine,
and like aliphatic, cycloaliphatic, and araliphatic amines containing up to and including about 18 carbon atoms, as well as heterocyclic amines, e.g.,
piperidine,
morpholine,
pyrrolidine,
piperazine,
and lower-alkyl derivatives thereof, e.g.
1-methylpiperidine,
4-ethylmorpholine,
1-isopropylpyrrolidine,
2-methylpyrrolidine,
1,4-dimethylpiperazine,
2-methylpiperidine,
and the like, as well as amines containing water-solubilizing or hydrophilic groups, e.g., mono-, di-, and triethanolamine,
ethyldiethanolamine,
N-butylethanolamine,
2-amino-1-butanol,
2-amino-2-ethyl-1,3-propanediol,
2-amino-2-methyl-1-propanol,
tris(hydroxymethyl)aminomethane,
N-phenylethanolamine,
N-(p-tert-amylphenyl)diethanolamine,
galactamine,
N-methylglycamine,
N-methylglucosamine,
ephedrine,
phenylephrine,
epinephrine,
procaine,
and the like.

Examples of suitable pharmacologically acceptable quaternary ammonium cations are tetramethylammonium, tetraethylammonium, benzyltrimethylammonium, phenyltriethylammonium and the like.

Salts containing pharmacologically acceptable cations are prepared from the final formula-4 and 15 compounds in free acid form, i.e. wherein R$_1$ is —COOH, by neutralization with appropriate amounts of the corresponding inorganic or organic base, examples of which correspond to the cations and amines listed above. These transformations are carried out by a variety of procedures known in the art to be generally useful for the preparation of inorganic, i.e., metal or ammonium, salts, amine acid addition salts, and quaternary ammonium salts. The choice of procedure depends in part upon the solubility characteristics of the particular salts to be prepared. In the case of the inorganic salts, it is usually suitable to dissolve the formula-4 and 15 acid in water containing the stoichiometric amount of a hydroxide, carbonate, or bicarbonate corresponding to the inorganic salt desired. For example, such use of sodium hydroxide, sodium carbonate, or sodium bicarbonate gives a solution of the sodium salt. Evaporation of the water or addition of a water-miscible solvent of moderate polarity, for example, a lower alkanol or a lower alkanone, gives the solid inorganic salt if that form is desired. Amine and quaternary ammonium salts are prepared by similar methods using appropriate solvents.

Referring now to Chart 2, there is shown a process for the Group I compounds wherein M$_1$ is

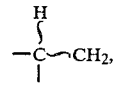

i.e. PGI$_1$-type compounds. Starting materials 16 are converted to a mercury compound of formula 19 which is then subjected to reductive demercuration to form the formula-20 product. For background on the mercuration-demercuration cyclization see, for example, U.S. Pat. No. 4,125,712 and references cited therein, including H. C. Brown et al., Organometal. Chem. Syn. 1, 7(1970).

In step "a" of Chart 2, the starting material is reacted with an appropriate mercury (II) salt corresponding to Hg(G)$_2$, for example mercuric nitrate, chloride, or acetate. Preferred is either mercuric acetate or trifluoroacetate. The reagent is dissolved in either water or acid, e.g. acetic acid, and combined with a solution of the formula-16 starting material in a convenient solvent such as chloroform or tetrahydrofuran. The reaction is conveniently done at about 15°–35° C.

In step "b" of Chart 2 the mercuric compound is subjected to reductive demercuration. Useful reagents for this step include sodium borohyride, sodium amalgam, and hydrazine. Especially preferred is sodium borohydride in alkaline solution, e.g. aqueous sodium hydroxide. The reaction is carried out in a solvent such as tetrahydrofuran at about 15°–35° C. Thereafter the mercury is separated, and the product isolated by methods described herein.

In a modification of the process of Chart 2, the starting material consists of a 19,20-didehydro-("Δ19")-PGF$_{2\alpha}$ compound, blocked with THP at C-11 and C-15. Treatment with mercuric acetate then forms the corresponding mercury compounds. Further treatment with sodium borohydride results in demercuration and formation of the 9 deoxy-6ε,9α-epoxy-(19R,S)-19-hydroxy-PGF$_1$ compounds, as their bis(THP ethers). Deblocking then yields compounds of formula 4. See Example 2 herein.

Chart 3 illustrates the process employed for formula-24 Δ$^2$ compounds of Group I wherein L$_1$ is —CH$_2$CH═CH—. For background in preparing Δ$^2$-prostaglandin analogs, see for example U.S. Pat. No. 4,024,174.

In step "a", selenylation is achieved by first forming 2-lithium derivatives of the formula-21 lower alkyl esters for example by reaction with a lithium amide formed from a secondary amine such as N-isopropylcyclohexylamine. Thereafter the formula-22 compounds are obtained by reaction with diphenyldiselenide or benzeneselenyl bromide using about 3 equivalents for each molecular equivalent of the C-2 lithium derivative at about $-78°$ C.

In step "b" the formula-23 Δ$^2$ compounds are formed by oxidative elimination, for example with hydrogen peroxide or sodium periodate.

In step "c" the formula-24 final compounds are formed within the scope of R$_1$ by methods known in the art or described herein.

Chart 4 shows an alternative process to the PGI$_1$-type compounds using 5-halo intermediates of formula 25, including the formula-17 compounds of Chart 1 and the formula-30 Δ$^2$ compounds of Chart 5.

In step "a" of Chart 4 the halo compound 25 is subjected to reductive dehalogenation. Useful reagents include tributyltin hydride, triphenyltin hydride, sodium borohydride in ethanol or dimethyl sulfoxide, and zinc in acetic acid. Especially preferred is tributyltin hydride freshly prepared from tributyltin chloride and lithium aluminum hydride. The reaction is run in a solvent such as benzene at about 15°–35° C. and monitored by TLC, to yield the formula-26 compounds.

Chart 5 gives a route to Δ$^2$ 5-halo compounds of formula 30. The starting materials 27 are within the scope of the formula-17 compounds of Chart 1 and steps (a)-(c) utilize the same chemistry discussed for the Δ$^2$ compounds of Chart 3.

Chart 6 illustrates the preparation of 6-hydroxy-PGI$_1$ compounds of Group I wherein M$_1$ is

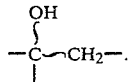

In step "a" the halo compound 25 is converted to an equilibrium mixture of the 6-hydroxy compound 32 and the 6-oxo compound 33 by contacting with silver carbonate and perchloric acid. The reaction is done in an inert organic medium such as tetrahydrofuran and is followed with TLC to determine completion, normally in 15-24 hours at about 25° C. The reaction is preferably done in absence of light.

Although the product of step "a" normally contains compounds 32 and 33, further equilibration may be accomplished merely by preparing a solution of that product in an organic solvent, e.g. acetone or dichloromethane, and letting it stand for several days. The resulting mixture is concentrated and separated, for example by silica gel chromatography.

Still another route to the mixture of 6-hydroxy and 6-oxo compounds 32 and 33 is by treating the formula-25 halo compound in alcoholic solution, e.g. methanol, with aqueous alkali metal hydroxide, e.g. potassium hydroxide, at a temperature in the range of 0° to 30° C. for several hours. After acidification there is obtained a mixture of the acid form of the formula-25 compound and the formula-32 hemi-ketal together with some of the formula-33 6-oxo compound, which are separated, for example, by silica gel chromatography or by fractional cyrstallization.

Chart 7 merely shows a preferred route to the amides of the 6-hydroxy and 6-oxo compounds, by forming the formula-35 amides from the 5-halo compounds of formula 34, and thereafter applying the procedures of Chart 6 to obtain the equilibrium mixture of 36 and 37.

Group II Compounds

Charts 8–12 relate to Group II compounds, as defined above, i.e. enlarged-hetero-ring PGI$_2$ and PGI$_1$ compounds. Chart 8 shows, in step "a", the dehydrohalogenation of compound 38 to yield 39. The reagents and conditions are the same as those employed for Chart 1, step "b". The starting materials of formula 38 are readily available, for example, by the processes of Charts 9 and 10 immediately hereafter. Step "b" of Chart 8 shows the reductive dehalogenation step to yield compound 40 employing the same reagents and conditions as for Chart 4.

Chart 9 shows the preparation of the 4-halo compounds 42, utilizing Δ$^4$-19-hydroxy-PGF$_{1\alpha}$ compounds 41, for which see Chart 45 herein. Step "a" employs the same halogenation-cyclization reagents and conditions as for Chart 1, step "a" above. Chart 10 provides the Δ$^2$ compounds of formula 46 by steps (a)–(c) which follow the same chemistry as those of Chart 5.

Charts 11 and 12 lead to the equilibrium mixtures of the 5-hydroxy and 5-oxo compounds, 47 and 48 respectively. In Chart 11 the formula-39 enol ether of Chart 8 is subjected to mild acid, for example a buffer of pH2, at about 25° C. for 30 min. Chart 12 applies the same procedure as Chart 6 above, using silver carbonate and perchloric acid.

Group-III Compounds

Charts 13–17 relate to Group III compounds as defined above, i.e. enlarged-hetero-ring compounds of the 9-deoxy-6,9α-epoxymethano-PGF types. Chart 13 shows, in step "a" the formation of the corresponding 5-halo-9-deoxy-6,9α-epoxymethano-PGF compounds of formula 50, followed in step "b" by the dehydrohalogenation step yielding the enol ether compounds of formula 51. The halogenation-cyclization and dehydrohalogenation procedures and reagents are the same as employed in Chart 1. The starting materials 49, i.e. 9-deoxy-9-hydroxymethyl-PGF$_{2\alpha}$ analogs, are available from the procedures of Chart 14.

In Chart 14 the ultimate starting materials are 19-hydroxy-PGE$_2$ type compounds of formula 52. Some of these compounds are known in the literature, for example J. C. Sih, Prostaglandins 13, 831 (1977) and references cited therein. General methods of preparation are given in the Preparations hereinafter, referring to Charts 35 and 41. Compounds 52 are provided as lower alkyl esters, wherein $R_{10}$ is alkyl of one to 6 carbon atoms.

In step "a" silylated compound 53 is obtained from 52 by procedures known in the art or described herein. See, for example, Pierce, "Silylation of Organic Compounds", Pierce Chemical Co., Rockford, Illinois (1968). The necessary silylating agents for these transformations are known in the art or are prepared by methods known in the art. See, for example, Post, "Silicones and Other Organic Silicon Compounds", Reinhold Publishing Corp. New York, N.Y. (1949). These reagents are used in the presence of a tertiary base such as pyridine at temperatures in the range of about 0° to +50° C. Examples of trisubstituted monochlorosilanes suitable for this purpose include
chlorotrimethylsilane,
chlorotriisobutylsilane,
tert-butyldimethylchlorosilane,
chlorotriphenylsilane,
chlorotris(p-chlorophenyl)silane,
chlorotri-m-tolylsilane, and
tribenzylchlorosilane.
Alternately, a chlorosilane is used with a corresponding disilazane. Examples of other silylating agents include
pentamethylsilylamine,
pentaethylsilylamine,
N-trimethylsilyldiethylamine,
1,1,1-triethyl-N,N-dimethylsilylamine,
N,N-diisopropyl-1,1,1-trimethylsilylamine,
1,1,1-tributyl-N,N-dimethylsilylamine,
N,N-dibutyl-1,1,1-trimethylsilylamine,
1-isobutyl-N,N,1-tetramethylsilylamine,
N-benzyl-N-ethyl-1,1,1-trimethylsilylamine,
N,N,1-tetramethyl-1-phenylsilylamine,
N,N-diethyl-1,1-dimethyl-1-phenylsilylamine,
N,N-diethyl-1,1-dimethyl-1-phenylsilylamine,
N,N-diethyl-1-methyl-1,1-diphenylsilylamine,
N,N-dibutyl-1,1,1-triphenylsilylamine, and
1-methyl-N,N-1,1-tetraphenylsilylamine.

Although a wide variety of silylating agents are available, it is preferred that the silyl groups on the ring contain at least one hindered group, for example:
isopropyl,
secondary butyl,
tert-butyl,
cyclohexyl, or
phenyl.
The silyl groups with hindered substituents are characterized as being less susceptible to hydrolysis than, for example, trimethylsilyl, and therefore resistant to replacement during subsequent steps, particularly step (d). Examples of preferred silyl groups for the cyclopentane ring are:
isopropyldimethylsilyl,
sec-butyldimethylsilyl,
tert-butyldimethylsilyl,
triisopropylsilyl,
cyclohexyldimethylsilyl, and
triphenylsilyl.

In addition to the silylation methods discussed above, it is advantageous to silylate with a chlorosilane in the presence of imidazole in a solvent such as dimethylformamide. See Corey et al., J. Am. Chem. Soc. 94, 6190 (1972). The temperature range for the reaction is about −10° to +80° C.

In step "b" the formula-54 9-deoxy-9-methylene compounds are formed from the formula-53 compounds using procedures known in the art. See for example U.S. Pat. No. 3,950,363, applying the procedure of C. A. Johnson et al., J. Am. Chem. Soc. 95, 6462 (1973). Here the carbanion of a sulfoximine of formula 229 generated, for example, with an alkyllithium or an alkylmagnesium halide, is reacted with the formula-53 compound to form a sulfonimidoyl adduct of formula 230. Thereafter reductive elimination with, for example aluminum amalgam, in the presence of acids such as acetic acid or hydrochloric acid yields the formula-54 intermediates, generally free of the blocking groups.

In step "c" compound 54 is again silylated to replace any silyl groups lost in step "b". In step "d" hydroboration-oxidation is employed to transform the 9-methylene group of 55 to a 9-hydroxymethyl group (—CH$_2$OH). See especially U.S. Pat. No. 3,950,363 at column 16–17 and 38. Thereafter in step "e" the silyl groups are replaced with hydrogen as known in the art, for example by acid hydrolysis in dilute acetic acid or, for t-butyldimethylsilyl groups, by use of tetrabutylammonium fluoride. See E. J. Corey et al., J. Am. Chem. Soc. 94, 6190 (1972). Finally in step "f" the compounds within the scope of formula 49 are obtained.

Chart 15 shows the preparation of $\Delta^2$ 9-deoxy-6,9$\alpha$-epoxymethano-5-halo compounds useful as starting materials for Chart 16. Starting with formula-58 compounds from Chart 13, formula 50, steps (a)–(c) employ the same procedures and reagents described above for Chart 5.

Chart 16 shows the transformation of 5-halo compound 62 to PGI$_1$-type compound 63, using reductive dehalo- Chart 17 shows the formation of the equilibrium mixture of 6-hydroxy compound 64 and 6-oxo compound 65 from 5-halo compound 62, applying the same procedures as for Chart 6 above.

Group-IV Compounds

Refer to Charts 18 and 19. Chart 18 provides a route to 5-hydroxy-PGI$_1$ compounds 69, starting with PGF$_{2\alpha}$-type compounds 31. See U.S. Pat. No. 4,110,532, especially Columns 10–15.

In step "a" mercuroacetylation of 31 yields 66, by reaction with mercuric acetate, Hg(OAc)$_2$. Organic solvents such as tetrahydrofuran are conveniently used, with reaction temperatures at or below ambient temperature.

In step "b" compound 67 is formed by halo displacement of the acetate radical of 66. For this purpose, an aqueous solution of the sodium halide NaHal (e.g. sodium chloride or sodium bromide) is employed, simply stirring the reactants together until the reaction is complete as shown by TLC.

In step "c" compound 68 is obtained by reductive oxygenation. The formula-67 compound is reacted with a reducing agent (e.g. sodium borohydride) in the presence of molecular oxygen.

Finally in step "d" products of formula 69 are obtained from the lower alkyl esters represented by 68 by methods described herein or known in the art.

Chart 19 shows the steps for preparing $\Delta2$-5-hydroxy compounds of formula 73. The starting material 70 is available from Chart 18, compound 69. The procedures are the same as for steps (a)–(c) of Chart 3.

Group-V Compounds

Charts 20 and 21 relate to $\Delta4$-PGI$_1$-type compounds. See U.S. Pat. No. 4,109,082 and E. J. Corey et al., J. Am. Chem. Soc. 99, 2006–2008 (1977). Chart 20 shows the steps from a blocked PGF$_{2\alpha}$-type compound of formula 74 to product 77. The starting materials are readily available. For example see Chart 35 (formula 171) and Chart 41, with obvious modifications.

When the blocking group R$_{25}$ is tetrahydropyranyl (THP) or tetrahydrofuranyl, the appropriate reagent, e.g. 2,3-dihydropyran or 2,3-dihydrofuran, is used in an inert solvent such as dichloromethane in the presence of an acid condensing agent such as p-toluenesulfonic acid or pyridine hydrochloride. The reagent is used in slight excess, preferably 1.0 to 1.2 times theory, and the reaction is carried out at about 20°-50° C.

When R$_{25}$ is of the formula R$_{31}$-O-1(R$_{32}$)-CHR$_{33}$R$_{34}$, as defined herein, including 1-ethoxyethyl, the appropriate reagent is a vinyl ether, e.g. ethyl vinyl ether, isopropenyl methyl ether, isobutyl vinyl ether, or any vinyl ether of the formula R$_{31}$-O-C(R$_{32}$)=CR$_{33}$R$_{34}$ wherein R$_{31}$, R$_{32}$, R$_{33}$, and R$_{34}$ are as defined herein; or an unsaturated cyclic or heterocyclic compound, e.g. 1-cyclohexen-1-yl methyl ether

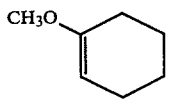

or 5,6-dihydro-4-methoxy-2H-pyran

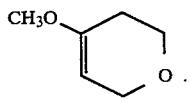

See C. B. Reese et al., J. Am. Chem. Soc. 89, 3366 (1967). The reaction conditions for such vinyl ethers and unsaturates are similar to those for dihydropyran above. In the sequence of steps of Chart 20 it is of course esential that the C-9 hydroxyl of 74 be unblocked.

In step "a" compound 75 is obtained by reaction with phenylselenenyl bromide in a solvent such as tetrahydrofuran at about −20° C. in the presence of a base such as calcium carbonate in equivalent amount.

In step "b" compound 76 results on deblocking 75, for example by mild acid hydrolysis using dilute acetic acid, aqueous citric acid, or aqueous phosphoric acid in a mutual solvent such as tetrahydrofuran. Temperatures of 30°-50° C. are employed.

In step "c" oxidative deselenenylation with hydrogen peroxide at about 0° C. in a solvent such as tetrahydrofuran yields 77.

Chart 21 shows the steps for preparing Δ$^2$,Δ$^4$-PGI$_1$ compounds of formula 81. The starting material 78 is available from Chart 20, and the procedures are the same as for steps (a)–(c) of Chart 3.

Group-VI Compounds

Chart 22 relates to 6-alkoxy-PGI$_1$-type compounds. The starting materials 82 and 83 for step "a" are available, for example, from Chart 6. Either the separate materials or their equilibrium mixture is contacted with an alkanol of the formula R$_{10}$H, for example methanol if R$_{10}$ is methyl, until product 84 is formed. The reaction proceeds at a useful rate in a temperature range of 20°-30° C. but may also be carried out at lower or higher temperatures over a range up to +50° C. In alternate step "b" the starting materials are PGI$_2$ type compounds of formula 18. These, on contact with the appropriate alcohol R$_{10}$OH in the presence of an acid such as formic or acetic acid or Lewis acids such as boron trifluoride etherate, readily formed product 84 at 20°-30° C.

Group-VII Compounds

Chart 23 relates to 4-keto-PGI$_1$-type compounds. See U.S. Pat. No. 4,126,744, especially Columns 15–18. In step "a" a lactol of formula 85, readily available herein, is transformed to intermediate 86 by reaction with the anion of suitable phosphonate ester of formula 231. See W. S. Wadsworth and W. D. Emmons, J. Am. Chem. Soc., 83, 1733–1738 (1961). The anion, which is readily formed by treating the phosphonate with sodium hydride, reacts with lactol 85 at 0°-25° C.

In step "b", when X' is —CH—C(Hal)—, dehydrohalogenation yields —C≡C— at C$_{13}$-C$_{14}$. For example 86 is reacted with a base such as potassium t-butoxide.

In step "c", compound 88 is formed by desilylation, using selective hydrolysis as discussed herein for Chart 14.

In step "d", compound 89 is formed by oxidation of the C-2 hydroxymethyl group, using, for example, Jones reagent.

In step "e", compound 89 is deblocked in the usual manner, by mild acid hydrolysis, to yield the product 90.

Group-VIII Compounds

Chart 24 shows the steps for preparing these Δ$^6$-PGI$_1$-type compounds. See U.S. Pat. No. 4,128,713. The starting materials of formula 91 are available herein. It is preferred that esters be used and not the free acid form of the PGI$_2$-type starting material.

In step "a" the free hydroxyl groups of 91 are blocked with acyl groups. Aliphatic carboxyacylating agents useful for this transformation are known in the art or readily obtainable by methods known in the art, and include carboxyacyl halides, preferably chlorides, bromides, or fluorides, and carboxyacid anhydrides. The preferred reagent is an acid anhydride. Examples of acid anhydrides useful for this purpose are
acetic anhydride,
propionic anhydride,
butyric anhydride,
pentanoic anhydride,
nonanoic anhydride,
tridecanoic anhydride,
stearic anhydride,
(mono, di, or tri)chloroacetic anhydride,
3-chlorovaleric anhydride,
3-(2-bromoethyl)-4,8-dimethylnonanoic anhydride,
cyclopropaneacetic anhydride,
3-cycloheptanepropionic anhydride,
13-cyclopentanetridecanoic anhydride,
phenylacetic anhydride,
(2 or 3)-phenylpropionic anhydride,
13-phenyltridecanoic anhydride, and
phenoxyacetic anhydride.

In step "b" the formula-93 6-oxo intermediate is obtained from 92 by hydrolysis under mild acidic conditions, using for example dilute acetic acid in tetrahydrofuran.

In step "c" compound 94 is obtained on recyclizing 93 by heating at reflux in benzene or similar substantially non-polar aromatic solvent boiling above 50° C.

In step "d" compound 95 results on deblocking 94, for example by saponification with an alkali metal alkoxide. Any esters at $R_{18}$ are partially or completely converted to alkali metal salts.

In step "e" products 96 are formed by methods known in the art. For example sodium salts are converted to esters by the method of Mukaiyama, Chem. Letters 1975, 1045, employing N-methyl-2-bromopyridinium iodide.

Group-IX Compounds

Charts 25–27 relate to $\Delta^7$-PGI$_1$-type compounds and intermediates for their preparation. See U.S. Pat. No. 4,151,351. Final products of formula 115 exist as two isomers, 6α and 6β, and accordingly Chart 25 shows the preparation of 6β intermediates and Chart 26 shows corresponding 6α intermediates.

In Chart 25 the starting material 97, available herein, is transformed by nine steps to 106. In step "a", free hydroxyl groups are blocked, for example with THP.

In step "b", compound 99 is formed from 98 by phenylselenidylation, using methods known in the art. For example compound 98 is treated with n-butyllithium in hexane and diisopropylamine in tetrahydrofuran and then with phenylselenenyl chloride.

In step "c" oxidative deselenenylation with hydrogen peroxide yields 100.

In step "d" a second phenylselenidylation yields 101. For this purpose the reagent is prepared from diphenyl diselenide in an alcoholic solution of a borohydride reducing agent.

In step "e" lactol 102 is obtained in the usual way, for example by reduction with diisobutyl aluminum hydride at about −78° C.

In step "f" compound 103 is obtained by a Grignard reaction with a reagent of formula 232, added dropwise to a cold (0°–5° C.) solution of 102.

In step "g" compound 104 results from cyclizing 103 with an aryl or alkyl sulfonyl halide (e.g. p-toluenesulfonyl chloride) in an amine base.

In step "h" compound 105 is obtained by treatment with hydrogen peroxide as for step "c".

In step "i" the hydroxymethyl compound 106 is formed by hydroboration, for example using 9-borobicyclo-[3.3.1]nonane in an organic solvent at 0° C., followed by sodium hydroxide and hydrogen peroxide. See Fieser et al., Reagents for Organic Synthesis Vol. 2, p. 31, 1969, Wiley & Sons, N.Y.

In Chart 26 the starting material 99, available from step "b" of Chart 25, is transformed into the 6α isomer compound 111. In step "a", lactol 108 is formed by the usual methods of reducing a lactone, as in Chart 25, step "e".

In step "b", the Grignard reaction of Chart 25, step "f" is employed to yield compound 109.

In step "c" compound 110 results on cyclizing 109 by the procedure of Chart 25.

In step "d", actually two steps, oxidative deselenenylation forms the $\Delta^7$ unsaturation, and hydroboration forms the primary alcohol, as in Chart 25, steps "h" and "i", to yield 111.

Chart 27, using either 106 or 111 above, now represented as 112, shows the three steps to product 115. In step "a", compound 112 is deblocked, as by mild acid hydrolysis.

In step "b" the primary alcohol group is oxidized to carboxyl employing an Adams catalyst. See Fieser and Fieser, Reagents for Organic Synthesis, Vol 1, page 890, John Wiley & Sons, N.Y. (1967).

Finally in step "c" the carboxylic acid 114 is converted by the usual methods to yield compounds within the scope of 115. The stereochemistry at C-6 is preserved from 112 through the process steps at 115.

Group-X Compounds

Charts 28–31 relate to 6a-carba-PGI$_2$ compounds and intermediates for their preparation.

Chart 28 shows the steps from aldehyde 116 of Chart 29 to various intermediates 118, 119, 120, and 121 which, applying the prostaglandin numbering system, vary at the latent $C_{13}$–$C_{14}$ position in accordance with the definition of X.

In step "a" the Wittig reaction is employed using an ylid derived from a phosphonate of formula 233. In preparing 19-hydroxy end products having specific configuration at C-19 the appropriate optically active isomer of 233 is used. Preferably that isomer is used which yields an end product having highest pharmacological activity as determined by standard biological tests.

In step "b" the 3'-oxo group of 117 is reduced and all free hydroxyl groups are blocked with $R_{25}$ blocking groups to yield 118.

In step "c", compound 119 is obtained by photoisomerization whereby the latent $C_{13}$–$C_{14}$ double bond is isomerized from trans to cis. See for example U.S. Pat. No. 4,026,909. Compound 117 is irradiated, preferably with a photon generating source producing photons of wave length about 3500 Angstroms, until an equilibrium mixture of cis and trans isomers is obtained. The progress is conveniently monitored by thin layer chromatography. The mixture is then separated by conventional methods, for example silica gel chromatography. Thereafter the 3'-oxo groups are replaced by Q in the manner described above, and the hydroxyl groups are blocked with $R_{25}$.

In step "d", compound 120 is formed wherein there is a triple bond at latent $C_{13}$–$C_{14}$. The general procedure follows that of U.S. Pat. No. 4,029,681. A mono-halo compound is obtained by halogenation of 117 followed by dehydrohalogenation and dehalogenation. The halogenation is conveniently done with a reagent such as N-bromosuccinimide or alternatively, a solution of bromine in carbon tetrachloride. Dehydrohalogenation proceeds by addition of a base such as pyridine or methanolic sodium acetate. Dehalogenation is achieved with the usual reagents, for example zinc-acetic acid, to yield 120.

In step "e" compound 118 is reduced catalytically for example with hydrogen at atmospheric pressure over palladium on charcoal to yield 121.

The starting material of Chart 28, aldehyde 116, is obtained by the steps of Chart 29.

In Chart 29, the formula-122 tricyclic acetal ketone is known. See for example U.S. Pat. No. 3,873,571. Especially useful is the endo compound, named 3-(5,5-dimethyl-1,3-dioxolan-2-yl)tricyclo[4.2.0.0$^{2,4}$]octan-7-one. Epoxidation is achieved, applying the method of E. J. Corey et al., J. Am. Chem. Soc. 87, 1353 (1965). For this purpose dimethylsulfonium methylide is generated by reaction of sodio dimethylsulfinylcarbanide ("dimsyl") (prepared from dimethylsulfoxide and sodium hydride) and trimethylsulfonium iodide.

In step "a" the formula-123 epoxymethano compound is obtained by reaction of ketone 122 with the dimethylsulfonium methylide ylid. The reaction is carried out at about 0° C. and is completed within an hour.

In step "b" the cyclopentanone structure 124 is developed following a modification of the method of M. L. Leriverend et al., C.R. Acad. Sc. Paris, Series C, 280, 791 (1975). The product of step "a" is treated with lithium iodide in a solvent such as tetrahydrofuran at room temperature. Note in formula 124 that the carbonyl position on the ring is identified as C-8 for this as well as other tricyclic structures of formulas 125–129.

In step "c", consisting of two closely related steps, compound 124 is first reduced to the corresponding 8-hydroxy compounds, for example with a metal borohydride, especially sodium, potassium, lithium, or zinc borohydride. Other useful reducing agents are lithium-(tri-tert-butoxy)aluminum hydride, diisobutylaluminum hydride, and various borohydrides such as sodium trimethoxyborohydride. The resulting 8-hydroxy compounds, representing both α and β epimers, need not be separated. The mixture is next acylated to introduce the $R_{24}$ carboxyacyl blocking groups and thereby form compound 125.

$R_{24}$ may represent an aromatic group such as benzoyl, substituted benzoyl, mono-esterified phthaloyl, naphthoyl and substituted naphthoyl, or an aliphatic group such as acetyl or pivaloyl. For introducing those blocking groups, methods known in the art are used.

Thus, an aromatic acid of the formula $R_{24}OH$, wherein $R_{24}$ is an aromatic group within the scope of $R_{24}$ as defined above, for example benzoic acid, is reacted with the 8-hydroxy compound in the presence of a dehydrating agent, e.g. sulfuric acid, zinc chloride, or phosphoryl chloride; or an anhydride of the aromatic acid of the formula $(R_{24})_2O$, for example benzoic anhydride, is used. As examples of reagents providing $R_{24}$ for the purposes of this invention, the following are available as acids ($R_{24}OH$), anhydrides (($R_{24})_2O$), or acyl chlorides ($R_{24}Cl$):

benzoyl;
substituted benzoyl, e.g.
  (2-, 3-, or 4-)methylbenzoyl,
  (2-, 3-, or 4-)ethylbenzyl,
  (2-, 3-, or 4-)isopropylbenzoyl,
  (2-, 3-, or 4-)tert-butyl-benzoyl,
  2,4-dimethylbenzoyl,
  3,5-dimethylbenzoyl,
  2-isopropyltoluyl,
  2,4,6-trimethylbenzoyl,
  pentamethylbenzoyl,
  α-phenyl-(2-, 3-, or 4-)toluyl,
  (2-, 3-, or 4-)phenethylbenzoyl,
  (2-, 3-, or 4-)nitrobenzoyl,
  (2,4-, 2,5-, or 3,5-)dinitrobenzoyl,
  4,5-dimethyl-2-nitrobenzoyl,
  2-nitro-6-phenethylbenzoyl,
  3-nitro-2-phenethylbenzoyl;
mono-esterified phthaloyl, e.g.

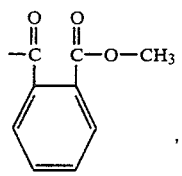

isophthaloyl, e.g.

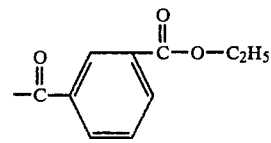

or terephthaloyl, e.g.

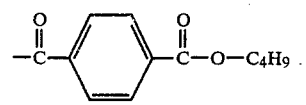

(1- or 2-)naphthoyl; and
substituted naphthoyl, e.g.
  (2-, 3-, 4-, 5-, 6-, or 7-)-methyl-1-naphthoyl,
  (2- or 4-)-ethyl-1-naphthoyl,
  2-isopropyl-1-naphthoyl,
  4,5-dimethyl-1-naphthoyl,
  6-isopropyl-4-methyl-1-naphthoyl,
  8-benzyl-1-naphthoyl,
  (3-, 4-, 5-, or 8-)-nitro-1-naphthoyl,
  4,5-dinitro-1-naphthoyl,
  (3-, 4-, 6-, 7- or 8-)-methyl-1-naphthoyl,
  4-ethyl-2-naphthoyl, and
  (5- or 8-)-nitro-2-naphthoyl.

Examples of aromatic acid anhydrides useful for this purpose are
  benzoic anhydride,
  (o, m, or p)-bromobenzoic anhydride,
  2,4-(or 3,4)-dichlorobenzoic anhydride,
  p-trifluoromethylbenzoic anhydride,
  2-chloro-3-nitrobenzoic anhydride,
  (o, m, or p)-nitrobenzoic anhydride,
  (o, m, or p)-toluic anhydride,
  4-methyl-3-nitrobenzoic anhydride,
  4-octylbenzoic anhydride,
  (2,3, or 4)-biphenylcarboxylic anhydride,
  3-chloro-4-biphenylcarboxylic anhydride,
  5-isopropyl-6-nitro-3-biphenylcarboxylic anhydride, and
  (1 or 2)-naphthoic anhydride.

Preferably, however, an aromatic acyl halide, for example benzoyl chloride, is reacted with the 8-hydroxy compound in the presence of a tertiary amine such as pyridine, triethylamine, and the like. The reaction is carried out under a variety of conditions using procedures generally known in the art. Generally, mild conditions are employed, e.g. 20°-60° C., contacting the reactants in a liquid medium, e.g. excess pyridine or an inert solvent such as benzene, toluene or chloroform. The acylating agent is used either in stoichiometric amount or in excess. There may be employed, therefore, benzoyl chloride, 4-nitrobenzoyl chloride, 3,5-dinitrobenzoyl chloride, and the like, i.e. $R_{24}Cl$ compounds corresponding to the above $R_{24}$ groups. If the acyl chloride is not available, it is made from the corresponding acid and phosphorus pentachloride as is known in the art.

Use of aliphatic carboxyacylating agents such as acetic anhydride was described above for Chart 24.

In step "d", aldehyde 126 is obtained from 125 by hydrolysis of the acetal. For this purpose an acid such as aqueous formic acid is used at about 0° C.

In step "e" the Wittig reaction is employed to introduce the prospective side chain $R_{29}$. For general information on the Wittig reaction see, for example, A. W. Johnson, "Ylid Chemistry", Academic Press, N.Y., 1966. If $R_{29}$ is n-pentyl, the ylid is prepared from n-hexyltriphenylphosphonium bromide. Since $R_{29}$ is sacrificed in forming aldehyde 116, it is preferred that $R_{29}$ be pentyl or even shorter alkyl of 3–7 carbon atoms. The ylids are conveniently made using n-butyllithium.

Following the Wittig reaction, the $R_{24}$ acyl blocking groups are removed to form the formula-127 compounds. Here, as for step (d) of Chart 24, a base in a hydroxylic medium is useful.

In step "f" the 8-oxo formula-128 compound is formed by oxidation. For this the Jones reagent is useful. See J. Chem. Soc. p. 39 (1946). Another useful reagent for this purpose is the Collins, e.g., chromium trioxide in pyridine. See J. C. Collins et al., Tetrahedron Lett., 3363 (1968). Dichloromethane is a suitable diluent for this purpose. Reaction temperatures of below 30° C. should be used. Preferred reaction temperatures are in the range 0° to +30° C. The oxidation proceeds rapidly and is usually complete in about 5 to 20 minutes.

In step "g" alkene 128 is hydroxylated to glycol 129. For this purpose osmium tetroxide is a suitable reagent, for example in conjunction with N-methylmorpholine oxide dihydrate complex. See Fieser et al., "Reagents for Organic Synthesis" (Vol. 1), p. 690, John Wiley & Sons, Inc., New York (1967).

In step "h", several methods are available for obtaining the formula-130 intermediate. In one method, the glycol is converted to a bis(alkanesulfonic acid) ester and subsequently hydrolyzed to 130 by methods known in the art (see, for example German Offenlegungsschrift No. 1,937,676, Derwent Farmdoc 6862R); see also U.S. Pat. No. 3,843,712. Another method is by way of a diformate by formolysis of the glycol; see U.S. Pat. No. 3,873,571.

A preferred method is by way of a cyclic ortho ester. For this purpose, glycol 129 is reacted with an ortho ester of formula 234. There is then formed a cyclic ortho ester of formula 235. The reaction goes smoothly in a temperature range of −50° C. to +100° C., although for convenience 0° C. to +50° C. is generally preferred. From 1.5 to 10 molar equivalents of the ortho ester are employed, together with an acid catalyst. The amount of the catalyst is usually a small fraction of the weight of the glycol, say 1%, and typical catalysts include pyridine hydrochloride, formic acid, hydrogen chloride, p-toluenesulfonic acid, trichloroacetic acid, or trifluoroaceticacid. The reaction is preferably run in a solvent, for example benzene, dichloromethane, ethyl acetate, or diethyl ether. It is generally completed within a few minutes and is conveniently followed by TLC (thin layer chromatography on basic silica gel plates).

The ortho ester reagents are known in the art or readily available by methods known in the art. See for example S. M. McElvain et al., J. Am. Chem. Soc. 64, 1925 (1942), starting with an appropriate nitrile. Examples of useful ortho esters include:
trimethyl orthoformate,
trimethyl orthoacetate,
trimethyl orthopropionate, and
trimethyl orthobutyrate.

Next, the cyclic orthoester 235 is reacted with anhydrous formic acid to yield a diol diester of formula 236.

By "anhydrous formic acid" is meant that it contains not more than 0.5% water. The reaction is run with an excess of formic acid, which may itself serve as the solvent for the reaction. Solvents may be present, for example dichloromethane, benzene, or diethyl ether, usually not over 20% by volume of the formic acid. There may also be present organic acid anhydrides, for example acetic anhydride, or alkyl ortho-esters, for example trimethyl orthoformate, which are useful as drying agents for the formic acid. Although the reaction proceeds over a wide range of temperatures, it is conveniently run at about 20°–30° C. and is usually completed within about 10 minutes.

Next, the diol diester 236 is converted to intermediate 130 by methods known in the art, for example by hydrolysis in the presence of a base in an alcoholic medium. Examples of the base are sodium or potassium carbonate or sodium or potassium alkoxides including methoxides or ethoxides. The reaction is conveniently run in an excess of the solvolysis reagent, for example methanol or ethanol. The temperature range is from −50° C. to 100° C. The time for completion of the reaction varies with the nature of $R_{30}$ and the base, proceeding in the case of alkali carbonates in a few minutes when $R_{30}$ is hydrogen but taking up to several hours when $R_{30}$ is ethyl, for example.

The bicyclic compounds of formulas 130–134, as well as 116, are named as pentalene derivatives, for example compound 130 is a 4-substituted 5-hydroxy-pentalen-2-one.

In step "i" the C-5 -hydroxyl of compound 130 is optionally transformed to C-5 deoxy using mesylation and mesylate reduction as shown in more detail in Chart 30.

In step "j" $R_9$ and $Q_5$ are blocked with silyl blocking groups to form 132.

In step "k" compound 132 is reduced to 2-hydroxy compounds as discussed above for step "c" to form 133.

In step "l" the mixed 2-hydroxy compounds are acylated as above for step "c" to form 134.

In step "m" compound 116 is obtained by subjecting compound 134 to ozonolysis using methods known in the art; see Fieser and Fieser, Reagents for Organic Synthesis, Vol. 1, pp. 773–777, John Wiley, N.Y. (1967).

Chart 30 shows the steps in preparing 5-deoxy pentalen-2-ones useful as intermediates in preparing 11-deoxy prostacyclin analogs within the scope of Group X. The starting materials of formula 135 are available from the processes of Chart 28.

In step "a", the C-5 position is deblocked by desilylation.

In step "b", product 136 of step "a" is mesylated to form the 5-mesylate of formula 137. Methanesulfonyl chloride, $CH_3SO_2Cl$, is preferred for this reaction, in the presence of a base such as pyridine, dimethylaniline, or other tertiary amine. The reaction is carried out at about 0° to 25° C. Alternatively, tosyl (p-toluenesulfonyl) groups may be used and applied as known in the art. See U.S. Pat. No. 4,033,989, column 135.

In step "c", the mesylate (or tosylate) group is cleaved by methods known in the art. Reducing agents may be used, including metal borohydrides (such as sodium borohydride) metal cyanoborohydrides (such as sodium cyanoborohydride) or an aluminum hydride (such as sodium aluminum hydride) in an aprotic solvent (such as dimethyl sulfoxide or diethyl ether). For other methods see U.S. Pat. No. 4,033,989, column 79. The C-2 position is deblocked in this step.

In step "d", the formula 139 pentalen-2-one is obtained on oxidation.

Finally in step "e" the side-chain is deblocked by mild acid hydrolysis to yield the formula-140 compounds.

The 6a-carba-prostacyclin compounds of formula 237 comprising Group X are obtained by applying known methods to the compounds of formula 149 and 150 of Chart 31.

Chart 31 illustrates the process of starting with a compound of formula 141 and
(1) transforming it to a compound of formula 142,
(2) reacting that compound with the carbanion of a sulfoximine of formula 238 to form a compound of formula 143,
(3) subjecting that formula-143 compound to reductive elimination to form a compound of formula 144,
(4) preferentially removing silyl groups $-Si(R_{17})_3$ from the formula-144 compound to form a compound of formula 145,
(5) acylating the formula-145 compound to form a compound of formula 146,
(6) transforming the formula-146 compound to a compound of formula 147,
(7) optionally separating the C-5 isomers of the formula-147 compound,
(8) oxidizing the formula-147 compound to form a compound of formula 148, and
(9) deacylating to form the C-5 isomers represented by formulas 149 and 150.

The pentalene structures of formula 141 and 142 use the same numbering of carbon atoms as for formula 135. Compounds of formulas 143–150 bearing an upper side chain follow prostacyclin numbering.

In Chart 31, the formula-141 starting materials are available by further treatment of 118–121 of Chart 28. Compounds 118–121 are deacylated, for example in mild base, to convert $-OR_{24}$ to $-OH$. Oxidation then yields the corresponding pentalen-2-ones which are deblocked in mild acid hydrolysis. Formula 141 includes formula-140 compounds of Chart 30.

In step "a" the formula-141 compounds are silylated by procedures described herein. It is preferred that $R_{17}$ groups be hindered alkyl groups, for example t-butyldimethyl.

In step "b" the formula-143 sulfonimidoyl adducts are obtained by addition of a carbanion of a sulfoximine. For background on this reaction see C. R. Johnson et al., J. Am. Chem. Soc. 95, 6462 (1973). Here the sulfoximine is represented by formula 238 and is readily synthesized by methods disclosed hereinafter or known in the art. The carbanion is generated by reacting the sulfoximine with any of the usual reagents which will extract an active hydrogen from such sulfoximines, for example, an alkyllithium or an alkylmagnesium halide. One molecular equivalent of the hydrogen-extracting reagent is used for each equivalent of sulfoximine. In the adduct formation with the formula-142 silylated ketone, the sulfoximine is preferably used in excess, in a range of 1.2 to 3.0 molecular equivalents of sulfoximine per equivalent of ketone.

The reaction is carried out in the range of about 0° C. to about $-78°$ C., preferably 0° to $-40°$, in an inert reaction diluent such as tetrahydrofuran. In this reaction competing carbonyl groups on either compound 142 or the solvent molecules are undesired.

In step "c" the formula-144 intermediates are obtained by reductive elimination by contacting the formula-143 adduct with aluminum amalgam (cf. Johnson et al., cited above) in the presence of aqueous acetic acid or other carboxylic acid such as propionic acid, butyric acid, or citric acid. Mineral acid, such as hydrochloric acid, are also useful for this purpose. The ratio of reactants is not critical, however, it is preferred to use a large excess of aluminum amalgam and acid. Also, a sufficient quantity of a water-miscible inert organic liquid diluent is used to provide a mobile reaction mixture. A temperature range of about 0° C. to about 50° C., preferably about 20°–30°, is useful. The mixed C-5 (E) and (Z) isomers are obtained as a mixture.

In step "d" the silyl groups of the formula-144 intermediates are replaced with hydrogen to yield the formula-145 compounds. For this desilylation, reagents and conditions are selected which will not deblock the C-1 ethers. For unhindered silyl groups a base such as an alkali metal carbonate in dioxane or tetrahydrofuran is useful in a temperature range of about $-10°$ to $+100°$ C. Preferably, the silyl groups are t-butyldimethylsilyl, in which case their removal is done with tetrabutylammonium fluoride. See Corey et al., J. Am. Chem. Soc. 94, 6190 (1972).

In step "e" the formula-146 compounds are obtained from the formula-145 compounds above by blocking free hydroxyls with $R_{24}$ carboxyacyl groups. For example, $R_{24}$ may represent an aromatic group such as benzoyl, substituted benzoyl, mono-esterified phthaloyl, naphthyl and substituted naphthoyl, or an aliphatic group such as acetyl or pivaloyl. For introducing those blocking groups, methods known in the art or disclosed herein are used.

In step "f" the formula-146 compounds are deblocked at C-1 to yield the formula-147 alcohols. For this purpose methods known in the art are used, for example mild acid hydrolysis for these tetrahydropyranyl or similar ether-bonded $R_{25}$ groups, using dilute acetic acid, aqueous citric acid, or aqueous phosphoric acid in a mutual solvent such as tetrahydrofuran. Temperatures in the range of 25°–55° C. may be employed.

The C-5 (E) and (Z) isomers are preferably separated at this stage, for example by chromatographing the formula-147 compounds. For this purpose a silica gel column is useful, preferably a high pressure liquid column using silica gel with a mean particle diameter of 40 microns. For background on HPLC (high pressure liquid chromatography) see for example "Modern Practice of Liquid Chromatography", J. J. Kirkland, editor, Wiley Interscience, N.Y., 1971. Optionally the compounds of formula 144, 145, 146, or 148 may be chromatographed to yield the respective (5E) and (5Z) isomers.

In step "g" the formula-148 compounds are obtained from either the now-separated (5E) and (5Z) isomers or the mixed isomers of formula 147 by oxidation. Reagents useful for this transformation are known to the art. An especially useful reagent for this purpose is the Jones reagent, i.e., acidified chromic acid. See J. Chem. Soc. 39 (1946). Acetone is a suitable diluent for this purpose, and a slight excess beyond the amount necessary to oxidize the hydroxy groups of the reactant is used. Reaction temperatures at least as low as about 0° C. should be used. Preferred reaction temperatures are in the range −10° to −50° C. The oxidation proceeds rapidly and is usually complete in about 5 to 20 minutes. The excess oxidant is destroyed, for example by addition of a lower alkanol, advantageously, isopropyl alcohol, and the formula-148 product is isolated by conventional methods.

Finally, in step "h" the formula-149 products are obtained by deblocking the $R_{24}$ carboxyacyl groups, i.e. by decarboxyacylation, for example with a base such as potassium hydroxide or carbonate in methanol or methanol-water at about 25° C.

During the transformations of Chart 31 the stereoconfiguration at C-8, C-9, C-11 and C-15 is unchanged. For example, a formula-149 product with 11α-hydroxy groups is obtained from starting material 141 having 11-α hydroxy groups. Likewise the entire moiety represented by

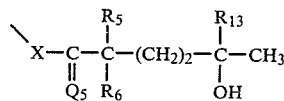

is preserved intact, so that a 15S product is obtained from a 15S starting material.

Charts 32-45, herein, relate to intermediates and serve as guides for the process steps for the Preparations herein, discussed below.

Compounds of formulas 4 or 15 which are not specifically illustrated or exemplified herein are obtained by transformations using chemical processes disclosed herein or known to those skilled in the art.

For example the transformation of $R_4$ in Q from hydrogen to methyl at C-15 requires the intermediate 15-oxo compound prepared by oxidation, followed by alkylation with Grignard $CH_3MgHal$ or trimethylaluminum, and subsequent separation of the 15α and 15β products, for example by chromatography, preferably of the methyl esters. Preparation of esters and salts and various modifications at C-1, e.g., amides and sulfonamides follow the general procedures discussed herein and known in the art.

It should be understood that many of the intermediates disclosed herein are useful not only for the purposes shown but also for many of the above transformations as known in the art.

The products formed from each step of the process are often mixtures, and, as known to one skilled in the art, may be used as such for a succeeding step or, optionally, separated and purified by conventional methods of fractionation, liquid extraction, and the like, before proceeding. It is intended that compounds are claimed out only in their purified form but also in mixtures, for example the formula-4 19-hydroxy compounds in their mixed (R,S) form.

DESCRIPTION OF THE PREFERRED EMBODIMENTS

The invention is further illustrated by, but not limited to, the following examples.

All temperatures are in degrees centigrade.

Infrared absorption spectra are recorded on a Perkin-Elmer model 421 infrared spectrophotometer. Except when specified otherwise, undiluted (neat) samples are used.

The NMR spectra are recorded on a Varian A-60, A-60D, T-60 or XL-100 spectrophotometer in deuterochloroform solution with tetramethylsilane as an internal standard.

Mass spectra are recorded on a Varian Model MAT CH7 Mass Spectrometer, a CEC Model 110B Double Focusing High Resolution Mass Spectrometer, or a LKB Model 9000 Gas Chromatograph-Mass Spectrometer (ionization voltage 22 or 70 ev.), and samples are usually run as TMS (trimethylsilyl) derivatives.

"Brine", herein, refers to an aqueous saturated sodium chloride solution.

"Celite R" is a calcium aluminosilicate, useful as a filter aid.

"Collins reagent" is chromium trioxide in pyridine. See Tetrahedron Lett. p. 3363 (1968).

"DIBAL", herein, refers to diisobutylaluminum hydride.

"Florisil R", herein, is a chromatographic magnesium silicate produced by the Floridin Co. See Fieser et al., "Reagents for Organic Synthesis" p. 393 John Wiley and Sons, Inc., New York, N.Y. (1967).

"HPLC", herein, refers to high pressure liquid chromatography.

"Jones reagent" is chromic acid, see J. Chem. Soc. p. 39 (1946).

"$R_f$" herein, refers to the measurement, in thin layer chromatography, of the movement of the sample spot relative to that of the solvent front, on silica gel plates unless specified, and in a solvent system that is identified.

"Skellysolve B", herein, refers to mixed isomeric hexanes.

"THP", herein, refers to tetrahydropyran-2-yl.

"TLC", herein, refers to thin layer chromatography.

"Concentrating", as used herein, refers to concentration under reduced pressure, preferably at less than 50 mm. and at temperatures below 35° C.

"Drying", as used herein, refers to contacting a compound, in solution, with an anhydrous agent such as sodium sulfate or magnesium sulfate to remove water and filtering to remove solids.

Silica gel chromatography, as used herein, is understood to include elution, collection of fractions, and combination of those fractions shown by TLC to contain the desired product free of starting materials and impurities.

The A-IX solvent system used in thin layer chromatography is made up from ethyl acetate-acetic acid-2,2,4-trimethylpentane-water (90:20:50:100) according to M. Hamberg and B. Samuelsson, J. Biol. Chem. 241, 247 (1966).

Preparation 1

5α-Hydroxy-3α-tetrahydropyran-2-yloxy-2β-(trans-2-formylethenyl)-1α-cyclopentaneacetic Acid, γ-Lactone (Formula 158 of Chart 32)

Refer to Chart 32. The title compound is obtained in seven steps starting with the formula-151 tricyclic lactone aldehyde, for which see U.S. Pat. No. 3,816,462.

a. Exo-3-hydroxy-endo-6-vinyl-bicyclo[3.1.0]-hexanexo-2-acetic acid, γ-lactone (Formula 152). A solution of the formula-151 tricyclic lactone aldehyde (20 g.) in 150 ml. of benzene is treated at 5°–10° C. with a solution of the ylid prepared from methyltriphenylphosphonium bromide (54 g.) and 95 ml. of 1.6 M butyllithium in one liter of benzene (previously heated at reflux for one hr. and cooled). The addition is completed within 1–1.5 hr., and, after an additional 0.5 hr. stirring, the mixture is filtered and concentrated. The residue is taken up in 100–200 ml. of ethyl acetate-Skellysolve B (40:60) and left standing to crystallize out the by-product triphenylphosphine oxide. After filtration, the filtrate is subjected to silica gel chromatography, eluting with ethyl acetate-Skellysolve B (40:60). There is obtained the formula-152 compound, 16.2 g., an oil, having NMR peaks at 1.3–3.0, 4.6–4.9, and 5.0–5.4 δ; and $R_f$ 0.74 (in ethyl acetate-Skellysolve B (50—50)).

b. Endo-6-(1,2-dihydroxyethyl)-exo-3-hydroxy-bicyclo[3.1.0]-hexen-exo-2-acetic acid, 3-lactone (Formula 153). A solution of the formula-152 alkene (step a, 8.0 g.) in 80 ml. of acetone is treated with a solution of N-methylmorpholine oxide dihydrate (9.0 g.) in 12 ml. of water, followed by a solution of osmium tetroxide (130 mg.) in 6.5 ml. of t-butanol. When the reaction is completed, the acetone is removed under reduced pressure. The residue is diluted with 100 ml. of water, saturated with ammonium sulfate, and extracted with tetrahydrofuran. The organic phase is dried over magnesium sulfate and concentrated under reduced pressure to yield 12 g. of crude oily product. The oil is subjected to silica gel chromatography to yield the formula-153 compound, 8.5 g., an oil, having NMR peaks at 0.7–1.2, 1.3–1.9, 2.4–3.4, 3.4–3.7, 3.7–4.2, and 4.7–5.0 δ; $R_f$ 0.66 (in methanoldichloromethane (15:85)).

c. 3α-Formyloxy-5α-hydroxy-2β-(3-propionyloxy-trans-1-propenyl)-1α-cyclopentaneacetic acid, γ-lactone (Formula 154). A solution of the formula-153 glycol (step b, 7.2 g.) and triethyl orthopropionate (15 g.) in 30 ml. of tetrahydrofuran is treated with 3 μl of trifluoroacetic acid. After one hr. the solvent is removed under reduced pressure and the residue treated with 100 ml. of anhydrous formic acid with stirring. After 15 min. there is added 100 ml. of 1 N. sodium hydroxide and 100 ml. of crushed ice. The mixture is extracted with dichloromethane and the organic phase is washed with 5% aqueous sodium bicarbonate, dried over magnesium sulfate, and concentrated. The oil (9.6 g.) thus obtained is subjected to silica gel chromatography, eluting with ethyl acetatecyclohexane (1:1), to yield the formula-154 compound, 4.1 g., having NMR peaks at 1.1, 1.9–3.0, 4.4–4.6, 4.8–5.2, 5.6–5.8, and 8.0 δ; and $R_f$ 0.49 (in ethyl acetate-cyclohexane (1:1)).

d. 3α,5α-Dihydroxy-2β-(3-propionyloxy-trans-1-propenyl)-1α-cyclopentaneacetic acid, γ-lactone (Formula 155). A solution of the formula-154 formate (step c, 4.1 g.) in 35 ml. of dry methanol is treated with sodium bicarbonate (0.5 g.). When the reaction is finished in about 2–3 hr., the solvent is removed under reduced pressure. The residue is partitioned between water and dichloromethane, and the organic phase is dried over magnesium sulfate and concentrated. The oily residue is subjected to silica gel chromatography, eluting with ethyl acetate to yield the formula-155 compound, 2.8 g., having NMR peaks at 1.13, 3.7–4.3, 4.3–4.7, 4.7–5.2, and 5.5–5.8 δ; and $R_f$ 0.65 (in ethyl acetate).

e. 3α-Tetrahydropyran-2-yloxy-5α-hydroxy-2δ-(3-propionyloxy-trans-1-propenyl)-1α-cyclopentaneacetic acid, γ-lactone (Formula-156). A solution of the formula-155 5-hydroxy lactone (step d, 2.8 g.) in 10 ml. of dichloromethane is treated with 5 ml. of dihydropyran and 5 mg. of p-toluenesulfonic acid dissolved in 1 ml. of tetrahydrofuran. After the reaction is finished, in about 0.5 hr., the mixture is washed with 5% aqueous sodium bicarbonate. The organic phase is dried over sodium sulfate and concentrated. The residue is subjected to silica gel chromatography, eluting with ethyl acetate-Skellysolve B (60:40) to yield the formula-156 compound.

f. 3α-Tetrahydropyran-2-yloxy-5α-hydroxy-2β-(3-hydroxy-trans-1-propenyl)-1α-cyclopentaneacetic acid, γ-lactone (Formula-157). The formula-156 propionate, (step e, 3.0 g.) in 10 ml. of methanol is added to a solution of sodium methoxide (freshly prepared from 20 mg. of sodium in 40 ml. of anhydrous methanol). After the reaction is complete, in about 20 min., the methanol is remove under reduced pressure. The residue is partitioned between dichloromethane and 0.4 M phosphate buffer of pH 4.5. The organic phase is dried over sodium sulfate and concentrated to yield the formula-157 compound.

g. 3α-Tetrahydropyran-2-yloxy-5α-hydroxy-2β-(trans-2-formylethenyl)-1α-cyclopentaneacetic acid, γ-lactone (Formula 158). An oxidizing reagent is prepared from chromium trioxide (5.4 g.) and 3,5-dimethylpyrazole (5.2 g.) in 150 ml. of dichloromethane, stirred for 15 min. To the solution is then added the formula-157 3-hydroxy compound (step f, 1.8 l g.) dissolved in 20 ml. of dichloromethane. After the reaction is finished, in about 5 min., the mixture is washed with 5% aqueous bicarbonate. The organic phase is dried over sodium sulfate and concentrated. The residue is subjected to silica gel chromatography, eluting with acetone-dichloromethane (1:9) to yield the formula-158 compound.

Preparation 19,20-Didehydro (or "Δ19")-PGF$_{2\alpha}$, 11,15-bis(tetrahydropyran-2-yl Ether), Methyl Ester a. There is first prepared 3α,5α-dihydroxy-2β-[(3R,S)-3-hydroxy-trans-1,7-octadienyl]-1α-cyclopentaneacetic acid γ-lactone, 3,3'-bis-tetrahydropyran-2-yl-ether).

A solution of 5α-hydroxy-3α-tetrahydropyran-2-yloxy-2β-(trans-2-formylethenyl)-1α-cyclopentaneacetic acid, γ-lactone (2.775 g., Preparation 1) in 40 ml. of diethyl ether and 10 ml. of tetrahydrofuran is treated at −70° C. with 1-pentenylmagnesium bromide (prepared from 5-bromo-1-pentene (4.115 g.) and magnesium (0.667 g.) in 40 ml. of diethyl ether) added dropwise over 17 min. The mixture is then stirred at about −60° C. for 22 min. and quenched with saturated aqueous ammonium chloride. Sodium sulfate powder is added for coagulation and the solids filtered off. The filtrate, together with ether washings, is dried and concentrated to an oil, 3.109 g. The product is chromatographed, eluting with methylene chloride-acetone (6:1) to obtain the mono-THP ether, mixed C-15 epimers, 2.427 g., having R$_f$ 0.34 and 0.29 (in methylene chloride-acetone (4:1)), NMR peaks at 6.20–5.4, 5.2–4.78, 4.68, 4.3–3.2, 3.02–2.4, 2.35–1.85, and 1.8–1.2 δ, infrared absorption at 3450, 2995, 1775, 1200, 1180, 1120, 1075, 1030, 1020, 975, 920, 870, and 815 cm$^{-1}$, and mass spectral lines at 422.2446, 407, 353, 337, 321, 320, 269, 251, and 85.

The above mono-THP ether is treated in methylene chloride solution with excess dihydropyran in the presence of pyridine hydrochloride at about 25° C. for 16 hr. The mixture is diluted with about 300 ml. of methylene chloride and washed with 5% aqueous sodium bicarbonate, water, and brine, and dried. Concentration yields the bis-THP ether compound, viz. 3α,5α-dihydroxy-2β-[(3R,S) 3-hydroxy-trans-1,7-octadienyl]-1α-cyclopentaneacetic acid γ-lactone, 3,3'-bis(tetrahydropyran-2-yl) ether).

b. The corresponding lactol is then prepared. The lactone of part "a" (9.82 g.) is treated in 100 ml. of toluene at −68° C. with diisobutylaluminum hydride (DIBAL) (22.65 ml. of 1.5 M. toluene solution) added dropwise over 8 min. The mixture is stirred at −75° for one hr. and then 10 ml. of saturated aqueous sodium sulfate added. The mixture is warmed to room temperature, diluted with 700 ml. of diethyl ether, and treated with powdered sodium sulfate. The solids are removed on a Celite ® filter. The filtrate is dried and concentrated to yield the lactol compound, having R$_f$ 0.35 (in acetone-methylene chloride (1:6)).

c. There is prepared 19,20-didehydro (or "Δ19")-PGF$_{2\alpha}$, 11,15-bis(tetrahydropyran-2-yl ether) and its methyl ester. The lactol of Example 2 (9.87 g.) is alkylated by the Wittig reaction. The Wittig reagent is first prepared from 4-carboxybutyl triphenylphosphonium bromide (35.1 g.) added to the reaction product of sodium hydride (7.6 g.) and 180 ml. of dimethyl sulfoxide previously warmed to 70°–75° C. for 1.5 hr. and then cooled to about 25° C. for 25 min., then treated with the (3S) lactol in 65 ml. of dimethylsulfoxide added dropwise over 25 min. and stirred additional 30 min. The mixture is acidified in ice water with 2 N potassium hydrogen sulfate and then extracted with ether. The organic phase is washed with brine, dried, and concentrated to yield the bis-THP free acid.

The acid is then esterified with ethereal diazomethane and the resulting methyl ester is chromatographed to yield the title methyl ester 9.37 g., having R$_f$ 0.62 (in acetone-methylene chloride (1:6)), and NMR peaks at 6.18–4.56, 4.37–3.20, 3.65, and 2.78–1.11 δ.

Preparation 3

(19R)-19-Hydroxy-PGF$_{2\alpha}$ and its (19S) epimer (Formula 172 of Chart 35)

Refer to Charts 33, 34, and 35. Following the procedures of J.C. Sih, Prostaglandins Vol. 13, No. 5, 831-835 (1977), the title (19R) compound is obtained.

Likewise following those procedures but substituting the Grignard reagent prepared from the THP-blocked bromide obtained from (S)-(+)-1-penten-4-ol for the Grignard reagent prepared from the THP-blocked bromide obtained from (R)-(−)-1-penten-4-ol, there is obtained the corresponding (19S) epimer.

Likewise using the dl-1-penten-4-ol, the (19RS) product is obtained.

Further, the corresponding PGE$_2$ compounds are obtained by oxidizing the formula-171 blocked PGF$_{2\alpha}$ compounds and then deblocking to yield the formula-174 compounds.

In Chart 33 are also shown steps leading to 15-deoxy lactones of formula 163 by mesylating at C-15, followed by demesylation as described herein.

In Chart 34 are shown steps utilizing chemistry known in the art leading to the C$_{13}$–C$_{14}$ modifications of the lactones of formulas 166, 167, 168, and 169, which taken together are embodied in formula 170 of Chart 35.

Preparation 4

2-Decarboxy-2-hydroxymethyl-19ξ-hydroxy-PGF$_{2\alpha}$ and -PGE$_2$. (Formula 179 and 182, respectively, of Chart 36)

Refer to Chart 36. Starting with 19ξ-hydroxy-PGF$_{2\alpha}$, methyl ester, the title PGF compound is obtained on reduction with lithium aluminum hydride.

Thereafter, the blocking at C-1 and C-19, the C-9 hydroxy is oxidized and the blocking groups removed to yield the PGE title compound.

Preparation 5

19ξ-Hydroxy-PGF$_{2\alpha}$, Amide (Formula 185 of Chart 37)

Refer to Chart 37. The mixed anhydride is first prepared. A solution of 19ξ-hydroxy-PGF$_{2\alpha}$ in methylene chloride is treated with triethylamine (2 equiv.) and isobutylchloroformate (1.01 equiv.) at about 25° C. for 0.5 hr. There is then added at about −5° C., a saturated solution of ammonia in acetonitrile and the mixture stirred at −5° C. for 10 min. The reaction mixture is diluted with brine and water (5:1) and extracted with ether. The organic phase is washed with brine and 2 N hydrochloric acid, then with brine and 5% sodium bicarbonate, finally with brine, dried and concentrated. The residue is chromatographed on a HPLC silica gel column, eluting with acetone to yield the title compound.

Preparation 6

2-Decarboxy-2-aminomethyl-19ξ-hydroxy-PGF$_{2\alpha}$ (Formula 186 of Chart 37)

Refer to Chart 37. Following the procedure of U.S. Pat. No. 4,085,139, Example 3B, the 19ξ-hydroxy-PGF$_{2\alpha}$ amide (Preparation 5) is treated with lithium aluminum hydride in tetrahydrofuran at about 25° C. for 48 hr. to yield the title compound.

Preparation 7

19ξ-Hydroxy-PGF$_{2\alpha}$, Methanesulfonamide

Refer to Chart 38. A solution of mixed anhydride in dimethylformamide (step "a" of Chart 37, Preparation 5) is treated, with stirring, at 0° C. with about 4 equivalents of methanesulfonamide sodium salt (prepared from methanesulfonamide and methanolic sodium methoxide in methanol, concentrating and azeotroping with benzene), thereafter adding sufficient hexamethylphosphoramide to insure a homogeneous mixture. The mixture is stirred at about 25° C. for 16 hr., then acidified with cold dilute hydrochloric acid and extracted with ethyl acetate. The organic phase is washed with water and brine, dried, and concentrated. The residue is chromatographed on silica gel, eluting with methanol-methylene chloride, to yield the title compound.

Preparation 8

2-Decarboxy-2-(1H-tetrazol-5-yl)-19ξ-hydroxy-PGF$_{2\alpha}$ (Formula 197, Chart 40)

Refer to Chart 40. The formula-193 amide is transformed to the formula-194 nitrile by reaction with N,N'-dicyclohexylcarbodiimide (DCC) to pyridine at about 25° C. The precipitated dicyclohexylurea is removed by filtration and the filtrate is concentrated to the formula-194 nitrile.

The formula-195 tetrazolyl compound is obtained from the above nitrile by reaction with sodium azide and ammonium chloride in dimethylformamide at about 115° C. When the reaction is finished as shown by TLC, the mixture is cooled and concentrated. The residue is taken up in chloroform, washed with brine, dried, and concentrated to the formula-195 compound. Thereafter deblocking removes silyl groups and THP or other blocking groups to yield the title product.

Chart 39 shows an alternative process applying the Wittig reaction and utilizing an ylid prepared from a phosphonium compound of formula 239. See U.S. Pat. No. 3,928,391. The starting material of formula 190 is obtained from any of the lactones represented by formula 170 by reduction as known in the art for example see J. C. Sih, Prostaglandins 13, 831-5 (1977).

Preparation 9

19-Hydroxy-19-methyl-PGF$_{2\alpha}$ (Formula 203 of Chart 41) and -PGE$_2$ (Formula 205)

Refer to Chart 41.

a. 3α,5α-Dihydroxy-2β-[(3RS)-3-hydroxy-7-oxo-trans-1-octenyl]-1α-cyclopentaneacetic Acid γ-Lactone, 3,3'-bis-(Tetrahydropyran-2-yl Ether) (Formula 199).

The formula-198 7-hydroxy lactone (10.02 g.) in 300 ml. of acetone is treated at −30° C. with Jones reagent (14.95 ml. of 2.67 M) added dropwise within 10 min. The mixture is stirred at −25° to −20° C. for additional 18 min., then quenched with 20 ml. of isopropanol and stirred 5 min. more. The mixture is added to 500 ml. of cold 5% sodium bicarbonate and 800 ml. of ethyl acetate, separated, and the organic phase is combined with ether extracts of the aqueous phase. The organic phase is washed with 5% sodium bicarbonate, ice water, and brine, dried, and concentrated to yield the title compound, 9.93 g., having R$_f$ 0.64 (TLC on silica gel in acetone-methylene chloride (1:3), and NMR peaks at 5.50, 5.00, 4.63, 4.25-3.0), 2.13, and 3.00-1.20 δ.

b. 3α,5α-Dihydroxy-2β[(3R,S)-3,7-dihydroxy-7-methyl-trans-1-octenyl]-1α-cyclopentaneacetic Acid γ-Lactone, 3,3'-bis(Tetrahydropyran-2-yl Ether) (Formula 200)

The Formula-199 7-oxo lactone (0.500 g.) in 33 ml. of diethyl ether is treated at −78° C. with 2 equivalents of methylmagnesium bromide (0.766 ml. of 2.9 M) added dropwise over one min. The mixture is stirred at −78° for 30 min. more, then treated with an additional 2 equivalents of methylmagnesium bromide at −78° for 2 hr. The mixture is added to 40 ml. of saturated aqueous ammonium chloride and extracted with ether. The organic phase is washed with brine, dried, and concentrated. The concentrate is chromatographed on a HPLC column, eluting with acetone-methylene chloride (1:5) to yield the title compound, 0.391 g., having R$_f$ 0.39 (TLC on silica gel in acetone-methylene chloride (1:3)), NMR peaks at 5.66-5.33, 5.184.81, 4.81-4.47, 4.29-3.16, 2.97-1.29, and 1.16 δ, infrared absorption at 3550, 3000, 1770, 1460, 1440, 1430, 1350, 910, 865, 840, 810, 765, and 735 cm$^{-1}$, and mass spectral lines at 523.3118, 439, 437, 436, 421, 395, 131, and 85.

c. 3α,5α-Dihydroxy-2β-[(3R,S)-3,7-dihydroxy-7-methyl-trans-1-octenyl]-1α-cyclopentaneacetaldehyde γ-Lactol, 3,3'-bis(Tetrahydropyran-2-yl Ether) (Formula 201).

The formula-200 7-hydroxy-7-methyl lactone (6.98 g.) in 100 ml. of toluene is reduced at −78° C. with diisobutylaluminum hydride (DIBAL) (25 ml. of 1.5 M in toluene) added dropwise over 13 min. The mixture is stirred at −78° for one hr., treated with additional DIBAL (5 ml.), stirred for 2.25 hr. and again treated with DIBAL (5 ml.). After 0.75 hr. more stirring, the mixture is warmed to −40° over 30 min., then cooled to −78° and carefully quenched with saturated aqueous sodium sulfate. The mixture is diluted with 850 ml. of diethyl ether, stirred with powdered sodium sulfate (20 g.) until the aluminum salts coagulate, then filtered. The filtrate is concentrated and then chromatographed on silica gel eluting with acetone-methylene chloride (1:2 to 1:1) to yield the title lactol compound, 4.89 g. The product has R$_f$ 0.24 (TLC on silica gel in acetone-methylene chloride (1:2)), NMR peaks at 5.77-5.0, 4.86-4.33, 4.33-3.18, 3.11-1.27, and 1.15 δ, infrared absorption at 3500, 3000, 1750, 1730, 1470, 1450, 1440, 1370, 1340, 1200, 1120, 910, 865, and 810 cm$^{-1}$, and mass spectral lines at 527.3201, 426, 336, 247, 246, 131, and 85.

d. 19-Hydroxy-19-methyl-PGF$_{2\alpha}$, Methyl Ester, 11,15-bis(Tetrahydropyran-2-yl Ether), Mixed C-15 Epimers (Formula 202).

The Wittig reagent is first prepared from 4-carboxybutyl triphenylphosphonium bromide (16.19 g.) added to the reaction product of sodium hydride (3.51 g.) and 85 ml. of dimethylsulfoxide previously warmed to 70°-75° C. for 1.5 hr. and then cooled to about 25° C. The mixture is stirred at about 25° C. for 25 min., then treated with the formula-201 lactol (4.89 g.) in 35 ml. of dimethylsulfoxide added dropwise over 15 min. and stirred additional 30 min. The mixture is added to one liter of ice-water containing 250 ml. of 2 N potassium hydrogen sulfate and then extracted with ether. The organic phase is washed with brine, dried, and concentrated. The product, in 100 ml. of ether and 5 ml. of methanol, is esterified with diazomethane. The solution is concentrated and then chromatographed on a HPLC column eluting with ethyl acetate-Skellysolve B (1:1) to yield the title compounds, 4.08 g. having $R_f$ 0.20 (TLC on silica gel in ethyl acetate-Skellysolve B (2:1)) and 0.60 (TLC on silica gel in acetone-methylene chloride (1:2)), NMR peaks at 5.77–5.29, 4.89–4.60, 4.34–3.16, 3.67, 2.82–1.33, and 1.20δ, and infrared absorption at 3550, 3000, 1740, 1430, 1350, 1200, 1130, 1070, 1020, 970, 900, 865, and 810 cm$^{-1}$.

e. 19-Hydroxy-19-methyl-PGF$_{2\alpha}$, Methyl Ester and its (15R) Epimer (Formula 203).

The mixed formula-202 bis(THP ether) compounds (0.590 g.) are hydrolyzed in 33 ml. of acetic acid-water-tetrahydrofuran (20:10:3) at about 25° C. overnight. The mixture is concentrated from toluene and then ethyl acetate. The residue is chromatographed on a HPLC column eluting with acetone-methylene chloride (3:2) to obtain, first, the (15R) title compound, 0.129 g. The (15R) compound has $R_f$ 0.38 and the (15S) compound has $R_f$ 0.27 (TLC on silica gel in acetonemethylene chloride (3:1)). The 15S compound has NMR peaks at 5.75–5.04, 4.23–3.03, 3.65, 2.66–1.31, and 1.17δ, infrared absorption at 3450, 3000, 1740, 1430, 1360, 1200, 1150, 965, 920, and 900 cm$^{-1}$, and mass spectral lines at 671.4000, 686, 596, 581, 513, 506, 491, 423, 397, 333, 307, 243, and 217. The (15R) compound has very nearly the same spectral properties.

f. 19-Hydroxy-19-methyl-PGE$_2$, Methyl Ester, and its (15R) Epimer (Formula 205)

The mixed formula-202 bis(THP ether) PGF$_{2\alpha}$ compounds (0.602 g.) are oxidized with Jones reagent and then are hydrolyzed to replace THP blocking groups. The mixed C-15 epimers are separated by chromatography on a HPLC column, eluting with acetone-methylene chloride (1:1) to obtain, first, the 15R title compound, 0.119 g. and then the 15S title compound, 0.138 g. The 15R compound has $R_f$ 0.48 and the 15S compound has $R_f$ 0.36 (TLC on silica gel in acetone-methylene chloride (3:1)). The 15S compound has NMR peaks at 5.83–5.02, 4.56–3.33, 3.66, 3.04–1.34, and 1.20 δ, infrared absorption at 3450, 3000, 1740, 1430, 1360, 1300, 1230, 1150, 1070, 1000, 965, 900, and 760 cm$^{-1}$, and mass spectral lines at 597.3441, 581, 522, 507, 439, 349, 295, and 131. The 15R compound has very nearly the same spectral properties.

Preparation 10

9-(Dimethyl-t-butylsilyl)-19-keto-PGF$_{2\alpha}$, bis(Tetrahydropyranyl Ether) (Formula 207 of Chart 42) and 19-Keto-PGF$_{2\alpha}$, Methyl Ester (Formula 208)

a. Refer to Chart 42. The formula-206 compound (0.500 g.) in 8 ml. of methylene chloride is added to Collins reagent (prepared from chromic anhydride (0.526 g.) in pyridine (0.831 g.)) and methylene chloride at 0° C. The mixture is stirred at about 25° C. for 1.2 hr., then diluted with 200 ml. of ether, filtered, and concentrated. The residue (0.502 g.) consists of the formula-207 9-silyl-11,15-bis(THP ether)-19-keto compound.

b. The product of "a" is hydrolyzed in tetrahydrofuran-acetic acid-water (3:20:10) at 47°–50° C. for 4 hr. The mixture is concentrated and then chromatographed eluting with acetone-methylene chloride (1:1). There is obtained the title compound, 0.126 g., having $R_f$ 0.33 (TLC on silica gel in acetone-methylene chloride (1:1)). NMR peaks at 5.87–5.06, 4.60–3.12, 3.65, 2.69–0.84, and 2.13 δ; infrared absorption at 3350, 2900, 1730, 1430, 1350, 1220, 1160, and 965 cm$^{-1}$, and mass spectral lines at 598.3545, 583, 513, 508, 493, 423, 418, 217, and 187.

c. (15R)-19-Keto-PGF$_{2\alpha}$ (Formula 208) Replacing the (3S) lactone isomer with the corresponding (3R) isomer, there is obtained the title compound, having $R_f$ 0.27 (TLC on silica gel in methylene chloride-acetone (1:1)), NMR peaks at 5.70–5.15, 4.10, 3.67, 3.20, 2.17, and 2.70–1.20 δ; infrared absorption at 3300, 2990, 1710, 1420, 1350, and 965 cm$^{-1}$; and high resolution mass spectral line at 598.3516.

d. 19-Keto-13,14-dihydro-PGF$_{1\alpha}$, Methyl Ester

I. The formula-206 product, i.e. 9-dimethyl-t-butylsilyl-(19R,S)-19-hydroxy-PGF$_{2\alpha}$, 11,15-bis(tetrahydropyran-2-yl ether), methyl ester (2.0 g.) is reduced at C$_5$–C$_6$ and C$_{13}$–C$_{14}$ by catalytic hydrogenation in 75 ml. of ethyl acetate using 200 mg. of 5% palladium-on-carbon catalyst to a mixture of the corresponding PGF$_{1\alpha}$ and 13,14-dihydro-PGF$_{1\alpha}$ products which is further hydrogenated to the 13,14-dihydro compound.

II. Applying known oxidation procedures, the corresponding 9-silyl-11-15-bis(THP ether)-13,14-dihydro-19-keto-PGF$_{1\alpha}$, methyl ester is obtained.

Thereafter, by hydrolysis in tetrahydrofuran-acetic acid-water, the title compound is obtained. The TLC and NMR data show the presence of a less polar acetal form as well as the 19-keto form. $R_f$ 0.26, 0.54, and 0.67 (TLC on silica gel in A-IX solvent); NMR peaks at 4.52–3.30, 3.62, 3.38, 3.00–0.87, 2.08, and 1.18 δ; and mass spectral lines at 512.3336, 528, 517, 497, 427, 422, 412, 369, and 217.

Preparation 11

19-Hydroxy-19-methyl-PGF$_{2\alpha}$, Methyl Ester (Formula 215 of Chart 43)

Refer to Chart 43. The formula-212 9-silyl-11,15-bis(THP ether)-19-keto compound (0.500 g.) in 50 ml. of benzene is treated at about 25° C. with 2.3 equivalents of trimethylaluminum added dropwise over one min. The mixture is stirred for 30 min. and then added to 50 ml. of saturated aqueous ammonium chloride and extracted with ethyl acetate. The organic phase is washed with brine, dried, and concentrated. The residue is chromatographed to yield the corresponding 19-hydroxy-19- methyl compound which is then deblocked in tetrahydrofuran-acetic acid-water (3:20:10) to yield the title compound.

Preparation 11A 15,19-Dimethyl-19-hydroxy-PGF$_{2\alpha}$, Methyl Ester and its (15R) Epimer (Formula 215 of Chart 43)

As starting material there is used (15R,S)-15-methyl-19,20-didehydro-PGF$_{2\alpha}$, 11-tetrahydropyranyl ether, methyl ester. After saponification and recovery as the free acid, the compound is treated first with the silylating agent, and then with dihydropyran in the presence of pyridine hydrochloride, Thereafter the 15-methyl 19-keto compound of formula 212 is prepared using procedures described herein, thence the title compound.

Preparation 12

(2E)-$\Delta^2$-19-Hydroxy-19-methyl-PGF$_{2\alpha}$, Methyl Ester (Formula 223 of Chart 44)

a. Refer to Chart 44. The formula-221 2-phenyl selenidyl compound is first prepared. The starting material is the methyl ester of formula-220 as the bis(tetrahydropyran-2-yl ether) (0.4 g.). A solution of that bis(THP) methyl ester in 5 ml. of tetrahydrofuran is added dropwise to the amide formed from N-isopropylcyclohexylamine (0.3 g.) and n-butyllithium (equivalent 1.6 M hexane solution) in tetrahydrofuran (7 ml.) cooled to $-78°$ C. The mixture is stirred at $-78°$ C. for 45 min. and then phenylselenenyl chloride is added in tetrahydrofuran solution over a 7 minute period. The mixture is stirred at $-78°$ C. for an additional hour, then poured into 30 ml. of saturated ammonium chloride-ice-water mixture and extracted with diethyl ether. The organic phase is dried and concentrated. The residue is chromatographed on silica gel, eluting with ethyl acetate-toluene (1:8) to give the formula-221 compound.

b. The formula-222 $\Delta^2$ compound is formed by oxidative elimination. The product of "a", in methylene chloride, is treated with 10% hydrogen peroxide at about 25° C., stirring vigorously for one hr. The organic phase is washed with 5% sodium bicarbonate, saturated sodium bicarbonate, and brine, dried, and concentrated to yield the formula-222 compound.

c. The title compound is obtained on deblocking the product of "b" using acetic acid-water-tetrahydrofuran (20:10:3) at 40° C.

Preparation 13

(4Z)-$\Delta^4$-19$\xi$-Hydroxy-PGF$_{1\alpha}$ (Formula 227 of Chart 45)

Refer to Chart 45. There is first prepared the formula-226 6-membered lactol.

In step "a" the formula-225 enol-ether is prepared as follows. A suspension of methoxymethyltriphenylphosphonium chloride (Levine, J. Am. Chem. Soc. 80, 6150 (1958) 32.4 g.) in 150 ml. of tetrahydrofuran (THF) is cooled to $-15°$ C. and to it is added 69.4 ml. of butyllithium (1.6 M in hexane) in 45 ml. of THF. After 30 min. there is added a solution of the formula-224 3$\alpha$,5$\alpha$-dihydroxy-2$\beta$-(3$\alpha$,7$\xi$-dihydroxy-trans-1-octenyl)-1$\alpha$-cyclopentaneacetaldehyde-$\gamma$-lactol tris(tetrahydropyranyl ether) (J. C. Sih, Prostaglandins 13, 831-5 (1977) 10.4 g.) in 90 ml. of THF. The mixture is stirred for 1.5 hr., meanwhile warming to about 25° C., and is then concentrated under reduced pressure. The residue is partitioned between dichloromethane and water, and the organic phase is dried and concentrated. This residue is then subjected to chromatography over silica gel, eluting with cyclohexane-ethyl acetate (2:1). Those fractions shown by thin-layer chromatography (TLC) to contain the formula-225 intermediate are combined and concentrated to yield that enol-ether.

In step "b", the above enol-ether, in 20 ml. of THF, is hydrolyzed with 50 ml. of 66% acetic acid at about 57° C. for 2.5 hr. The mixture is concentrated under reduced pressure. Toluene is added to the residue and the solution is again concentrated. Finally the residue is subjected to chromatography on silica gel, eluting with chloroform-methanol (6:1). The formula-226 lactol is obtained by combining and concentrating suitable fractions.

In step "c" the title compound is obtained as follows. 3-Carboxypropyltriphenylphosphonium bromide is prepared by heating triphenylphosphine (156.8 g.) and 4-bromobutyric acid (100 g.) in 125 ml. of benzene at reflux for 18 hr. The crystalline product is filtered off, washed with benzene, and recrystallized from ethanol-acetonitrile-ether, 150 g., m.p. 247°-249° C.

This phosphonium bromide (10.6 g.) is then added to sodio methylsulfinylcarbanide prepared from sodium hydride (2.08 g. 57%) and 30 ml. of dimethyl sulfoxide, and the resulting Wittig reagent is combined with the formula-226 lactol of step "b", in 20 ml. of dimethyl sulfoxide. The mixture is stirred overnight, diluted with about 200 ml. of benzene, and washed with potassium hydrogen sulfate solution. The two lower layers are washed with dichloromethane, and the organic phases are combined, washed with brine, dried, and concentrated under reduced pressure. The residue is subjected to chromatography over acid-washed silica gel eluting with ethyl acetate-isomeric hexanes (3:1). Those fractions shown to contain the desired compound by TLC are combined and concentrated to yield the title compound.

EXAMPLE 1

(5Z)-9-Deoxy-6,9$\alpha$-epoxy-$\Delta^5$-(19R,S)-19-hydroxy-PGF$_1$, Methyl Ester (Formula 228)

I. Refer to Chart 1. There are first prepared the isomeric 5-iodo compounds of formula 17. A solution of the formula-16 (19R,S)-19-hydroxy-PGF$_{2\alpha}$, methyl ester (Preparation 3, 0.655 g.) in 14 ml. of methylene chloride is treated with 14 ml. of a saturated aqueous solution of sodium bicarbonate and cooled to 0°–5° C. There is then added, with vigorous stirring, a solution of iodine (0.474 g.) in 35 ml. of methylene chloride. The mixture is stirred for a total of one hr., with a final temperature of 10° C. The organic phase is separated, washed with aqueous sodium sulfite (10%), dried, and concentrated to an oil, 0.803 g., mainly the 6R,5R isomer.

II. The above iodo compounds, in 32 ml. of benzene, are treated with 1.70 ml. of DBN (1,5-diazabicyclo[4.30]-nonene-5) at about 45° C. for 25 hr. The mixture is diluted with 125 ml. of benzene containing 1% triethylamine and washed with ice-water and brine, dried, and concentrated. Traces of DBN are removed by taking up in 150 ml. of benzene and washing with ice-water. The organic phase is dried and concentrated to yield the formula-228 title compound, 0.300 g., having R$_f$ 0.34 (in acetone-hexane (3:1)), NMR peaks at 5.52, 4.55, 4.30–3.60, 3.66, 2.90–1.30, and 1.13$\delta$, infrared absorption at 3400, 2995, 1735, 1695, 1430, and 970 cm$^{-1}$, and a high resolution mass spectral line at 598.3563.

EXAMPLE 2

(6R)-9-Deoxy-6,9$\alpha$-epoxy-(19R,S)-19-hydroxy-PGF$_1$, Methyl Ester (Formula 20) and (6S) Isomer I. A solution of $\Delta^{19}$-PGF$_{2\alpha}$, bis(tetrahydropyranyl ether), methyl ester (Preparation 2, 1.00 g.) in 23 ml. of tetrahydrofuran is added dropwise to a suspension of mercuric acetate (1.545 g.) in 23 ml. of water and 23 ml. of tetrahydrofuran. Stirring is continued for 2.5 hr. at about 25° C. The mixture is cooled to 0°–5° C. and treated with solid sodium borohydride (0.388 g.) added in portions over 2.5 min. Thereafter the mixture is stirred at about 25° C. for 3.5 min. and diluted with 100 ml. of ether. The solution is decanted from the mercury and separated. The aqueous phase is further extracted with ether and the combined organic phases are concentrated. The residue is taken up in 300 ml. of ether, washed with brine, dried, and concentrated to an oil, 1.230 g., containing the bis(THP ethers) of the title compounds.

II. The above product is deblocked in acetic acid-water-tetrahydrofuran (20:10:3) at about 45° C. for 2.5 hr. The mixture is concentrated, finally azeotroped with benzene to yield the mixed C-6 epimers of formula 20.

III. The above product is chromatographed by HPLC on a Merck "B" column, eluting with acetone-hexane (2:1), to yield a less polar fraction, 0.086 g., (6R)-9-deoxy-6,9α-epoxy-(19R,S)-19-hydroxy-PGF$_1$, methyl ester, having R$_f$ 0.28 (in acetone-hexane (3:1)), NMR spectral lines at 5.50, 4.35–3.10, 3.67, 2.60–1.30, and 1.13 δ, and high resolution mass spectral line at 600.3681. There is also obtained the more polar fraction, 0.150 g., (6S)-9-deoxy-6,9α-epoxy-(19R,S)-19-hydroxy-PGF$_1$, methyl ester, having R$_f$ 0.25 (in acetone-hexane (3:1)), NMR spectral lines at 5.50, 4.40, 4.25–3.30, 3.67, 2.65–1.30, and 1.13 δ, and high resolution mass spectral line at 600.3705.

EXAMPLE 3

(5Z)-9-Deoxy-6,9α-epoxy-Δ$^5$-(19R,S)-19-hydroxy-PGF$_1$, Sodium Salt (Formula 240)

A solution of the methyl ester of (5Z)-9-deoxy-6,9α-epoxy-Δ$^5$-(19R,S)-19-hydroxy-PGF$_1$ (Example 1, 0.140 g., in 6 ml. methanol and 4 ml. of water is treated with 4.10 ml. of 0.1 N aqueous sodium hydroxide at about 25° C. for 25 hr. The mixture is concentrated and finally freeze-dried to yield the title compound as a white free-flowing solid, 0.130 g., having m.p. 152°–158° C., and a high resolution mass spectral line at 656.3761.

EXAMPLE 4

(5Z)-9-Deoxy-6,9α-epoxy-Δ$^5$-(19R,S)-19-hydroxy-PGF$_1$, 4-Acetylphenyl Ester.

Two methods are described.

I. Mixed anhydride method. A stirred suspension of 19-hydroxy-PGI$_2$ sodium salt (Example 3, 0.195 g.) in 15 ml. of methylene chloride and 0.120 g. of triethylamine is treated at about 0° C. with isobutylchloroformate (0.0656 g.) in 1 ml. of methylene chloride. The mixture is stirred at about 25° C. for 2 hr., then cooled again to about 0° C. and treated with 4-hydroxyacetophenone (0.0653 g.) in 1 ml. of methylene chloride containing about 0.25 ml. of triethylamine. The mixture is stirred at about 25° C. for one hr., cooled to 0° C., diluted with 25 ml. of a mixture of methylene chloride-triethylamine (95:5), washed with 5% aqueous sodium bicarbonate and cold 0.1 N. potassium hydroxide. The organic phase is dried and concentrated to the title compound.

II. 2-Halo-pyridinium salt method. A solution of 19-hydroxy-PGI$_2$ sodium salt (Example 3, 1.04 g.) in 35 ml. of dimethylformamide and 0.352 g. of triethylamine is treated with 2-bromo-1-methylpyridinium iodide (J. Chem. Soc., Perkins Trans., 2 (1974) 790) (0.81 g.) at about 25° C. for one hr. The mixture is then treated with 4-hydroxyacetophenone (0.364 g.) in 2 ml. of dimethylformamide and 0.4 g. of triethylamine at about 25° C. The mixture is stirred about 16 hr., then poured into ice-water containing 4 ml. of 1 N potassium hydroxide and extracted with diethyl ether. The organic phase is washed with cold 0.02 N potassium hydroxide, dried, and concentrated to the title compound.

Following the procedures of the Preparations and Examples herein and applying the process steps shown in the Charts as described herein or known to those skilled in the art, the following compounds are prepared wherein R$_{13}$ is hydrogen as represented by formula 4

A. wherein R$_1$ is —COOR$_3$ (5Z)-9-deoxy-6,9α-epoxy-Δ$^5$-19ξ-hydroxy-PGF$_1$, methyl ester (5Z)-9-deoxy-6,9α-epoxy-Δ$^5$-16,16-dimethyl-19ξ-hydroxy-PGF$_1$, methyl ester (5Z)-9-deoxy-6,9α-epoxy-Δ$^5$-16,16-difluoro-19ξ-hydroxy-PGF$_1$, methyl ester (5Z)-9-deoxy-6,9α-epoxy-Δ$^5$-15-methyl-19ξ-hydroxy-PGF$_1$, methyl ester (5Z)-9-deoxy-6,9α-epoxy-Δ$^5$-13,14-cis-19ξ-hydroxy-PGF$_1$, methyl ester (5Z)-9-deoxy-6,9α-epoxy-Δ$^5$-13,14-didehydro-19ξ-hydroxy-PGF$_1$, methyl ester (5Z)-9-deoxy-6,9α-epoxy-Δ$^5$-13,14-didehydro-16,16-difluoro-19ξ-hydroxy-PGF$_1$, methyl ester (5Z)-9-deoxy-6,9α-epoxy-Δ$^5$-13,14-dihydro-19ξ-hydroxy-PGF$_1$, methyl ester (5Z)-9-deoxy-6,9α-epoxy-Δ$^5$-13,14-dihydro-16,16-difluoro-19ξ-hydroxy-PGF$_1$, methyl ester (5Z)-9-deoxy-6,9α-epoxy-Δ$^5$-11-deoxy-19ξ-hydroxy-PGF$_1$, methyl ester (5Z)-9-deoxy-6,9α-epoxy-Δ$^5$-11-deoxy-16,16-difluoro-19ξ-hydroxy-PGF$_1$, methyl ester (5Z)-9-deoxy-6,9α-epoxy-Δ$^5$-11-deoxy-11α-hydroxymethyl-19ξ-hydroxy-PGF$_1$, methyl ester (5Z)-9-deoxy-6,9α-epoxy-2,2-difluoro-Δ$^5$-19ξ-hydroxy-PGF$_1$, methyl ester (5Z)-9-deoxy-6,9α-epoxy-2,2,16,16-tetrafluoro-Δ$^5$-19ξ-hydroxy-PGF$_1$, methyl ester 9-deoxy-6ξ,9α-epoxy-19ξ-hydroxy-PGF$_1$, methyl ester 9-deoxy-6ξ,9α-epoxy-16,16-dimethyl-19ξ-hydroxy-PGF$_1$, methyl ester 9-deoxy-6ξ,9α-epoxy-16,16-difluoro-19ξ-hydroxy-PGF$_1$, methyl ester 9-deoxy-6ξ,9α-epoxy-15-methyl-19ξ-hydroxy-PGF$_1$, methyl ester 9-deoxy-6ξ,9α-epoxy-13,14-cis-19ξ-hydroxy-PGF$_1$, methyl ester 9-deoxy-6ξ,9α-epoxy-13,14-didehydro-19ξ-hydroxy-PGF$_1$, methyl ester 9-deoxy-6ξ,9α-epoxy-13,14-dihydro-19ξ-hydroxy-PGF$_1$, methyl ester 9-deoxy-6ξ,9α-epoxy-13,14-dihydro-16,16-difluoro-19ξ-hydroxy-PGF$_1$, methyl ester 9-deoxy-6ξ,9α-epoxy-2,2-difluoro-19ξ-hydroxy-PGF$_1$, methyl ester (2E)-9-deoxy-6ξ,9α-epoxy-Δ$^2$-19ξ-hydroxy-PGF$_1$, methyl ester (2E)-9-deoxy-6ξ,9α-epoxy-Δ$^2$-16,16-difluoro-19ξ-hydroxy-PGF$_1$, methyl ester (2E)-9-deoxy-6ξ,9α-epoxy-Δ²-13,14-dihydro-19ξ-hydroxy-PGF₁, methyl ester
9-deoxy-6ξ,9α-epoxy-6ξ,19ξ-dihydroxy-PGF₁, methyl ester
9-deoxy-6ξ,9α-epoxy-6ξ,19ξ-dihydroxy-16,16-dimethyl-PGF₁, methyl ester
9-deoxy-6ξ,9α-epoxy-6ξ,19ξ-dihydroxy-16,16-difluoro-PGF₁, methyl ester
9-deoxy-6ξ,9α-epoxy-6ξ,19ξ-dihydroxy-15-methyl-PGF₁, methyl ester
9-deoxy-6ξ,9α-epoxy-6ξ,19ξ-dihydroxy-13,14-cis-PGF₁, methyl ester
9-deoxy-6ξ,9α-epoxy-6ξ,19ξ-dihydroxy-13,14-didehydro-PGF₁, methyl ester
9-deoxy-6ξ,9α-epoxy-6ξ,19ξ-dihydroxy-13,14-didehydro-16,16-difluoro-PGF₁, methyl ester
9-deoxy-6ξ,9α-epoxy-6ξ,19ξ-dihydroxy-13,14-dihydro-PGF₁, methyl ester
9-deoxy-6ξ,9α-epoxy-6ξ,19ξ-dihydroxy-13,14-dihydro-16,16-difluoro-PGF₁, methyl ester
9-deoxy-6ξ,9α-epoxy-6ξ,19ξ-dihydroxy-11-deoxy-PGF₁, methyl ester
9-deoxy-6ξ,9α-epoxy-6ξ,19ξ-dihydroxy-11-deoxy-16,16-difluoro-PGF₁, methyl ester
9-deoxy-6ξ,9α-epoxy-6ξ,19ξ-dihydroxy-11-deoxy-11α-hydroxymethyl-PGF₁, methyl ester
9-deoxy-6ξ,9α-epoxy-6ξ,19ξ-dihydroxy-2,2-difluoro-PGF₁, methyl ester
9-deoxy-6ξ,9α-epoxy-6ξ,19ξ-dihydroxy-2,2,16,16-tetrafluoro-PGF₁, methyl ester
(2E)-9-deoxy-6ξ,9α-epoxy-6ξ,19ξ-dihydroxy-Δ²-PGF₁, methyl ester
(2E)-9-deoxy-6ξ,9α-epoxy-6ξ,19ξ-dihydroxy-Δ²-16,16-difluoro-PGF₁, methyl ester
(4Z)-9-deoxy-5,9α-epoxy-Δ⁴-19ξ-hydroxy-PGF₁, methyl ester
(4Z)-9-deoxy-5,9α-epoxy-Δ⁴-16,16-dimethyl-19ξ-hydroxy-PGF₁, methyl ester
(4Z)-9-deoxy-5,9α-epoxy-Δ⁴-16,16-difluoro-19ξ-hydroxy-PGF₁, methyl ester
(4Z)-9-deoxy-5,9α-epoxy-Δ⁴-15-methyl-19ξ-hydroxy-PGF₁, methyl ester
(4Z)-9-deoxy-5,9α-epoxy-Δ⁴-13,14-cis-19ξ-hydroxy-PGF₁, methyl ester
(4Z)-9-deoxy-5,9α-epoxy-Δ⁴-13,14-didehydro-19ξ-hydroxy-PGF₁, methyl ester
(4Z)-9-deoxy-5,9α-epoxy-Δ⁴-13,14-didehydro-16,16-difluoro-19ξ-hydroxy-PGF₁, methyl ester
(4Z)-9-deoxy-5,9α-epoxy-Δ⁴-13,14-dihydro-19ξ-hydroxy-PGF₁, methyl ester
(4Z)-9-deoxy-5,9α-epoxy-Δ⁴-13,14-dihydro-16,16-difluoro-19ξ-hydroxy-PGF₁, methyl ester
(4Z9-9-deoxy-5,9α-epoxy-Δ⁴-11-deoxy-19ξ-hydroxy-PGF₁, methyl ester
(4Z)-9-deoxy-5,9α-epoxy-Δ⁴-11-deoxy-16,16-difluoro-19ξ-hydroxy-PGF₁, methyl ester
(4Z)-9-deoxy-5,9α-epoxy-Δ⁴-11-deoxy-11α-hydroxymethyl-19ξ-hydroxy-PGF₁, methyl ester
(4Z)-9-deoxy-5,9α-epoxy-2,2-difluoro-Δ⁴-19ξ-hydroxy-PGF₁, methyl ester
(4Z)-9-deoxy-5,9α-epoxy-2,2-difluoro-Δ⁴-16,16-difluoro-19ξ-hydroxy-PGF₁, methyl ester
(2E,4Z)-9-deoxy-5,9α-epoxy-Δ²,Δ⁴-19ξ-hydroxy-PGF₁, methyl ester
(2E,4Z)-9-deoxy-5,9α-epoxy-Δ²,Δ⁴-16,16-difluoro-19ξ-hydroxy-PGF₁, methyl ester
9-deoxy-5ξ,9α-epoxy-19-hydroxy-PGF₁, methyl ester
9-deoxy-5ξ,9α-epoxy-16,16-dimethyl-19-hydroxy-PGF₁, methyl ester
9-deoxy-5ξ,0α-epoxy-16,16-difluoro-19-hydroxy-PGF₁, methyl ester
9-deoxy-5ξ,9α-epoxy-15-methyl-19-hydroxy-PGF₁, methyl ester
9-deoxy-5ξ,9α-epoxy-13,14-cis-19-hydroxy-PGF₁, methyl ester
9-deoxy-5ξ,9α-epoxy-13,14-didehydro-19-hydroxy-PGF₁, methyl ester
9-deoxy-5ξ,9α-epoxy-13,14-dihydro-19-hydroxy-PGF₁, methyl ester
9-deoxy-5ξ,9α-epoxy-13,14-dihydro-16,16-difluoro-19ξ-hydroxy-PGF₁, methyl ester
9-deoxy-5ξ,9α-epoxy-2,2-difluoro-19ξ-hydroxy-PGF₁, methyl ester
(2E)-9-deoxy-5ξ,9α-epoxy-Δ²-19ξ-hydroxy-PGF₁, methyl ester
(2E)-9-deoxy-5ξ,9α-epoxy-Δ²-16,16-difluoro-19ξ-hydroxy-PGF₁, methyl ester
(2E)-9-deoxy-5ξ,9α-epoxy-Δ²-13,14-dihydro-9ξ-hydroxy-PGF₁, methyl ester
9-deoxy-5ξ,9α-epoxy-5ξ,19ξ-dihydroxy-PGF₁, methyl ester
(2E)-9-deoxy-5ξ,9α-epoxy-5ξ,19ξ-dihydroxy-Δ²-PGF₁, methyl ester
(5Z)-9-deoxy-6,9α-epoxymethano-Δ⁵-19ξ-hydroxy-PGF₁, methyl ester
(5Z)-9-deoxy-6,9α-epoxymethano-Δ⁵-16,16-dimethyl-19ξ-hydroxy-PGF₁, methyl ester
(5Z)-9-deoxy-6,9α-epoxymethano-Δ⁵-16,16-difluoro-19ξ-hydroxy-PGF₁, methyl ester
(5Z)-9-deoxy-6,9α-epoxymethano-Δ⁵-15-methyl-19ξ-hydroxy-PGF₁, methyl ester
(5Z)-9-deoxy-6,9α-epoxymethano-Δ⁵-13,14-cis-19ξ-hydroxy-PGF₁, methyl ester
(5Z)-9-deoxy-6,9α-epoxymethano-Δ⁵-13,14-didehydro-19ξ-hydroxy-PGF₁, methyl ester
(5Z)-9-deoxy-6,9α-epoxymethano-Δ⁵-13,14-didehydro-16,16-difluoro-19ξ-hydroxy-PGF₁, methyl ester
(5Z)-9-deoxy-6,9α-epoxymethano-Δ⁵-13,14-dihydro-19ξ-hydroxy-PGF₁, methyl ester
(5Z)-9-deoxy-6,9α-epoxymethano-Δ⁵-13,14-dihydro-16,16-difluoro-19ξ-hydroxy-PGF₁, methyl ester
(5Z)-9-deoxy-6,9α-epoxymethano-Δ⁵-11-deoxy-19ξ-hydroxy-PGF₁, methyl ester
(5Z)-9-deoxy-6,9α-epoxymethano-Δ⁵-11-deoxy-16,16-difluoro-19ξ-hydroxy-PGF₁, methyl ester
(5Z)-9-deoxy-6,9α-epoxymethano-Δ⁵-11-deoxy-11α-hydroxymethyl-19ξ-hydroxy-PGF₁, methyl ester
(5Z)-9-deoxy-6,9α-epoxymethano-2,2-difluoro-Δ⁵-19ξ-hydroxy-PGF₁, methyl ester
(5Z)-9-deoxy-6,9α-epoxymethano-2,2,16,16-tetrafluoro-Δ⁵-19ξ-hydroxy-PGF₁, methyl ester
9-deoxy-6ξ,9α-epoxymethano-19ξ-hydroxy-PGF₁, methyl ester
9-deoxy-6ξ,9α-epoxymethano-16,16-dimethyl-19ξ-hydroxy-PGF₁, methyl ester
9-deoxy-6ξ,9α-epoxymethano-16,16-difluoro-19ξ-hydroxy-PGF₁, methyl ester
9-deoxy-6ξ,9α-epoxymethano-15-methyl-19ξ-hydroxy-PGF₁, methyl ester
9-deoxy-6ξ,9α-epoxymethano-13,14-cis-19ξ-hydroxy-PGF₁, methyl ester
9-deoxy-6ξ,9α-epoxymethano-13,14-didehydro-19ξ-hydroxy-PGF₁, methyl ester
9-deoxy-6ξ,9α-epoxymethano-13,14-dihydro-19ξ-hydroxy-PGF₁, methyl ester 9-deoxy-6ξ,9α-epoxymethano-13,14-dihydro-16,16-difluoro-19ξ-hydroxy-PGF$_1$, methyl ester
(2E)-9-deoxy-6ξ,9α-epoxymethano-Δ$^2$-19ξ-hydroxy-PGF$_1$, methyl ester
(2E)-9-deoxy-6ξ,9α-epoxymethano-Δ$^2$-16,16-difluoro-19ξ-hydroxy-PGF$_1$, methyl ester
(2E)-9-deoxy-6ξ,9α-epoxymethano-Δ$^2$-13,14-dihydro-19ξ-hydroxy-PGF$_1$, methyl ester
9-deoxy-6ξ,9α-epoxy-5ξ,19ξ-dihydroxy-PGF$_1$, methyl ester
9-deoxy-6ξ,9α-epoxy-5ξ,9ξ-dihydroxy-16,16-dimethyl-PGF$_1$, methyl ester
9-deoxy-6ξ,9α-epoxy-5ξ,19ξ-dihydroxy-16,16-difluoro-PGF$_1$, methyl ester
9-deoxy-6ξ,9α-epoxy-5ξ,19ξ-dihydroxy-15-methyl-PGF$_1$, methyl ester
9-deoxy-6ξ,9α-epoxy-5ξ,9ξ-dihydroxy-13,14-cis-PGF$_1$, methyl ester
9-deoxy-6ξ,9α-epoxy-5ξ,19ξ-dihydroxy-13,14-didehydro-PGF$_1$, methyl ester
9-deoxy-6ξ,9α-epoxy-5ξ,19ξ-dihydroxy-13,14-dihydro-PGF$_1$, methyl ester
9-deoxy-6ξ,9α-epoxy-5ξ,19ξ-dihydroxy-13,14-dihydro-16,16-difluoro-PGF$_1$, methyl ester
9-deoxy-6ξ,9α-epoxy-2,2-difluoro-5ξ,9ξ-dihydroxy-PGF$_1$, methyl ester
(2E)-9-deoxy-6ξ,9α-epoxy-Δ$^2$-5ξ,19ξ-dihydroxy-PGF$_1$, methyl ester
(2E)-9-deoxy-6ξ,9α-epoxy-Δ$^2$-5ξ,19ξ-dihydroxy-16,16-difluoro-PGF$_1$, methyl ester
(2E)-9-deoxy-6ξ,9α-epoxy-Δ$^2$-5ξ,19ξ-dihydroxy-13,14-dihydro-PGF$_1$, methyl ester
(4E)-9-deoxy-6ξ,9α-epoxy-Δ$^4$-19ξ-hydroxy-PGF$_1$, methyl ester
(4E)-9-deoxy-6ξ,9α-epoxy-Δ$^4$-16,16-dimethyl-19ξ-hydroxy-PGF$_1$, methyl ester
(4E)-9-deoxy-6ξ,9α-epoxy-Δ$^4$-16,16-difluoro-19ξ-hydroxy-PGF$_1$, methyl ester
(4E)-9-deoxy-6ξ,9α-epoxy-Δ$^4$-15-methyl-19ξ-hydroxy-PGF$_1$, methyl ester
(4E)-9-deoxy-6ξ,9α-epoxy-Δ$^4$-13,14-cis-19ξ-hydroxy-PGF$_1$, methyl ester
(4E)-9-deoxy-6ξ,9α-epoxy-Δ$^4$-13,14-didehydro-19ξ-hydroxy-PGF$_1$, methyl ester
(4E)-9-deoxy-6ξ,9α-epoxy-Δ$^4$-13,14-dihydro-19ξ-hydroxy-PGF$_1$, methyl ester
(4E)-9-deoxy-6ξ,9α-epoxy-Δ$^4$-13,14-dihydro-16,16-difluoro-19ξ-hydroxy-PGF$_1$, methyl ester
(4E)-9-deoxy-6ξ,9α-epoxy-2,2-difluoro-Δ$^4$-19ξ-hydroxy-PGF$_1$, methyl ester
(2E,4E)-9-deoxy-6ξ,9α-epoxy-Δ$^2$,Δ$^4$-19ξ-hydroxy-PGF$_1$, methyl ester
(2E,4E)-9-deoxy-6ν,9α-epoxy-Δ$^2$,Δ$^4$-16,16-difluoro-19ξ-hydroxy-PGF$_1$, methyl ester
(2E,4E)-9-deoxy-6ξ,9α-epoxy-Δ$^2$,Δ$^4$-13,14-dihydro-19ξ-hydroxy-PGF$_1$, methyl ester
9-deoxy-6ξ,9α-epoxy-6ξ-methoxy-19ξ-hydroxy-PGF$_1$, methyl ester
9-deoxy-6ξ,9α-epoxy-6ξ-methoxy-16,16-dimethyl-19ξ-hydroxy-PGF$_1$, methyl ester
9-deoxy-6ξ,9α-epoxy-6ξ-methoxy-16,16-difluoro-19ξ-hydroxy-PGF$_1$, methyl ester
9-deoxy-6ξ,9α-epoxy-6ξ-methoxy-15-methyl-19ξ-hydroxy-PGF$_1$, methyl ester
9-deoxy-6ξ,9α-epoxy-6ξ-methoxy-13,14-cis-19ξ-hydroxy-PGF$_1$, methyl ester
9-deoxy-6ξ,9α-epoxy-6ξ-methoxy-13,14-didehydro-19ξ-hydroxy-PGF$_1$, methyl ester
9-deoxy-6ξ,9α-epoxy-6ξ-methoxy-13,14-didehydro-16,16-difluoro-19ξ-hydroxy-PGF$_1$, methyl ester
9-deoxy-6ξ,9α-epoxy-6ξ-methoxy-13,14-dihydro-19ξ-hydroxy-PGF$_1$, methyl ester
9-deoxy-6ξ,9α-epoxy-6ξ-methoxy-13,14-dihydro-16,16-difluoro-19ξ-hydroxy-PGF$_1$, methyl ester
9-deoxy-6ξ,9α-epoxy-6ξ-methoxy-11-deoxy-19ξ-hydroxy-PGF$_1$, methyl ester
9-deoxy-6ξ,9α-epoxy-6ξ-methoxy-11-deoxy-16,16-difluoro-19ξ-hydroxy-PGF$_1$, methyl ester
9-deoxy-6ξ,9α-epoxy-6ξ-methoxy-11-deoxy-11α-hydroxymethyl-19ξ-hydroxy-PGF$_1$, methyl ester
9-deoxy-6ξ,9α-epoxy-2,2-difluoro-6ξ-methoxy-19ξ-hydroxy-PGF$_1$, methyl ester
9-deoxy-6ξ,9α-epoxy-2,2,16,16-tetrafluoro-6ξ-methoxy-19ξ-hydroxy-PGF$_1$, methyl ester
9-deoxy-6ξ,9α-epoxy-4-oxo-19ξ-hydroxy-PGF$_1$, methyl ester
9-deoxy-6ξ,9α-epoxy-4-oxo-16,16-dimethyl-19ξ-hydroxy-PGF$_1$, methyl ester
9-deoxy-6ξ,9α-epoxy-4-oxo-16,16-difluoro-19ξ-hydroxy-PGF$_1$, methyl ester
9-deoxy-6ξ,9α-epoxy-4-oxo-15-methyl-19ξ-hydroxy-PGF$_1$, methyl ester
9-deoxy-6ξ,9α-epoxy-4-oxo-13,14-cis-19ξ-hydroxy-PGF$_1$, methyl ester
9-deoxy-6ξ,9α-epoxy-4-oxo-13,14-didehydro-19ξ-hydroxy-PGF$_1$, methyl ester
9-deoxy-6ξ,9α-epoxy-4-oxo-13,14-didehydro-16,16-difluoro-19ξ-hydroxy-PGF$_1$, methyl ester
9-deoxy-6ξ,9α-epoxy-4-oxo-13,14-dihydro-19ξ-hydroxy-PGF$_1$, methyl ester
9-deoxy-6ξ,9α-epoxy-4-oxo-13,14-dihydro-16,16-difluoro-19ξ-hydroxy-PGF$_1$, methyl ester
9-deoxy-6ξ,9α-epoxy-4-oxo-11-deoxy-19ξ-hydroxy-PGF$_1$, methyl ester
9-deoxy-6ξ,9α-epoxy-4-oxo-11-deoxy-16,16-difluoro-19ξ-hydroxy-PGF$_1$, methyl ester
9-deoxy-6ξ,9α-epoxy-4-oxo-11-deoxy-11α-hydroxymethyl-19ξ-hydroxy-PGF$_1$, methyl ester
9-deoxy-6ξ,9α-epoxy-2,2-difluoro-4-oxo-19ξ-hydroxy-PGF$_1$, methyl ester
9-deoxy-6ξ,9α-epoxy-2,2,16,16-tetrafluoro-4-oxo-19ξ-hydroxy-PGF$_1$, methyl ester
9-deoxy-6ξ,9α-epoxy-Δ$^6$-19ξ-hydroxy-PGF$_1$, methyl ester
9-deoxy-6ξ,9α-epoxy-Δ$^6$-16,16-dimethyl-19ξ-hydroxy-PGF$_1$, methyl ester
9-deoxy-6ξ,9α-epoxy-Δ$^6$-16,16-difluoro-19ξ-hydroxy-PGF$_1$, methyl ester
9-deoxy-6ξ,9α-epoxy-Δ$^6$-15-methyl-19ξ-hydroxy-PGF$_1$, methyl ester
9-deoxy-6ξ,9α-epoxy-Δ$^6$-13,14-cis-19ξ-hydroxy-PGF$_1$, methyl ester
9-deoxy-6ξ,9α-epoxy-Δ$^6$-13,14-didehydro-19ξ-hydroxy-PGF$_1$, methyl ester
9-deoxy-6ξ,9α-epoxy-Δ$^6$-13,14-didehydro-16,16-difluoro-19ξ-hydroxy-PGF$_1$, methyl ester
9-deoxy-6ξ,9α-epoxy-Δ$^6$-13,14-dihydro-19ξ-hydroxy-PGF$_1$, methyl ester
9-deoxy-6ξ,9α-epoxy-Δ$^6$-13,14-dihydro-16,16-difluoro-19ξ-hydroxy-PGF$_1$, methyl ester
9-deoxy-6ξ,9α-epoxy-Δ$^6$-11-deoxy-19ξ-hydroxy-PGF$_1$, methyl ester
9-deoxy-6ξ,9α-epoxy-Δ$^6$-11-deoxy-16,16-difluoro-19ξ-hydroxy-PGF$_1$, methyl ester
9-deoxy-6ξ,9α-epoxy-66$^6$-11-deoxy-11α-hydroxymethyl-19ξ-hydroxy-PGF$_1$, methyl ester 9-deoxy-6ξ,9α-epoxy-2,2-difluoro-Δ⁶-19ξ-hydroxy-PGF₁, methyl ester
9-deoxy-6ξ,9α-epoxy-2,2,16,16-tetrafluoro-Δ⁶-19ξ-hydroxy-PGF₁, methyl ester
9-deoxy-6ξ,9α-epoxy-Δ⁷-19ξ-hydroxy-PGF₁, methyl ester
9-deoxy-6ξ,9α-epoxy-Δ⁷-16,16-dimethyl-19ξ-hydroxy-PGF₁, methyl ester
9-deoxy-6ξ,9α-epoxy-Δ⁷-16,16-difluoro-19ξ-hydroxy-PGF₁, methyl ester
9-deoxy-6ξ,9α-epoxy-Δ⁷-15-methyl-19ξ-hydroxy-PGF₁, methyl ester
9-deoxy-6ξ,9α-epoxy-Δ⁷-13,14-cis-19ξ-hydroxy-PGF₁, methyl ester
9-deoxy-6ξ,9α-epoxy-Δ⁷-13,14-didehydro-19ξ-hydroxy-PGF₁, methyl ester
9-deoxy-6ξ,9α-epoxy-Δ⁷-13,14-didehydro-16,16-difluoro-19ξ-hydroxy-PGF₁, methyl ester
9-deoxy-6ξ,9α-epoxy-Δ⁷-13,14-dihydro-19ξ-hydroxy-PGF₁, methyl ester
9-deoxy-6ξ,9α-epoxy-Δ⁷-13,14-dihydro-16,16-difluoro-19ξ-hydroxy-PGF₁, methyl ester
9-deoxy-6ξ,9α-epoxy-Δ⁷-11-deoxy-19ξ-hydroxy-PGF₁, methyl ester
9-deoxy-6ξ,9α-epoxy-Δ⁷-11-deoxy-16,16-difluoro-19ξ-hydroxy-PGF₁, methyl ester
9-deoxy-6ξ,9α-epoxy-Δ⁷-11-deoxy-11α-hydroxymethyl-19ξ-hydroxy-PGF₁, methyl ester
(2E)-9-deoxy-6ξ,9α-epoxy-Δ²,Δ⁷-19ξ-hydroxy-PGF₁, methyl ester
(2E)-9-deoxy-6ξ,9α-epoxy-Δ²,Δ⁷-16,16-difluoro-19ξ-hydroxy-PGF₁, methyl ester
(5E)-6a-carba-9-deoxy-6,9α-epoxy-Δ⁵-19ξ-hydroxy-PGF₁, methyl ester
(5E)-6a-carba-9-deoxy-6,9α-epoxy-Δ⁵-16,16-dimethyl-19ξ-hydroxy-PGF₁, methyl ester
(5E)-6a-carba-9-deoxy-6,9α-epoxy-Δ⁵-16,16-difluoro-19ξ-hydroxy-PGF₁, methyl ester
(5E)-6a-carba-9-deoxy-6,9α-epoxy-Δ⁵-15-methyl-19ξ-hydroxy-PGF₁, methyl ester
(5E)-6a-carba-9-deoxy-6,9α-epoxy-Δ⁵-13,14-cis-19ξ-hydroxy-PGF₁, methyl ester
(5E)-6a-carba-9-deoxy-6,9α-epoxy-Δ⁵-13,14-didehydro-19ξ-hydroxy-PGF₁, methyl ester
(5E)-6a-carba-9-deoxy-6,9α-epoxy-Δ⁵-13,14-didehydro-16,16-difluoro-19ξ-hydroxy-PGF₁, methyl ester
(5E)-6a-carba-9-deoxy-6,9α-epoxy-Δ⁵-13,14-dihydro-19ξ-hydroxy-PGF₁, methyl ester
(5E)-6a-carba-9-deoxy-6,9α-epoxy-Δ⁵-13,14-dihydro-16,16-difluoro-19ξ-hydroxy-PGF₁, methyl ester
(5E)-6a-carba-9-deoxy-6,9α-epoxy-Δ⁵-11-deoxy-19ξ-hydroxy-PGF₁, methyl ester
(5E)-6a-carba-9-deoxy-6,9α-epoxy-Δ⁵-11-deoxy-16,16-difluoro-19ξ-hydroxy-PGF₁, methyl ester
(5E)-6a-carba-9-deoxy-6,9α-epoxy-Δ⁵-2,2-difluoro-19ξ-hydroxy-PGF₁, methyl ester
(5E)-6a-carba-9-deoxy-6,9α-epoxy-Δ⁵-2,2,16,16-tetrafluoro-19ξ-hydroxy-PGF₁, methyl ester
(2E,5E)-6a-carba-9-deoxy-6,9α-epoxy-Δ²,Δ⁵-19ξ-hydroxy-PGF₁, methyl ester
(2E,5E)-6a-carba-9-deoxy-6,9α-epoxy-Δ²,Δ⁵-16,16-difluoro-19ξ-hydroxy-PGF₁, methyl ester
6-oxo-19ξ-hydroxy-PGF₁α, methyl ester
6-oxo-16,16-dimethyl-19ξ-hydroxy-PGF₁α, methyl ester
6-oxo-16,16-difluoro-19ξ-hydroxy-PGF₁α, methyl ester
6-oxo-15-methyl-19ξ-hydroxy-PGF₁α, methyl ester
6-oxo-13,14-cis-19ξ-hydroxy-PGF₁α, methyl ester
6-oxo-13,14-didehydro-19ξ-hydroxy-PGF₁α, methyl ester
6-oxo-13,14-didehydro-16,16-difluoro-19ξ-hydroxy-PGF₁α, methyl ester
6-oxo-13,14-dihydro-19ξ-hydroxy-PGF₁α, methyl ester
6-oxo-13,14-dihydro-16,16-difluoro-19Ξ-hydroxy-PGF₁α, methyl ester
6-oxo-11-deoxy-19ξ-hydroxy-PGF₁α, methyl ester
6-oxo-11-deoxy-16,16-difluoro-19ξ-hydroxy-PGF₁α, methyl ester
6-oxo-11-deoxy-11α-hydroxymethyl-19ξ-hydroxy-PGF₁α, methyl ester
6-oxo-2,2-difluoro-19ξ-hydroxy-PGF₁α, methyl ester
6-oxo-2,2,16,16-tetrafluoro-19ξ-hydroxy-PGF₁α, methyl ester
(2E)-6-oxo-Δ²-19ξ-hydroxy-PGF₁α, methyl ester
(2E)-6-oxo-Δ²-16,16-difluoro-19ξ-hydroxy-PGF₁α, methyl ester
6-oxo-9-deoxy-9-hydroxymethyl-19ξ-hydroxy-PGF₁α, methyl ester
5-oxo-19ξ-hydroxy-PGF₁α, methyl ester
5-oxo-16,16-dimethyl-19ξ-hydroxy-PGF₁α, methyl ester
5-oxo-16,16-difluoro-19ξ-hydroxy-PGF₁α, methyl ester
5-oxo-15-methyl-19ξ-hydroxy-PGF₁α, methyl ester
5-oxo-13,14-cis-19ξ-hydroxy-PGF₁α, methyl ester
5-oxo-13,14-didehydro-19ξ-hydroxy-PGF₁α, methyl ester
5-oxo-13,14-dihydro-19ξ-hydroxy-PGF₁α, methyl ester
5-oxo-13,14-dihydro-16,16-difluoro-19ξ-hydroxy-PGF₁α, methyl ester
5-oxo-2,2-difluoro-19ξ-hydroxy-PGF₁α, methyl ester
(2E)-5-oxo-Δ²-19ξ-hydroxy-PGF₁α, methyl ester
(2E)-5-oxo-Δ²-16,16-difluoro-19ξ-hydroxy-PGF₁α, methyl ester
(2E)-5-oxo-Δ²-13,14-dihydro-19ξ-hydroxy-PGF₁α, methyl ester B. wherein $R_1$ is —CH₂OH (5Z)-2-decarboxy-2-hydroxymethyl-9-deoxy-6,9α-epoxy-Δ⁵-19ξ-hydroxy-PGF₁
(5Z)-2-decarboxy-2-hydroxymethyl-9-deoxy-6,9α-epoxy-Δ⁵-16,16-difluoro-19ξ-hydroxy-PGF₁
2-decarboxy-2-hydroxymethyl-9-deoxy-6ξ,9α-epoxy-19ξ-hydroxy-PGF₁
2-decarboxy-2-hydroxymethyl-9-deoxy-6ξ,9α-epoxy-16,16-difluoro-19ξ-hydroxy-PGF₁
2-decarboxy-2-hydroxymethyl-9-deoxy-6ξ,9α-epoxy-6ξ,19ξ-dihydroxy-PGF₁
2-decarboxy-2-hydroxymethyl-9-deoxy-6ξ,9α-epoxy-6ξ,19ξ-dihydroxy-16,16-difluoro-PGF₁
(4Z)-2-decarboxy-2-hydroxymethyl-9-deoxy-5,9α-epoxy-Δ⁴-19ξ-hydroxy-PGF₁
(4Z)-2-decarboxy-2-hydroxymethyl-9-deoxy-5,9α-epoxy-Δ⁴-16,16-difluoro-19ξ-hydroxy-PGF₁
(2E,4Z)-2-decarboxy-2-hydroxymethyl-9-deoxy-5,9α-epoxy-Δ²,Δ⁴-19ξ-hydroxy-PGF₁
2-decarboxy-2-hydroxymethyl-9-deoxy-5,9α-epoxy-19ε-hydroxy-PGF₁
2-decarboxy-2-hydroxymethyl-9-deoxy-5ξ,9α-epoxy-16,16-difluoro-19ξ-hydroxy-PGF₁
(5Z)-2-decarboxy-2-hydroxymethyl-9-deoxy-6,9α-epoxymethano-Δ⁵-19ξ-hydroxy-PGF₁
(5Z)-2-decarboxy-2-hydroxymethyl-9-deoxy-6,9α-epoxymethano-Δ⁵-16,16-difluoro-19ξ-hydroxy-PGF₁
2-decarboxy-2-hydroxymethyl-9-deoxy-6ξ,9α-epoxymethano-19ξ-hydroxy-PGF₁

2-decarboxy-2-hydroxymethyl-9-deoxy-6ξ,9α-epoxymethano-16,16-difluoro-19ξ-hydroxy-PGF$_1$
2-decarboxy-2-hydroxymethyl-9-deoxy-6ξ,9α-epoxy-5ξ,19ξ-dihydroxy-PGF$_1$
2-decarboxy-2-hydroxymethyl-9-deoxy-6ξ,9α-epoxy-5ξ,19ξ-dihydroxy-16,16-difluoro-PGF$_1$
(4E)-2-decarboxy-2-hydroxymethyl-9-deoxy-6ξ,9α-epoxy-Δ$^4$-19ξ-hydroxy-PGF$_1$
(4E)-2-decarboxy-2-hydroxymethyl-9-deoxy-6ξ,9α-epoxy-Δ$^4$-16,16-difluoro-19ξ-hydroxy-PGF$_1$
2-decarboxy-2-hydroxymethyl-9-deoxy-6ξ,9α-epoxy-6ξ-methoxy-19ξ-hydroxy-PGF$_1$
2-decarboxy-2-hydroxymethyl-9-deoxy-6ξ,9α-epoxy-6ξ-methoxy-16,16-difluoro-19ξ-hydroxy-PGF$_1$
2-decarboxy-2-hydroxymethyl-9-deoxy-6ξ,9α-epoxy-4-oxo-19ξ-hydroxy-PGF$_1$
2-decarboxy-2-hydroxymethyl-9-deoxy-6ξ,9α-epoxy-4-oxo-16,16-difluoro-19ξ-hydroxy-PGF$_1$
2-decarboxy-2-hydroxymethyl-9-deoxy-6ξ,9α-epoxy-Δ$^6$-19ξ-hydroxy-PGF$_1$
2-decarboxy-2-hydroxymethyl-9-deoxy-6ξ,9α-epoxy-Δ$^6$-16,16-difluoro-19ξ-hydroxy-PGF$_1$
2-decarboxy-2-hydroxymethyl-9-deoxy-6ξ,9α-epoxy-Δ$^7$-19ξ-hydroxy-PGF$_1$
2-decarboxy-2-hydroxymethyl-9-deoxy-6Ξ,9α-epoxy-Δ$^7$-16,16-difluoro-19ξ-hydroxy-PGF$_1$
(2E)-2-decarboxy-2-hydroxymethyl-9-deoxy-6ξ,9α-epoxy-Δ$^2$,Δ$^7$-19ξ-hydroxy-PGF$_1$
(5E)-2-decarboxy-2-hydroxymethyl-6a-carba-9-deoxy-6,9α-epoxy-Δ$^5$-19ξ-hydroxy-PGF$_1$
(5E)-2-decarboxy-2-hydroxymethyl-6a-carba-9-deoxy-6,9α-epoxy-Δ$^5$-16,16-difluoro-19ξ-hydroxy-PGF$_1$
(2E,5E)-2-decarboxy-2-hydroxymethyl-6a-carba-9-deoxy-6,9α-epoxy-Δ$^2$,Δ$^5$-19ξ-hydroxy-PGF$_1$
2-decarboxy-2-hyroxymethyl-6-oxo-19ξ-hydroxy-PGF$_1$
2-decarboxy-2-hydroxymethyl-6-oxo-16,16-difluoro-19ξ-hydroxy-PGF$_1$
2-decarboxy-2-hydroxymethyl-5-oxo-19ξ-hydroxy-PGF$_1$
2-decarboxy-2-hydroxymethyl-5-oxo-16,16-difluoro-19ξ-hydroxy-PGF$_1$
  C. wherein R$_1$ is —C(O)—NH$_2$
(5Z)-9-deoxy-6,9α-epoxy-Δ$^5$-19ξ-hydroxy-PGF$_1$, amide
(5Z)-9-deoxy-6,9α-epoxy-Δ$^5$-16,16difluoro-19ξ-hydroxy-PGF$_1$, amide
9-deoxy-6ξ,9α-epoxy-19ξ-hydroxy-PGF$_1$, amide
9-deoxy-6ξ,9α-epoxy-16,16-difluoro-19ξ-hydroxy-PGF$_1$, amide
(2E)-9-deoxy-6ξ,9α-epoxy-Δ$^2$-19ξ-hydroxy-PGF$_1$, amide
9-deoxy-6ξ,9α-epoxy-6ξ,19ξ-dihydroxy-PGF$_1$, amide
9-deoxy-6ξ,9α-epoxy-6ξ,19ξ-dihydroxy-16,16-difluoro-PGF$_1$, amide
(4Z)-9-deoxy-5,9α-epoxy-Δ$^4$-19ξ-hydroxy-PGF$_1$, amide
(4Z)-9-deoxy-5,9α-epoxy-Δ$^4$-16,16-difluoro-19ξ-hydroxy-PGF$_1$, amide
(2E,4Z)-9-deoxy-5,9α-epoxy-Δ$^2$,Δ$^4$-19ξ-hydroxy-PGF$_1$, amide
9-deoxy-5ξ,9α-epoxy-19ξ-hydroxy-PGF$_1$, amide
9-deoxy-5ξ,9α-epoxy-16,16-difluoro-19ξ-hydroxy-PGF$_1$, amide
(2E)-9-deoxy-5ξ,9α-epoxy-Δ$^2$-19ξ-hydroxy-PGF$_1$, amide
(5Z)-9-deoxy-6,9α-epoxymethano-Δ$^5$-19ξ-hydroxy-PGF$_1$, amide
(5Z)-9-deoxy-6,9α-epoxymethano-Δ$^5$-16,16-difluoro-19ξ-hydroxy-PGF$_1$, amide
9-deoxy-6ξ,9α-epoxymethano-19ξ-hydroxy-PGF$_1$, amide
9-deoxy-6ξ,9α-epoxymethano-16,16-difluoro-19ξ-hydroxy-PGF$_1$, amide
(2E)-9-deoxy-6ξ,9α-epoxymethano-Δ$^2$-19ξ-hydroxy-PGF$_1$,
9-deoxy-6ξ,9α-epoxy-5ξ,19ξ-dihydroxy-PGF$_1$, amide
9-deoxy-6ξ,9α-epoxy-5ξ,19ξ-dihydroxy-16,16-difluoro-PGF$_1$, amide
(2E)-9-deoxy-6ξ,9α-epoxy-Δ$^2$-5ξ,19ξ-dihydroxy-PGF$_1$, amide
(4E)-9-deoxy-6ξ,9α-epoxy-Δ$^4$-19ξ-hydroxy-PGF$_1$, amide
(4E)-9-deoxy-6ξ,9α-epoxy-Δ$^4$-16,16-difluoro-19ξ-hydroxy-PGF$_1$, amide
(2E,4E)-9-deoxy-6ξ,9α-epoxy-Δ$^2$,Δ$^4$-19ξ-hydroxy-PGF$_1$, amide
9-deoxy-6ξ,9α-epoxy-6ξ-methoxy-19ξ-hydroxy-PGF$_1$, amide
9-deoxy-6ξ,9α-epoxy-6ξ-methoxy-16,16-difluoro-19ξ-hydroxy-PGF$_1$, amide
9-deoxy-6ξ,9α-epoxy-4-oxo-19ξ-hydroxy-PGF$_1$, amide
9-deoxy-6ξ,9α-epoxy-4-oxo-16,16-difluoro-19ξ-hydroxy-PGF$_1$, amide
9-deoxy-6ξ,9α-epoxy-Δ$^6$-19ξ-hydroxy-PGF$_1$, amide
9-deoxy-6ξ,9α-epoxy-Δ$^6$-16,16-difluoro-19ξ-hydroxy-PGF$_1$, amide
9-deoxy-6ξ,9α-epoxy-Δ$^7$-19ξ-hydroxy-PGF$_1$, amide
9-deoxy-6ξ,9α-epoxy-Δ$^7$-16,16-difluoro-19ξ-hydroxy-PGF$_1$, amide
(2E)-9-deoxy-6ξ,9α-epoxy-Δ$^2$,Δ$^7$-19ξ-hydroxy-PGF$_1$, amide
(5E)-6a-carba-9-deoxy-6,9α-epoxy-Δ$^5$-19ξ-hydroxy-PGF$_1$, amide
(5E)-6a-carba-9-deoxy-6,9α-epoxy-Δ$^5$-16,16-difluoro-19ξ-hydroxy-PGF$_1$, amide
(2E,5E)-6a-carba-9-deoxy-6,9α-epoxy-Δ$^2$,Δ$^5$-19ξ-hydroxy-PGF$_1$, amide
6-oxo-19ξ-hydroxy-PGF$_{1α}$, amide
6-oxo-16,16-difluoro-19Ξ-hydroxy-PGF$_{1α}$, amide
5-oxo-19ξ-hydroxy-PGF$_{1α}$, amide
5-oxo-16,16-difluoro-PGF$_{1α}$, amide Using the appropriate starting materials in which R$_{13}$ is methyl, there are likewise prepared the corresponding compounds wherein R$_{13}$ is methyl as represented by formula 15, for example:

A. wherein R$_1$ is —COOR$_3$
(5Z)-9-deoxy-6,9α-epoxy-Δ$^5$-19-hydroxy-19-methyl-PGF$_1$, methyl ester
(5Z)-9-deoxy-6,9α-epoxy-Δ$^5$-16,16-dimethyl-19-hydroxy-19-methyl-PGF$_1$, methyl ester
and other 19-hydroxy-19-methyl compounds corresponding to the above 19-hydroxy compounds for this class and for those below.

B. wherein R$_1$ is —CH$_2$OH
(5Z)-2-decarboxy-2-hydroxymethyl-9-deoxy-6,9α-epoxy-Δ$^5$-19-hydroxy-19-methyl-PGF$_1$
(5Z)-2-decarboxy-2-hydroxymethyl-9-deoxy-6,9α-epoxy-Δ$^5$-16,16-difluoro-19-hydroxy-19-methyl-PGF$_1$
  C. wherein R$_1$ is —C(O)—NH$_2$ (5Z)-9-deoxy-6,9α-epoxy-Δ⁵-19-hydroxy-19-methyl-PGF₁, amide
(5Z)-9-deoxy-6,9α-epoxy-Δ⁵-16,16-difluoro-19-hydroxy-19-methyl-PGF₁, amide.
FORMULAS
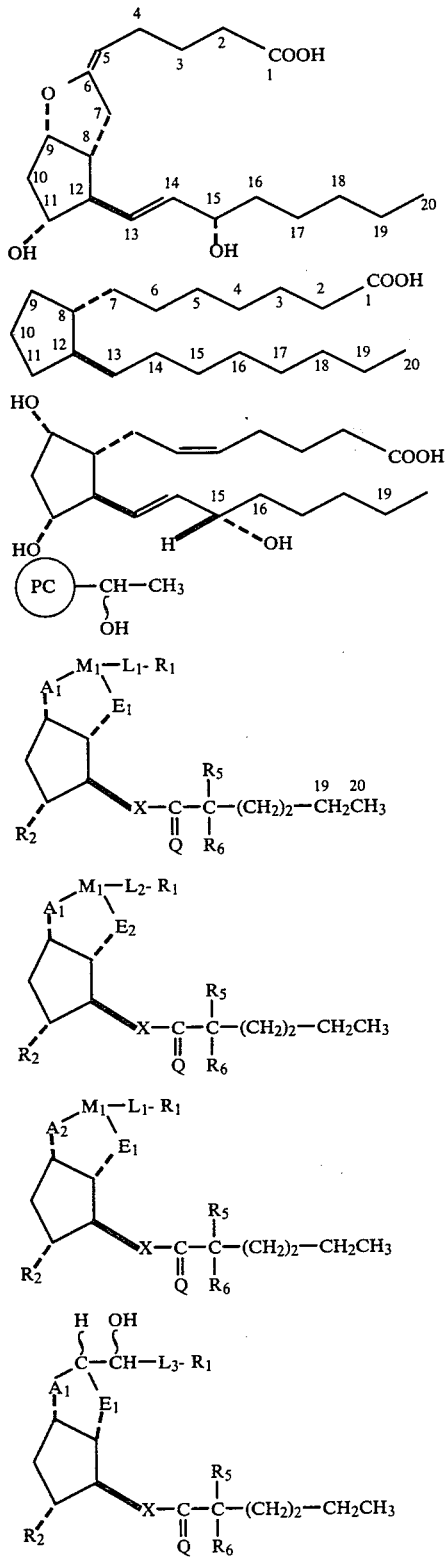
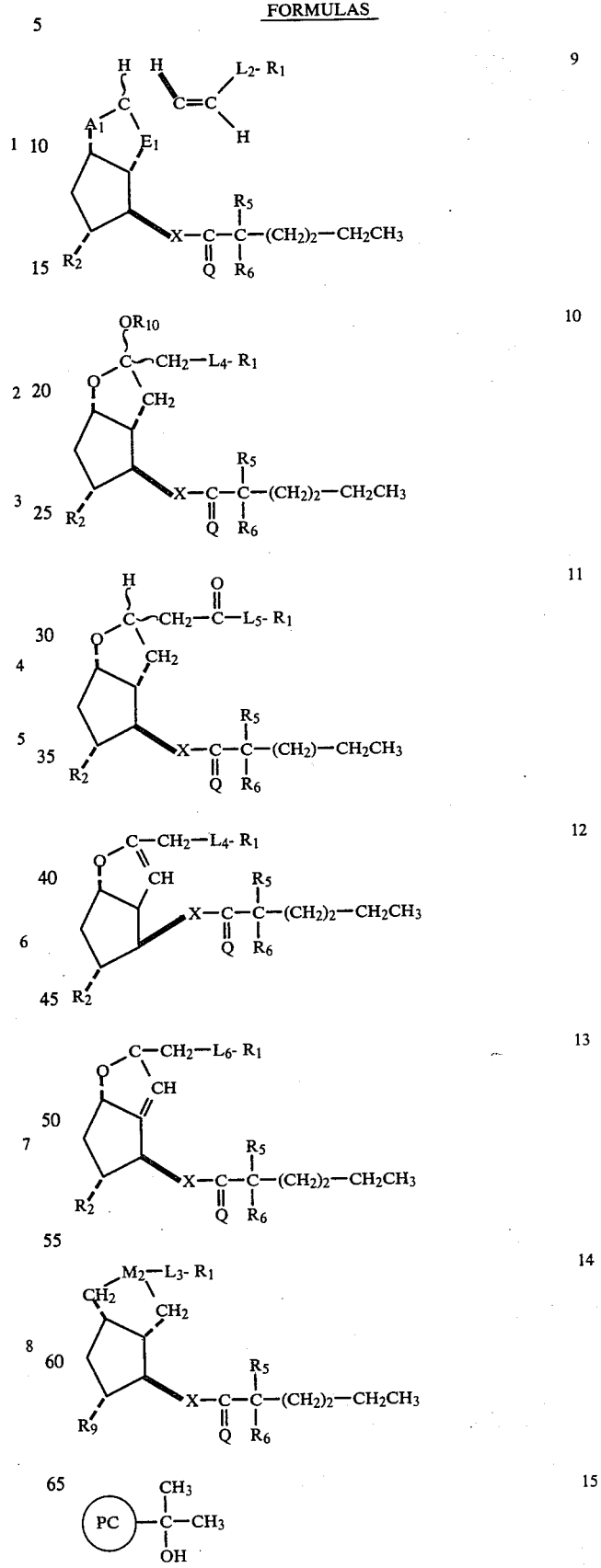

-continued
FORMULAS
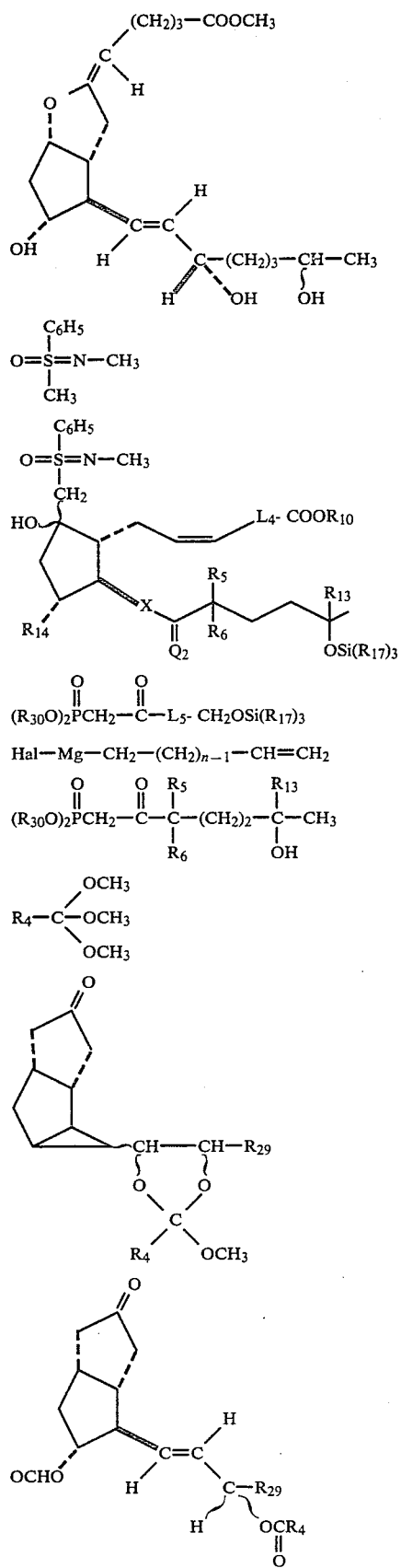
228
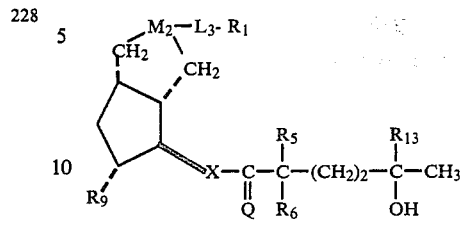
229
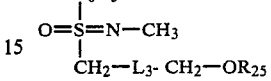
230
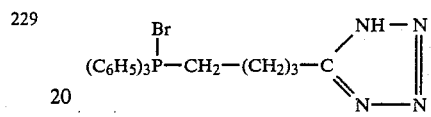
231
232
233
-continued
FORMULAS
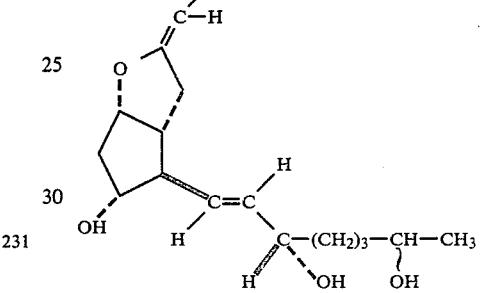   237
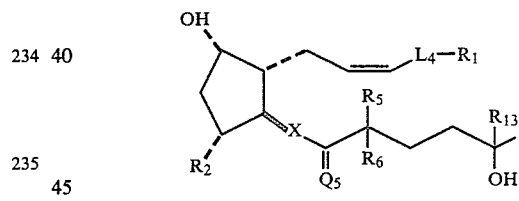   238
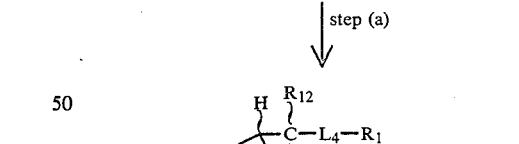   239
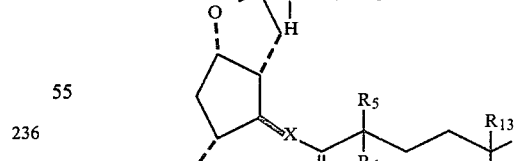   240
CHART 1

-continued
CHART 1
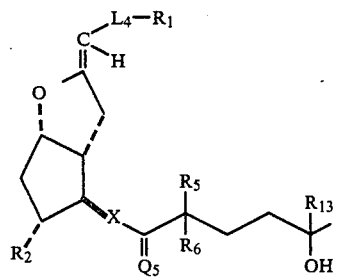
18
CHART 2
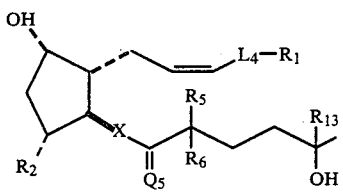
16
step (a)
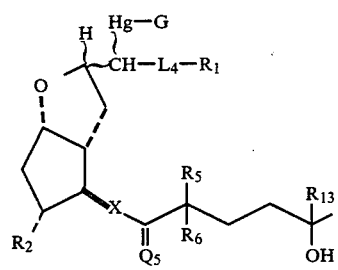
19
step (b)
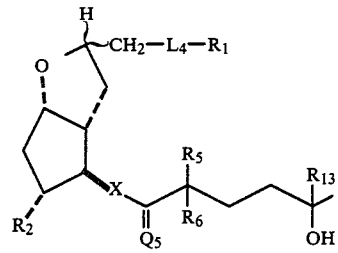
20
CHART 3
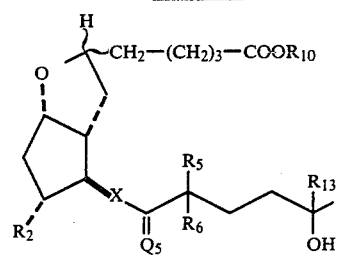
21
step (a)
-continued
CHART 3
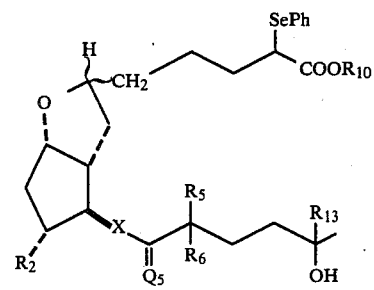
22
step (b)
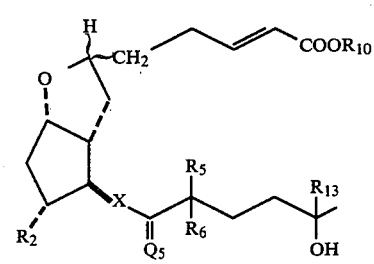
23
step (c)
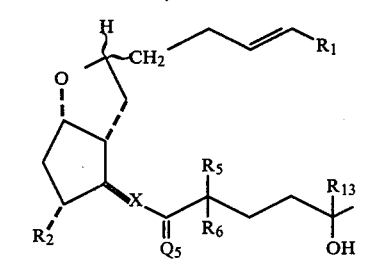
24
CHART 4
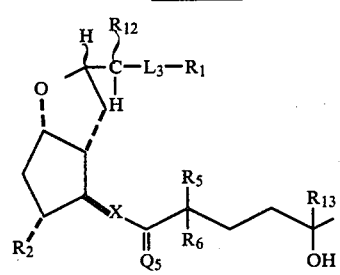
25
step (a)
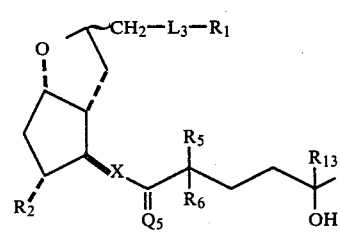
26

CHART 5
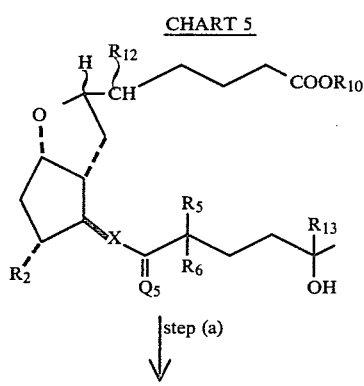
27
step (a)
-continued
CHART 5
step (c)
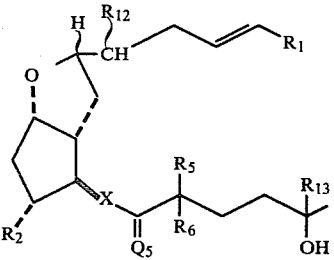
28
CHART 6
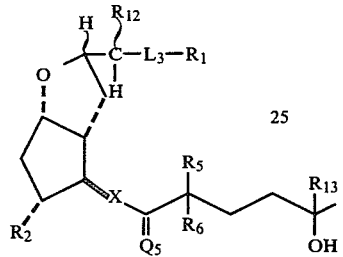
step (a)
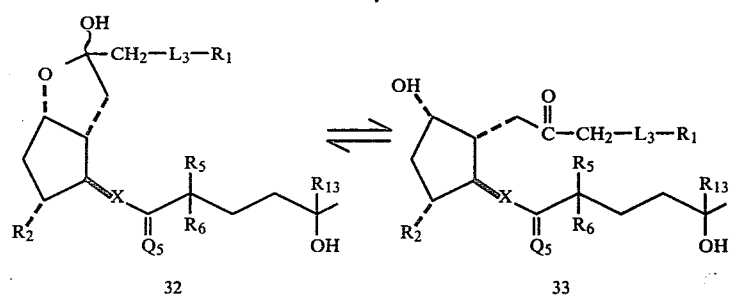
32  33
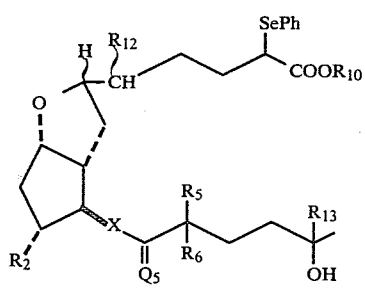
step (b)
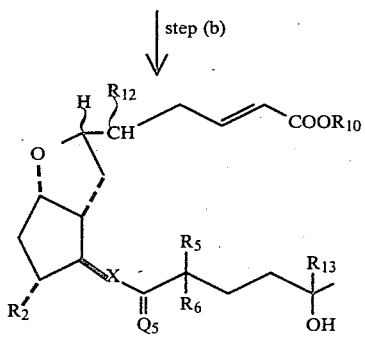
29
CHART 7
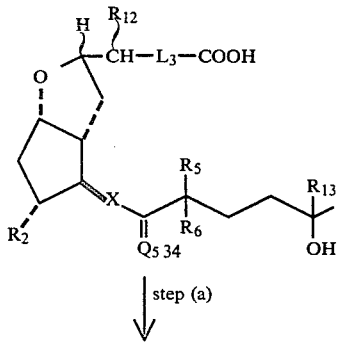
34
step (a)

CHART 7 -continued
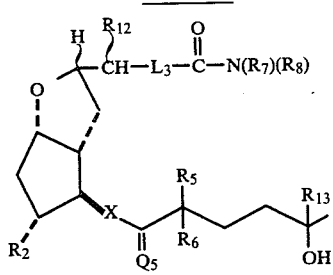
35
↓ step (b)
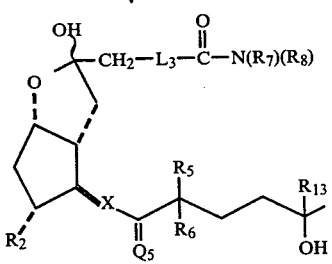
36
⇅
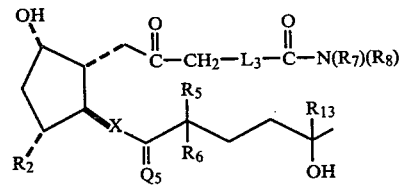
37
CHART 8
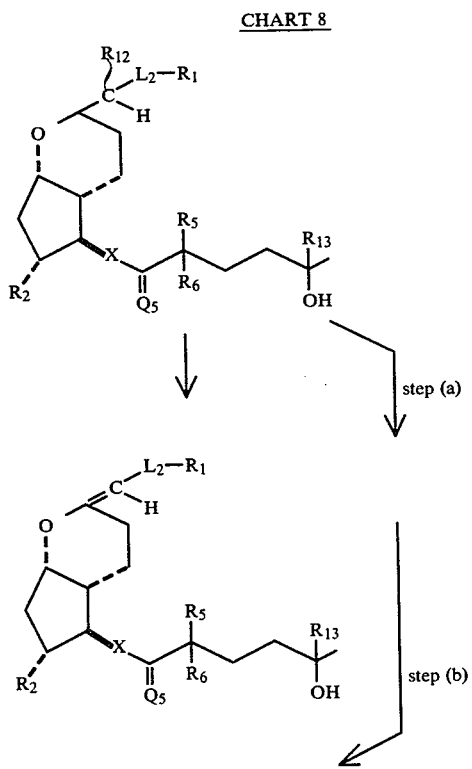
38
↓ step (a)
39
CHART 8 -continued
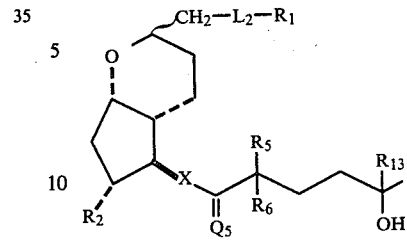
40
CHART 9
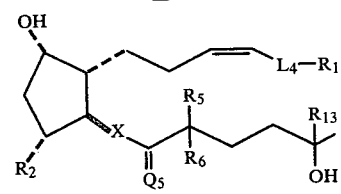
41
↓ step (a)
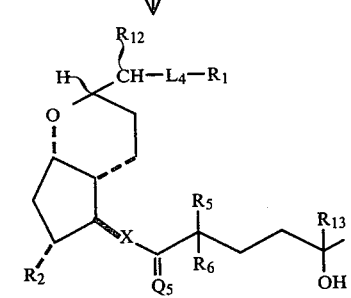
42
CHART 10
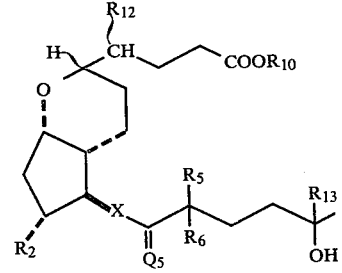
43
↓ step (a)
44
↓ step (b)

4,225,508
-continued
CHART 10
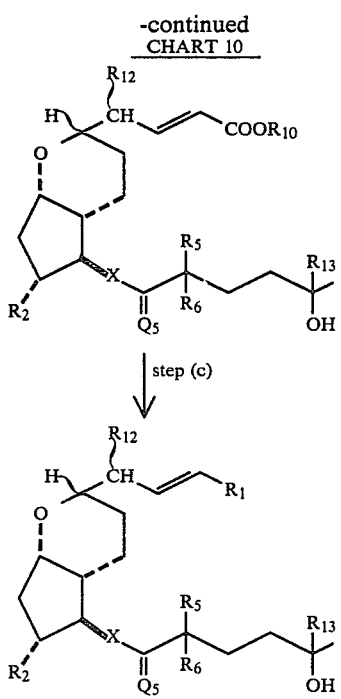
CHART 11
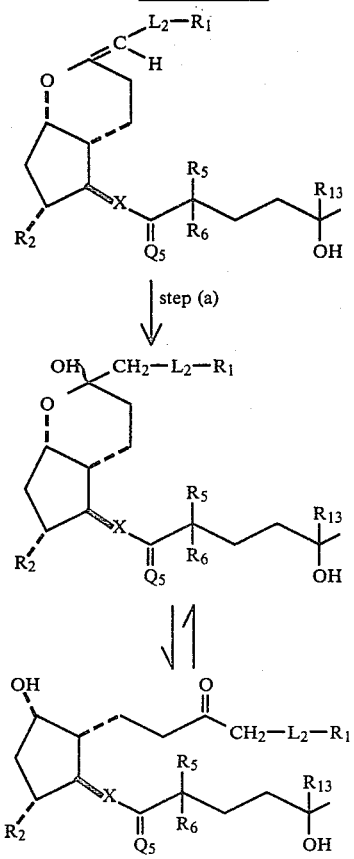
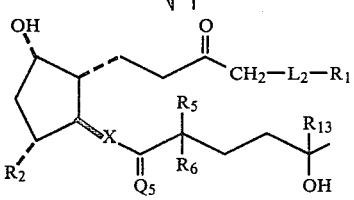
CHART 12
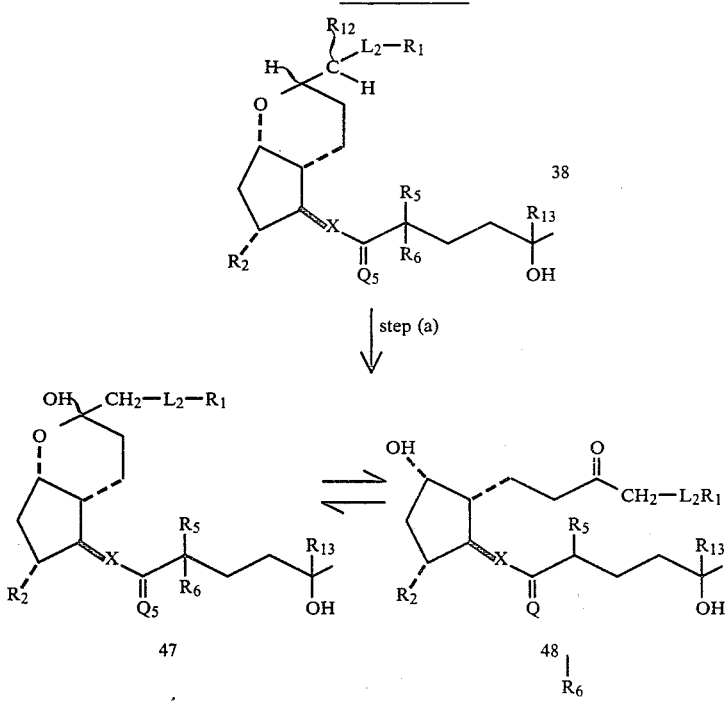

CHART 13
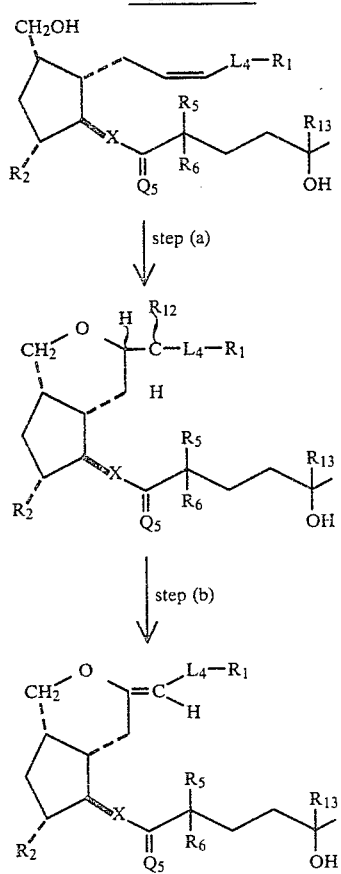
CHART 14
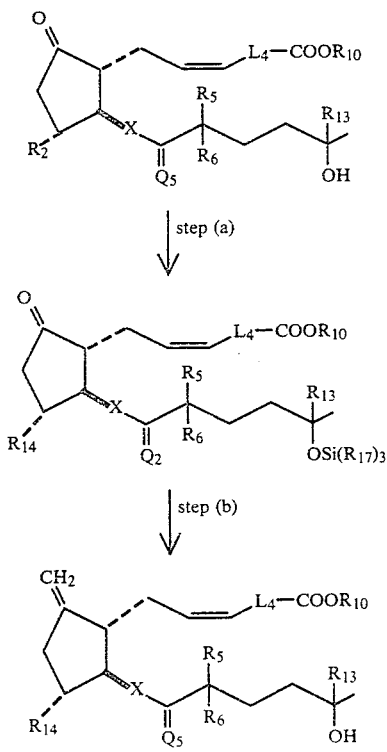
CHART 14 -continued
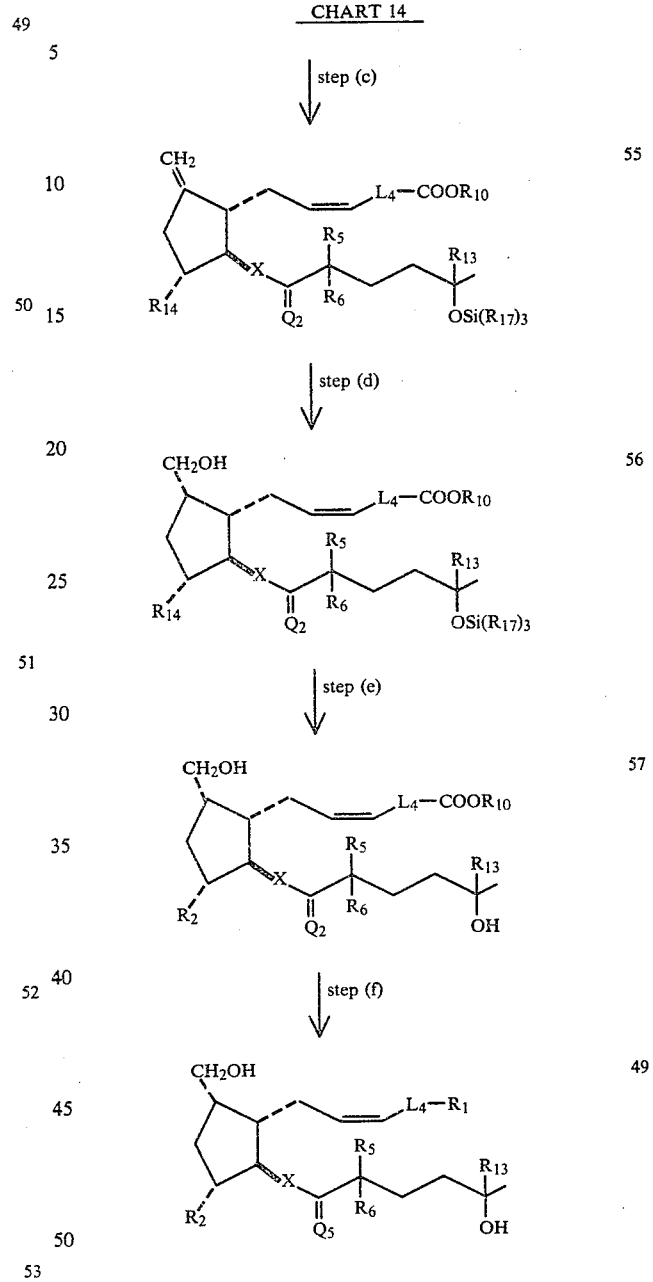
CHART 15
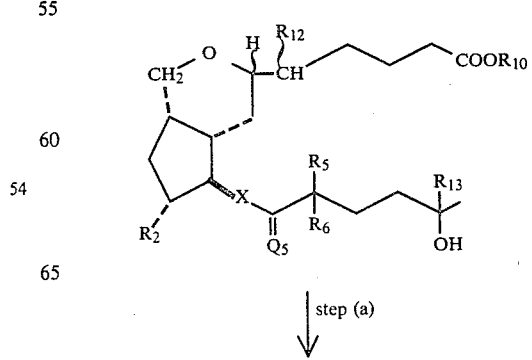
step (a)

-continued
CHART 15
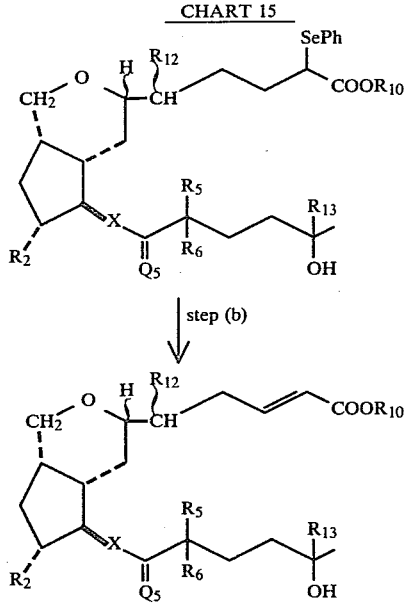
step (b)
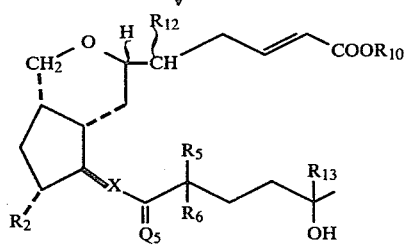
CHART 16
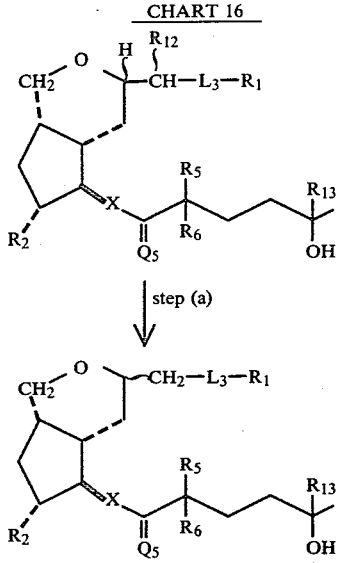
step (a)
CHART 17
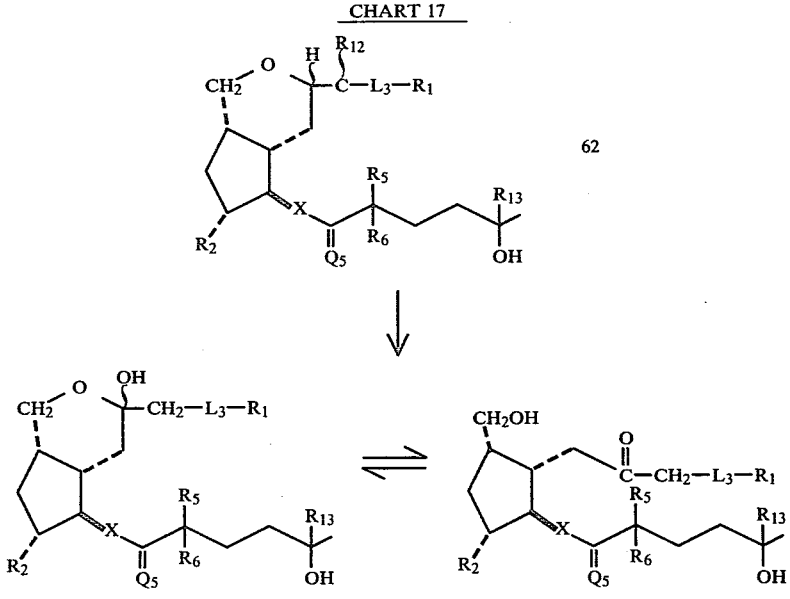
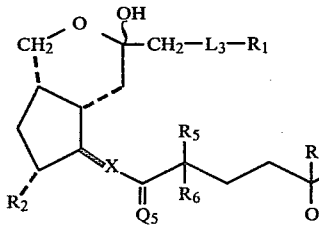
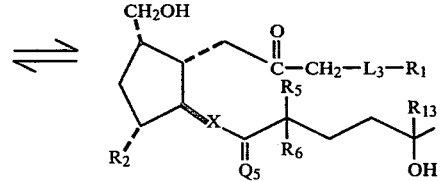
step (c)
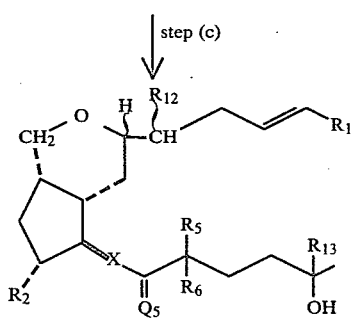
CHART 18
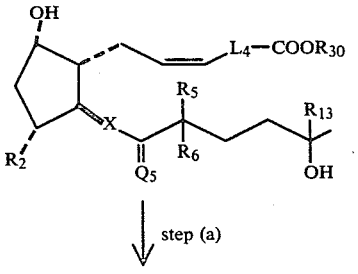
step (a)

-continued
CHART 18
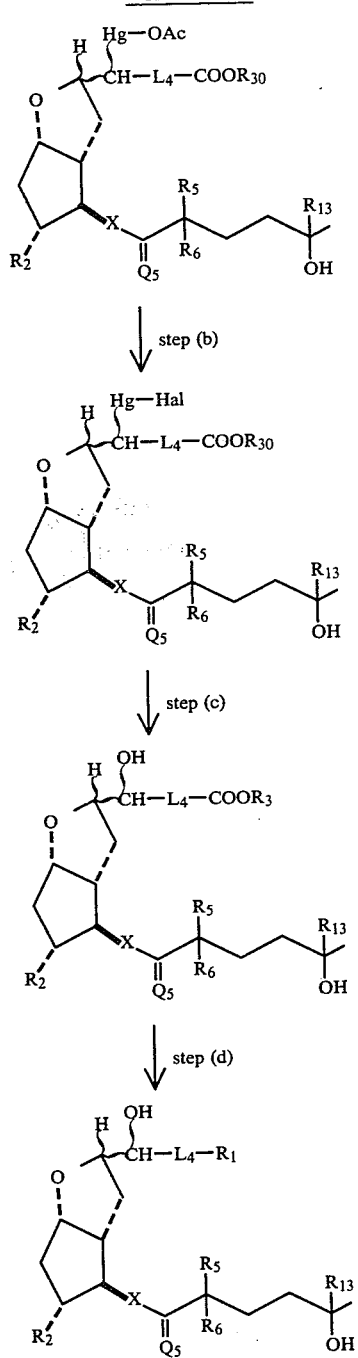
CHART 19
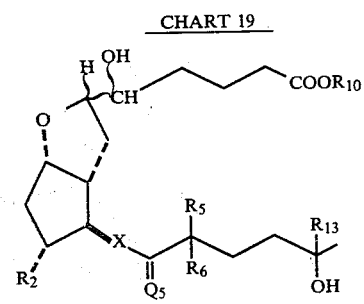
-continued
CHART 19
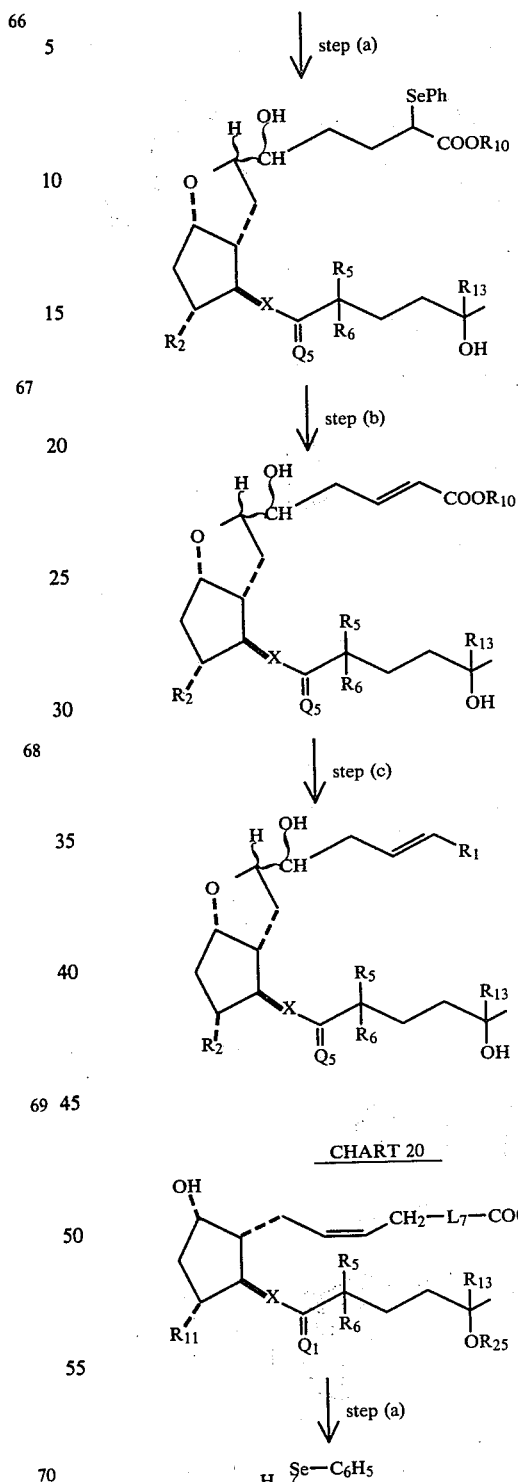
CHART 20
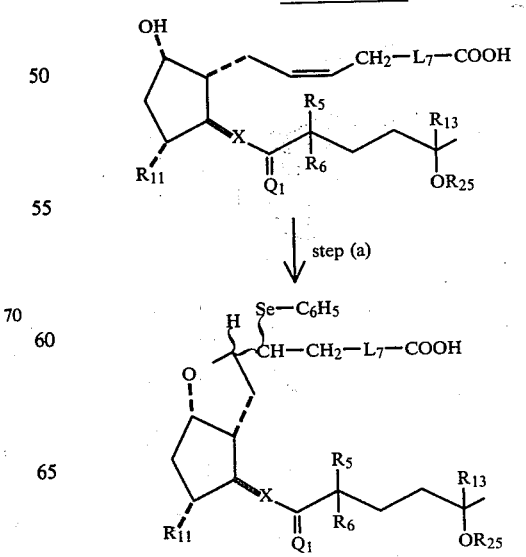

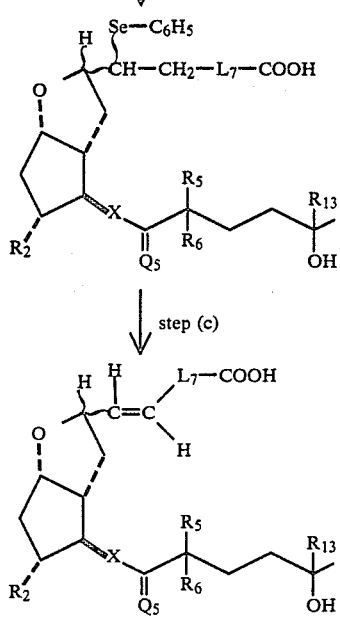
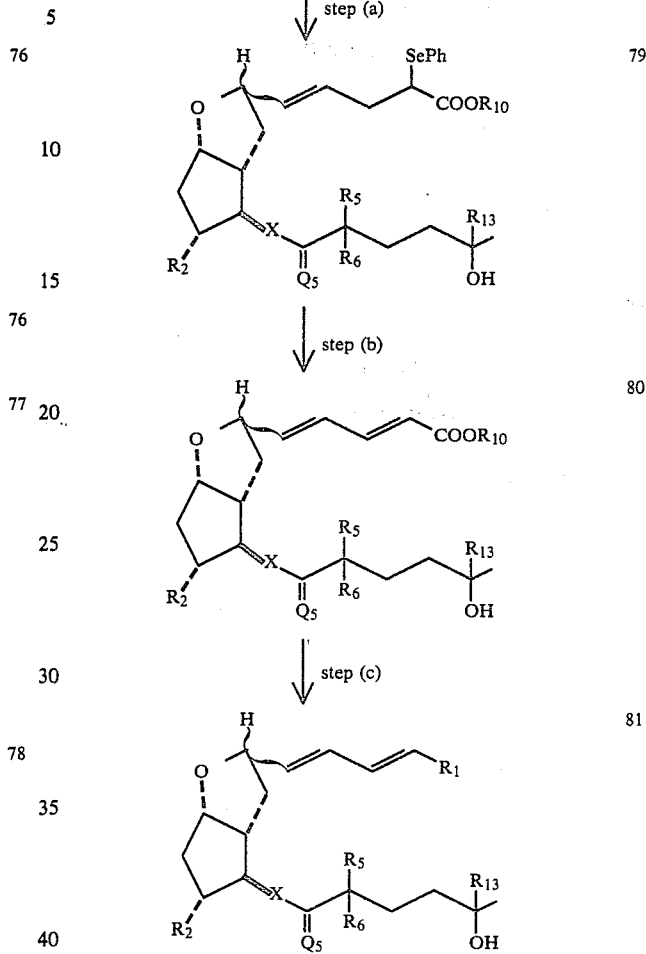
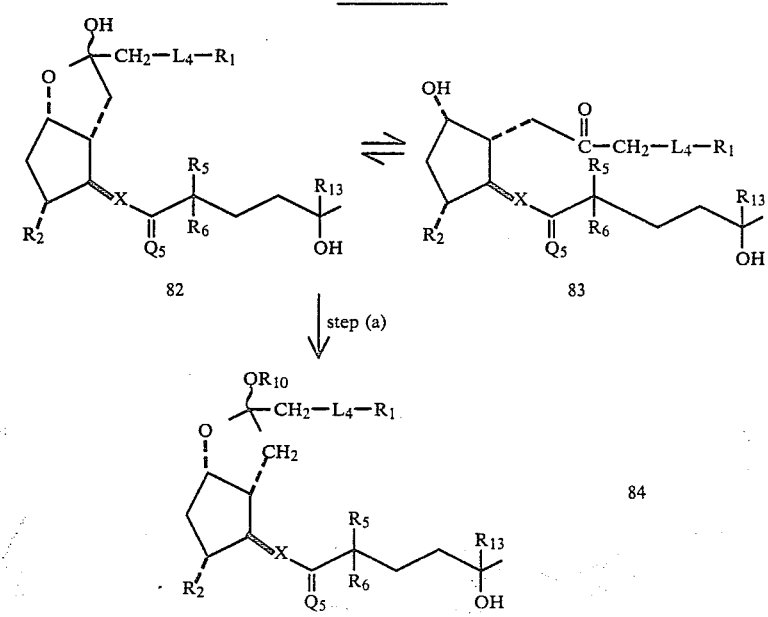

CHART 22
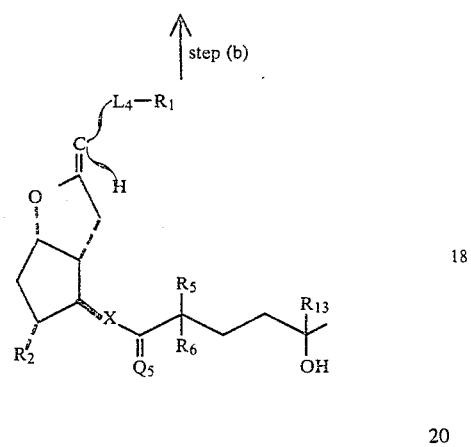
CHART 23
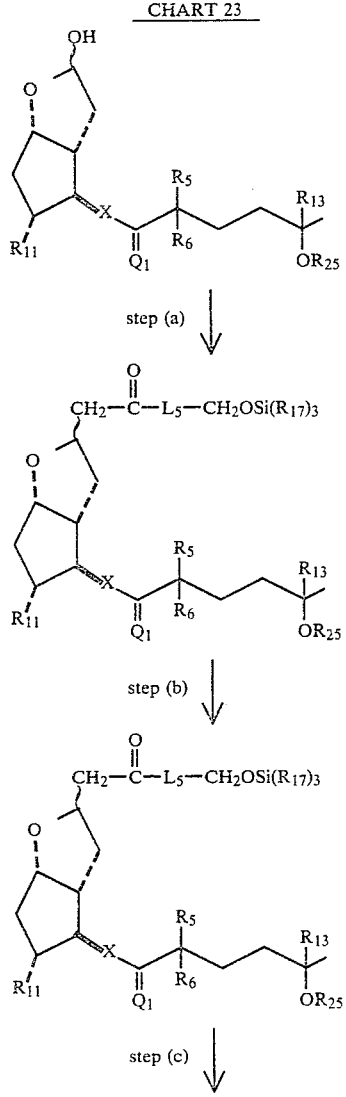
-continued
CHART 23
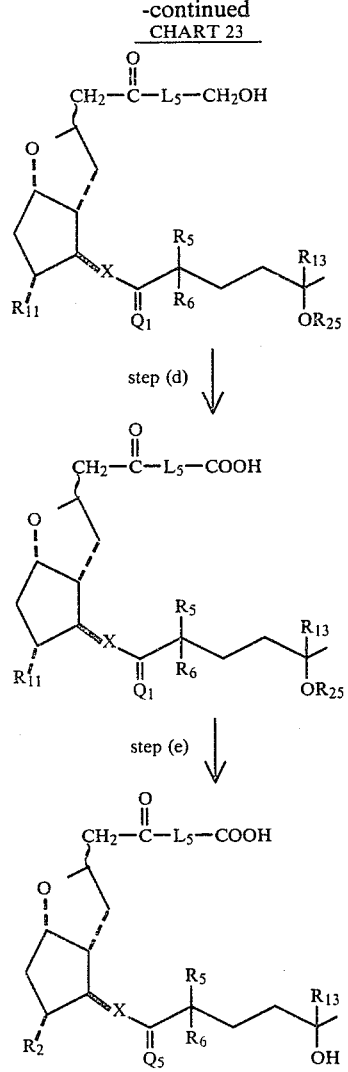

CHART 24
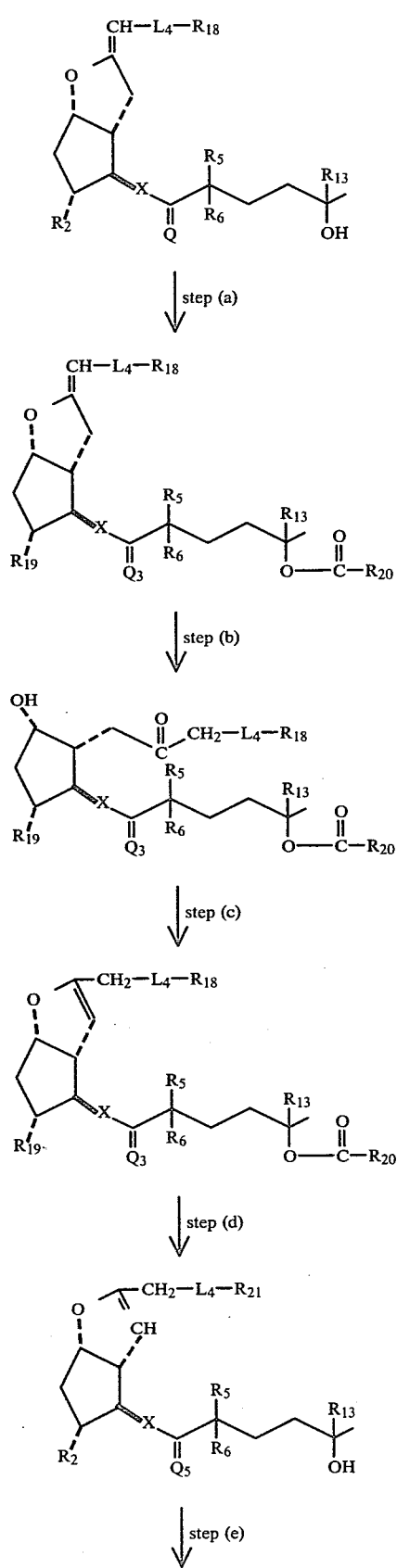
-continued
CHART 24
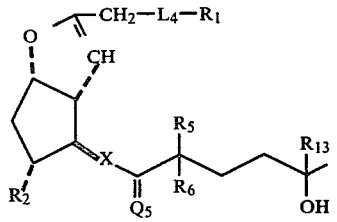
CHART 25
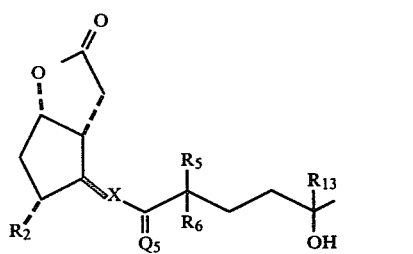

-continued
CHART 25
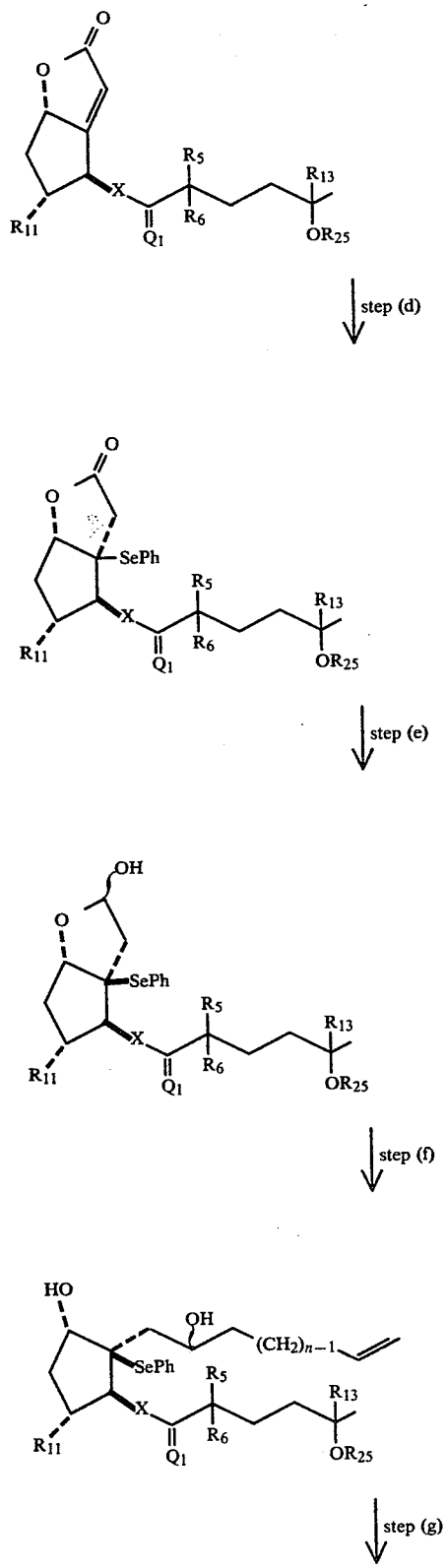
-continued
CHART 25
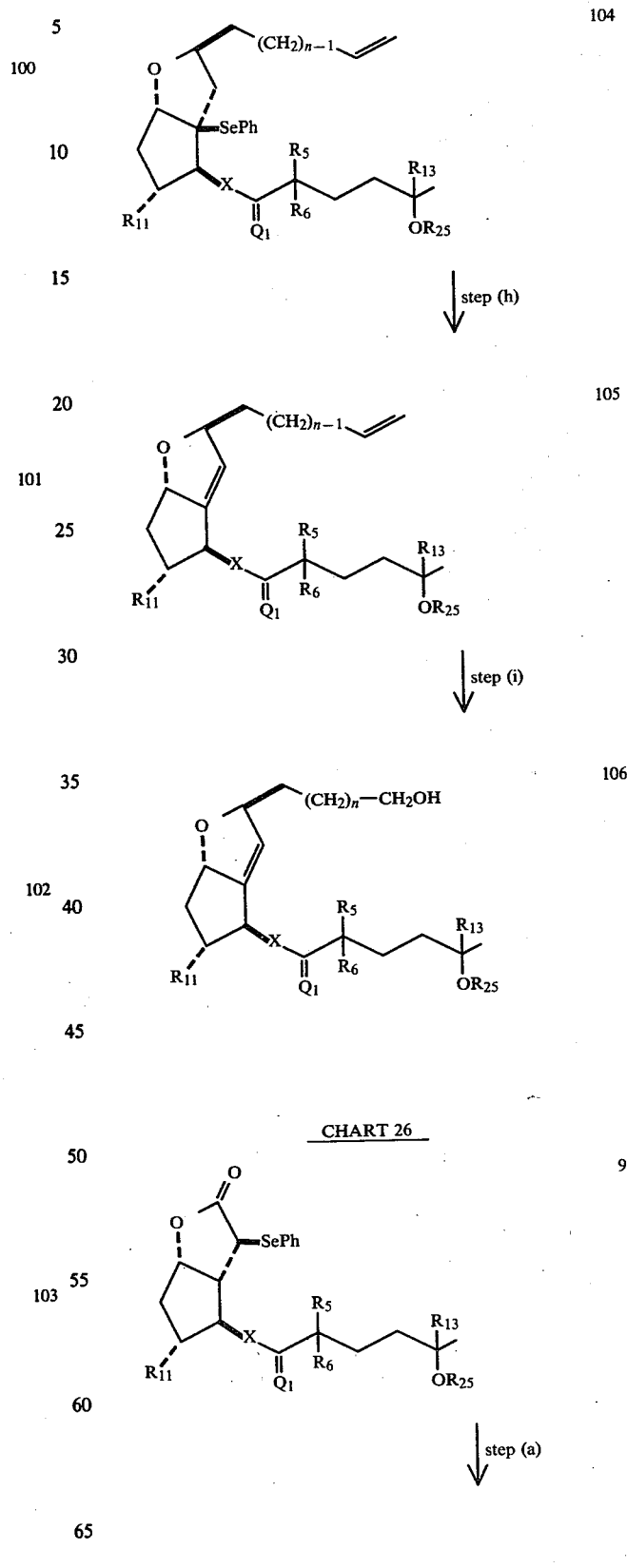
CHART 26
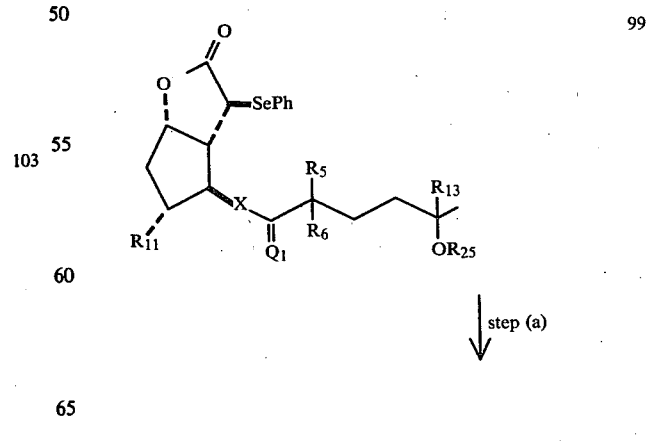

CHART 26
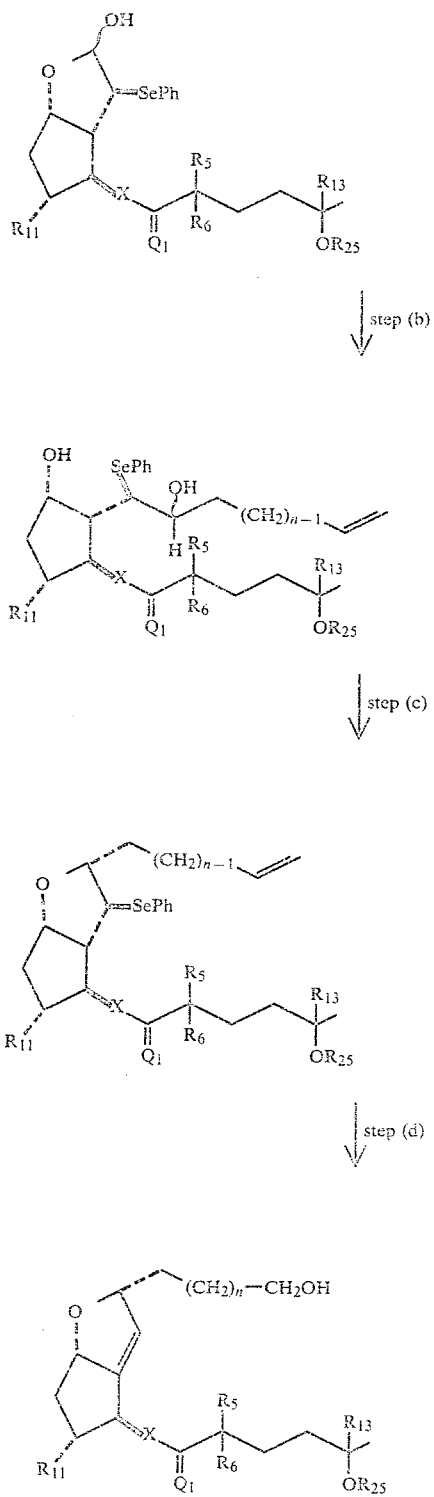
CHART 27
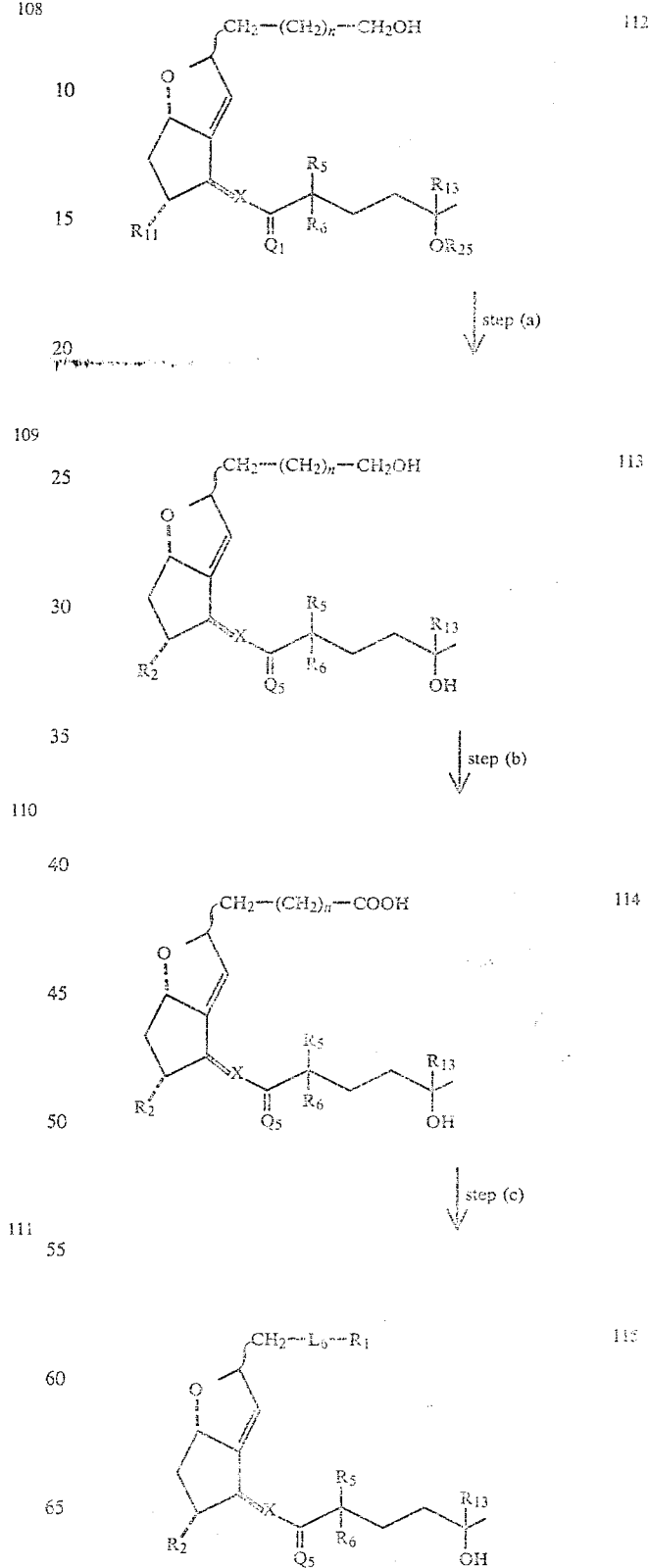

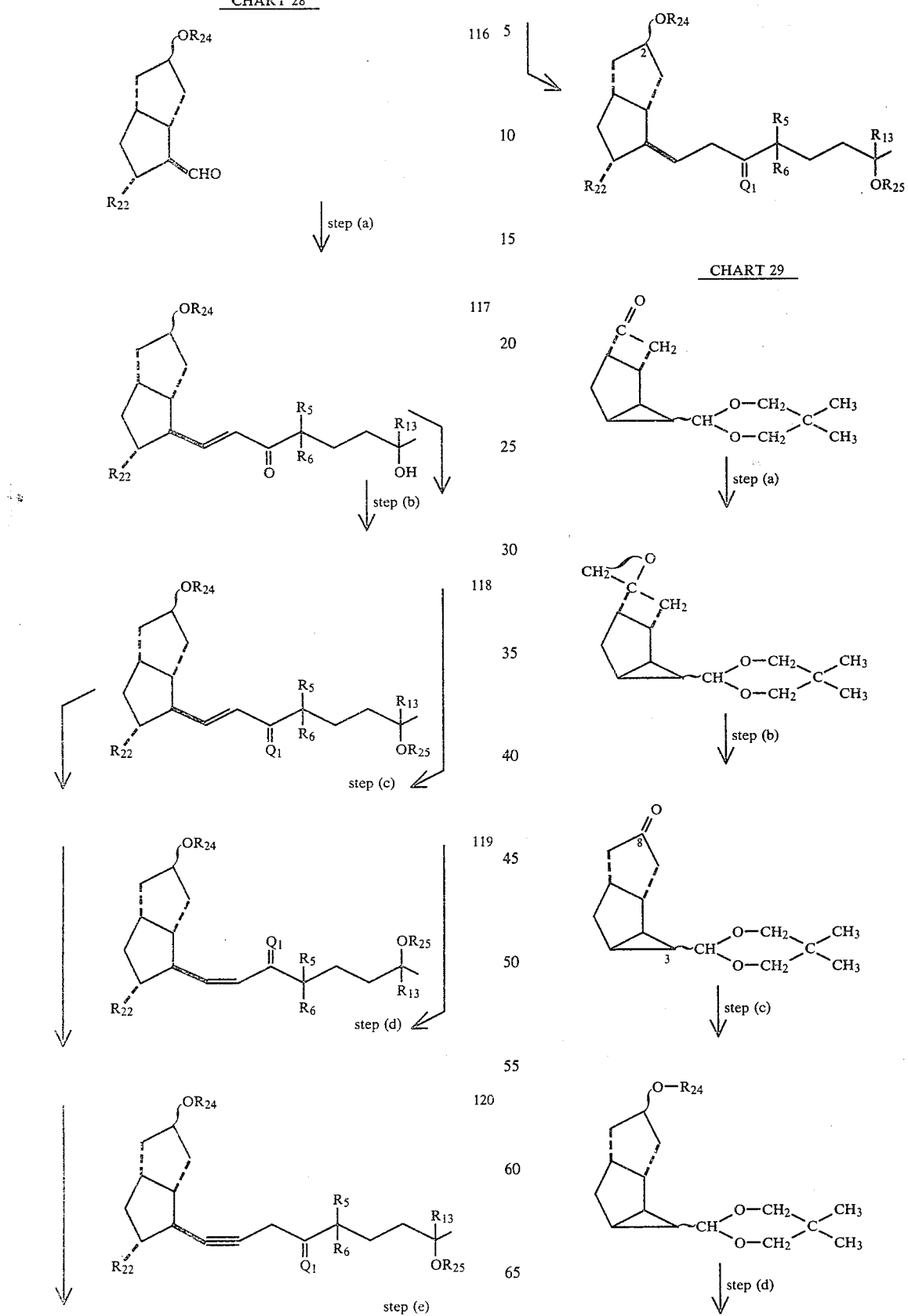

-continued
CHART 29
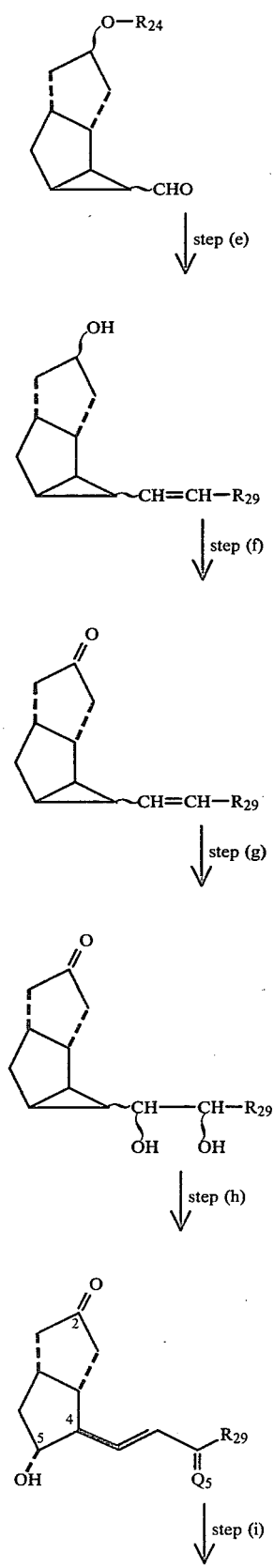
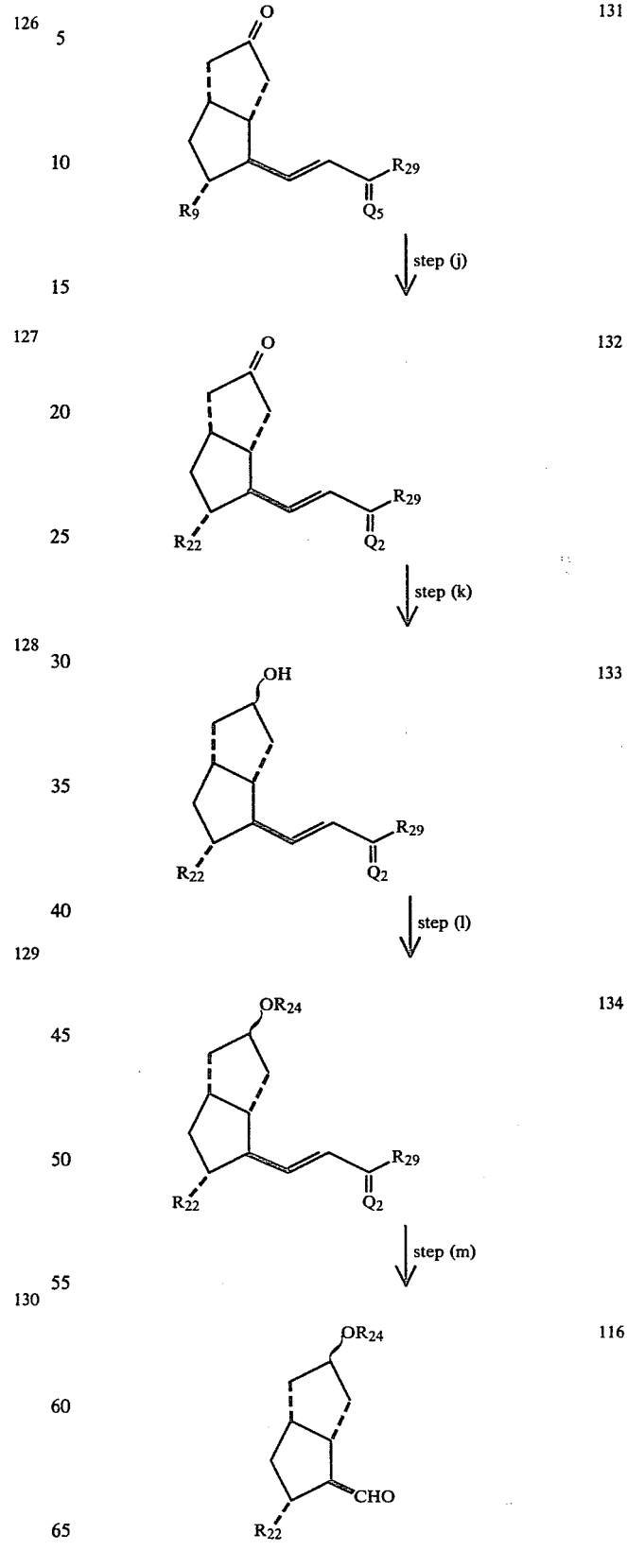

CHART 30
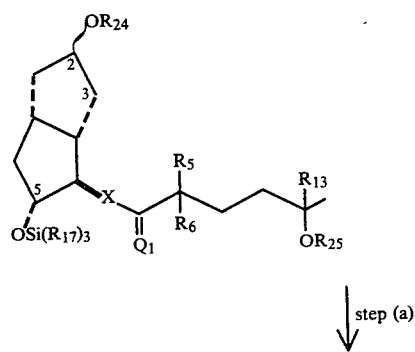
135
↓ step (a)
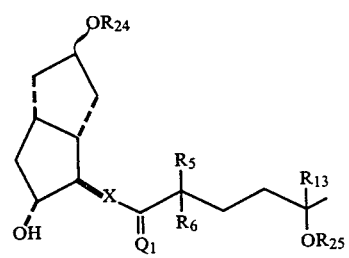
136
↓ step (b)
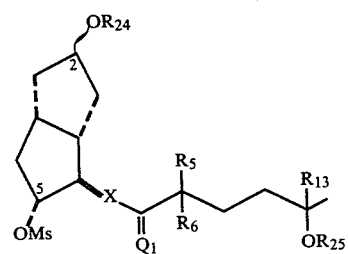
137
↓ step (c)
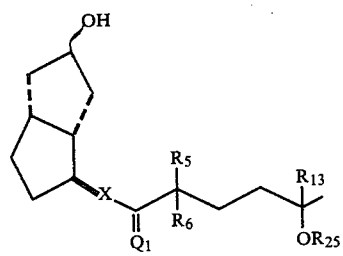
138
↓ step (d)
CHART 30 -continued
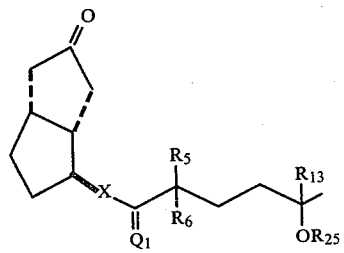
139
↓ step (e)
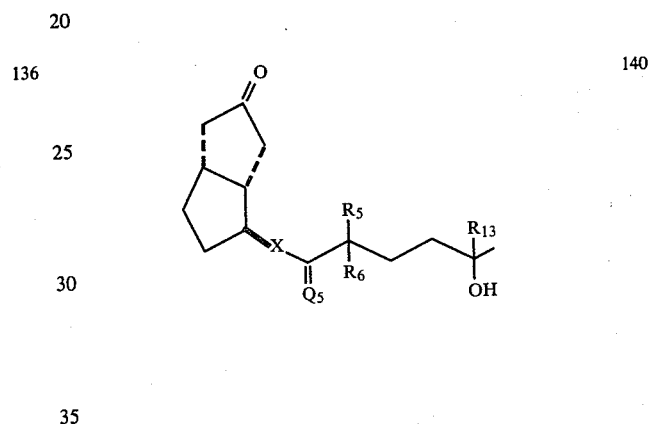
140
CHART 31
141
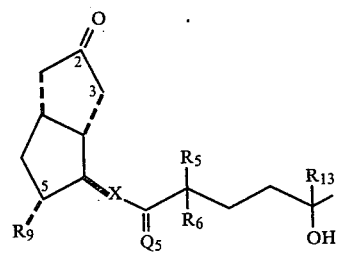
↓ step (a)
142
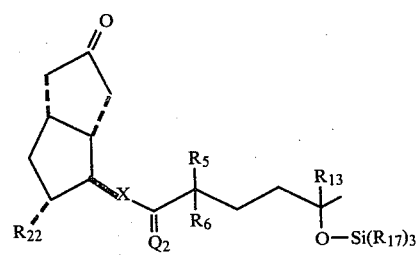
↓ step (b)

CHART 31 -continued
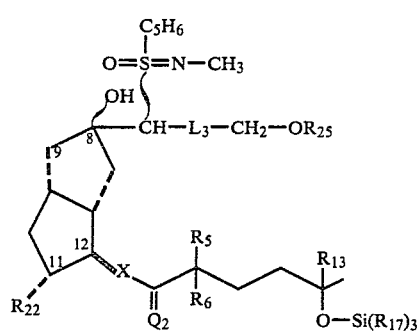 143
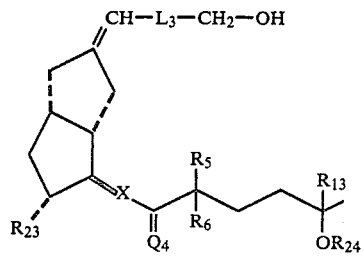 147
step (c)
step (g)
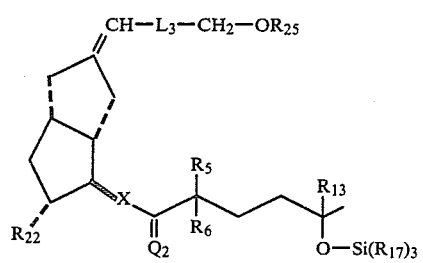 144
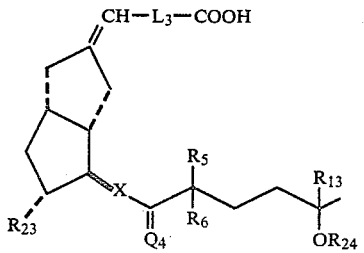 148
step (d)
step (h)
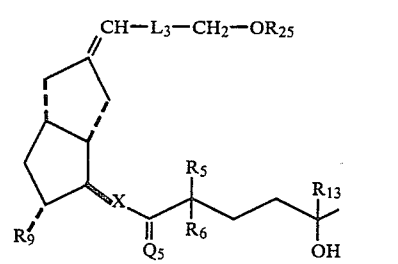 145
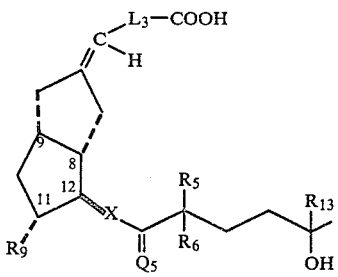 149
step (e)
+
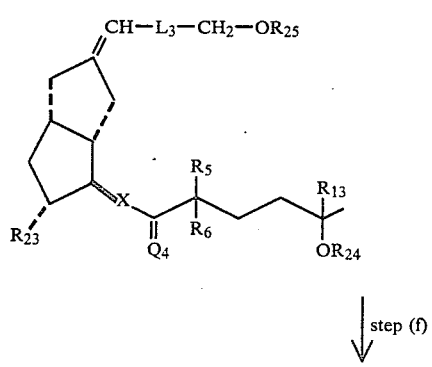 146
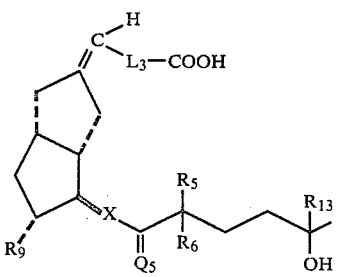 150
step (f)

CHART 32
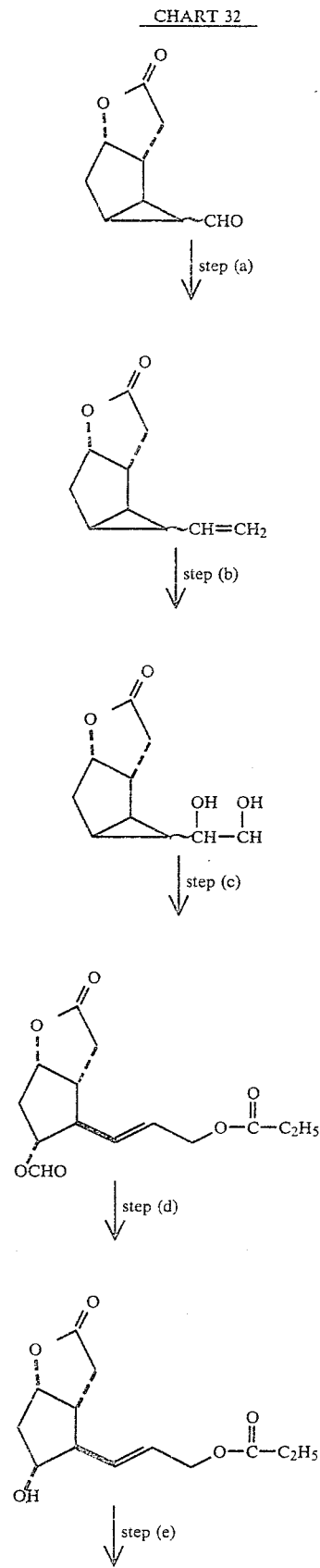
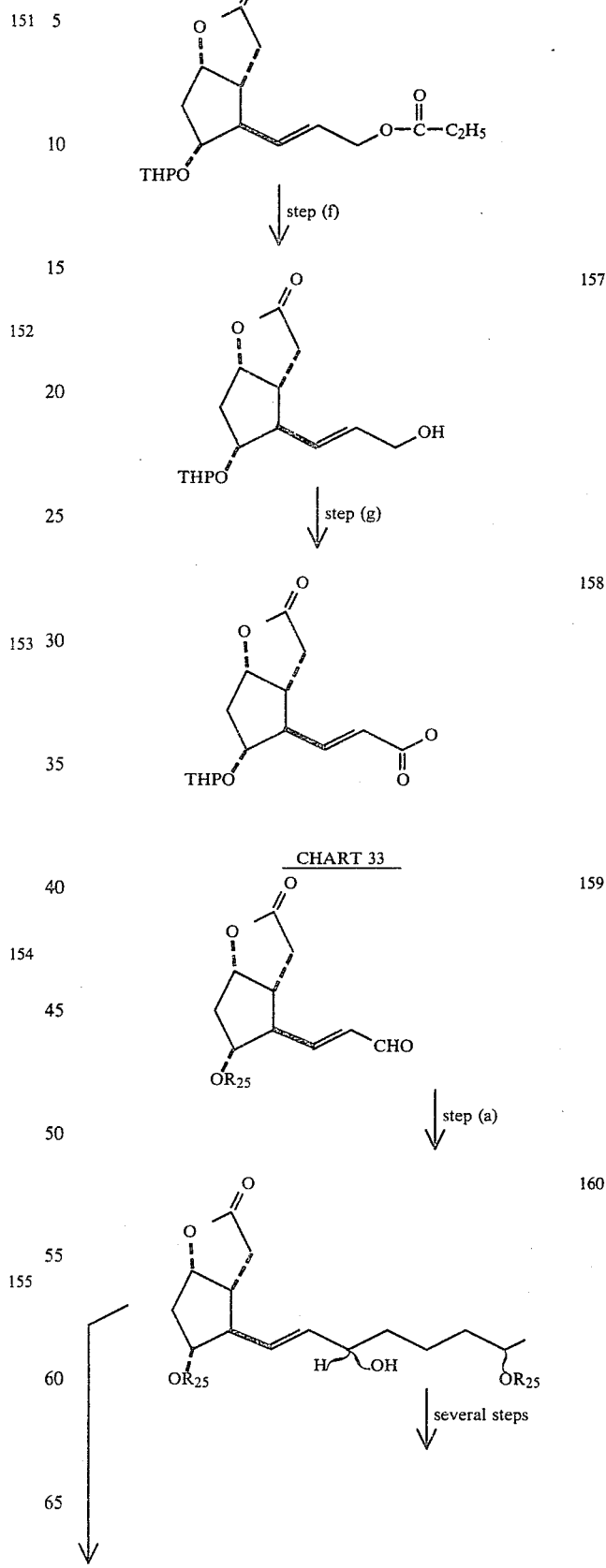
CHART 33

4,225,508
95
-continued
CHART 33
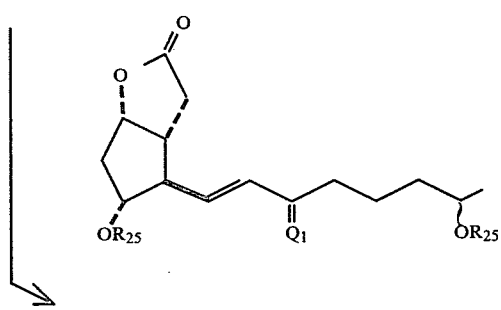
161
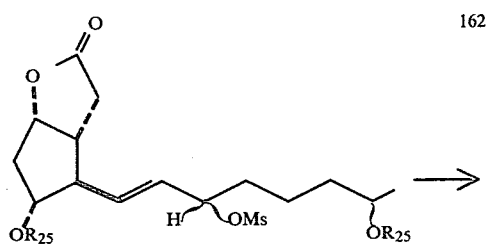
162
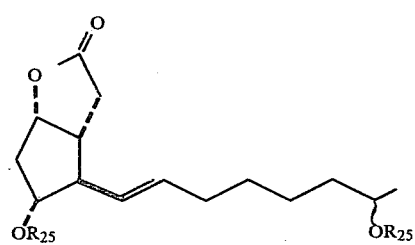
163
CHART 34
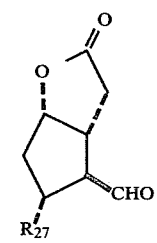
164
step (a)
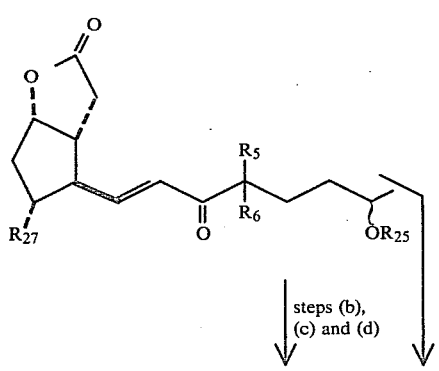
165
steps (b),
(c) and (d)
96
-continued
CHART 34
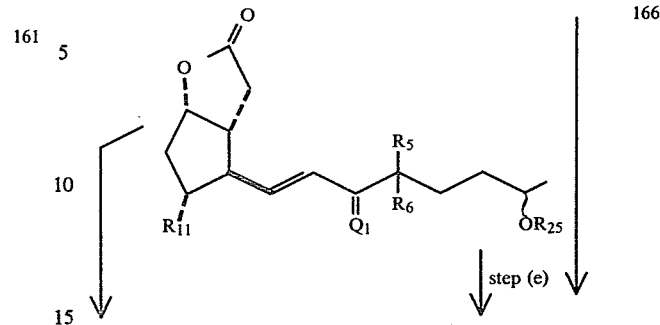
166
step (e)
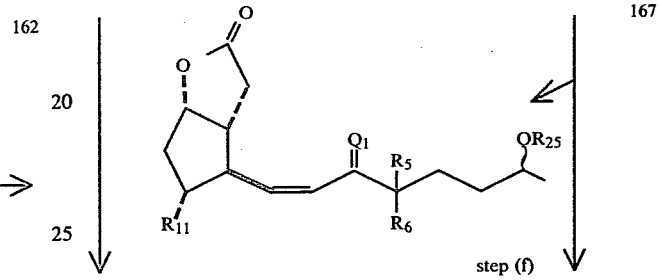
167
step (f)
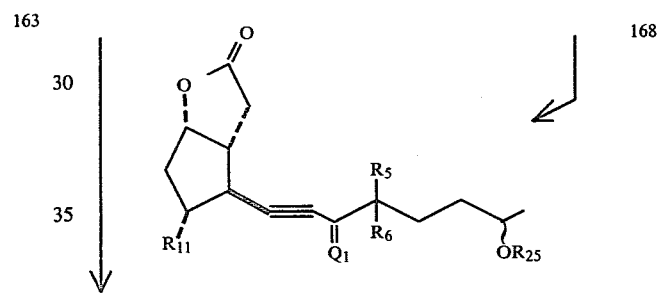
168
step (g)
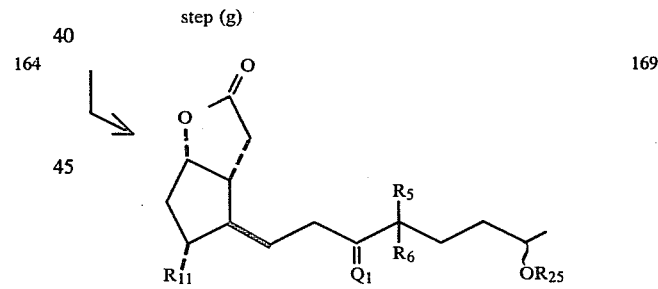
169
CHART 35
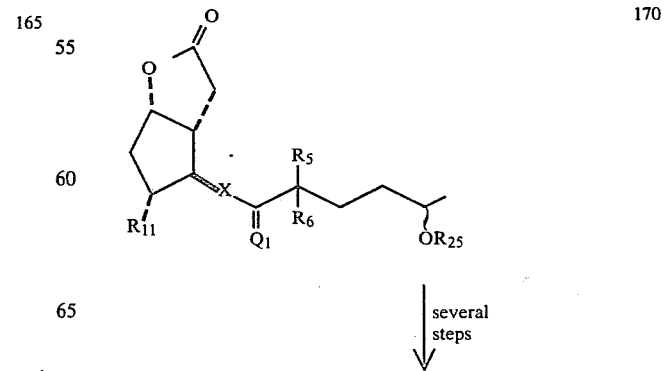
170
several steps -continued
CHART 35
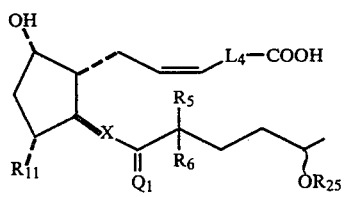
171
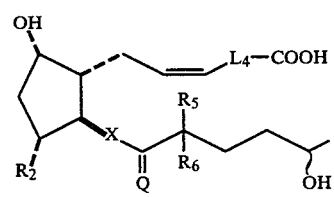
172
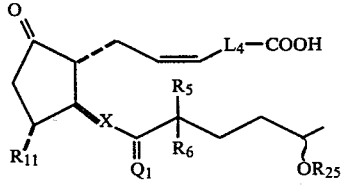
173
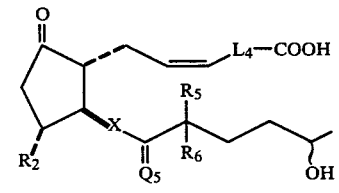
174
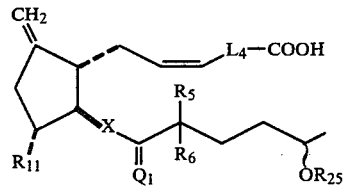
175
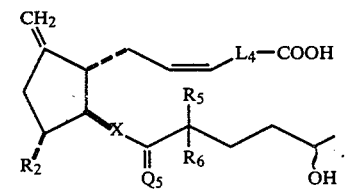
176
CHART 36
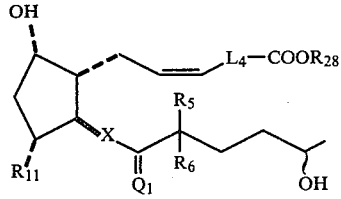
177
↓ step (a)
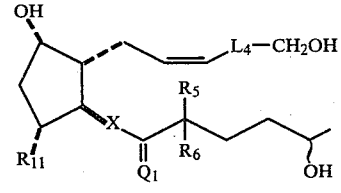
178
↓ step (b)
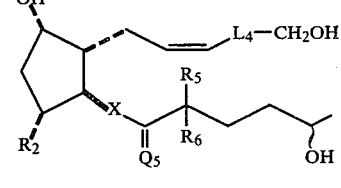
179
step (c)
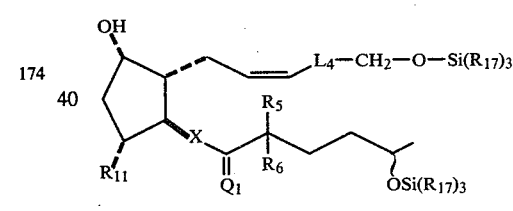
180
↓ step (d)
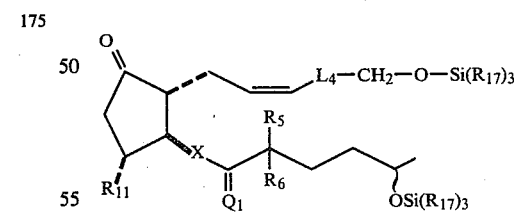
181
↓ step (e)
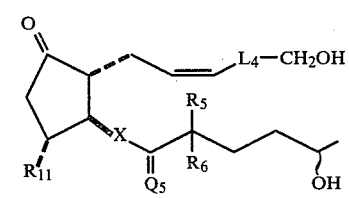
182

CHART 37
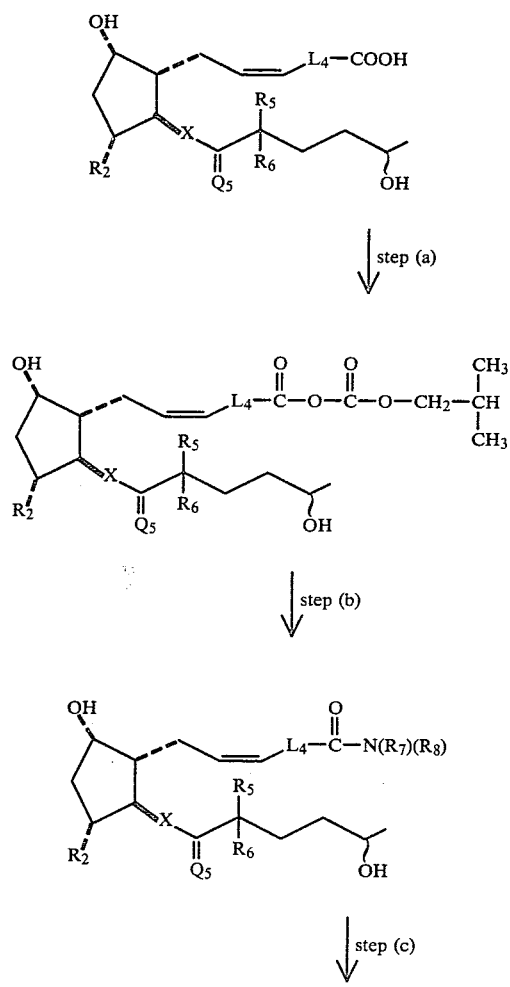
CHART 38
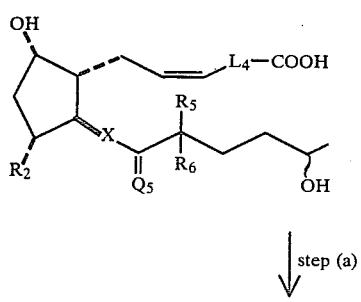
CHART 38 -continued
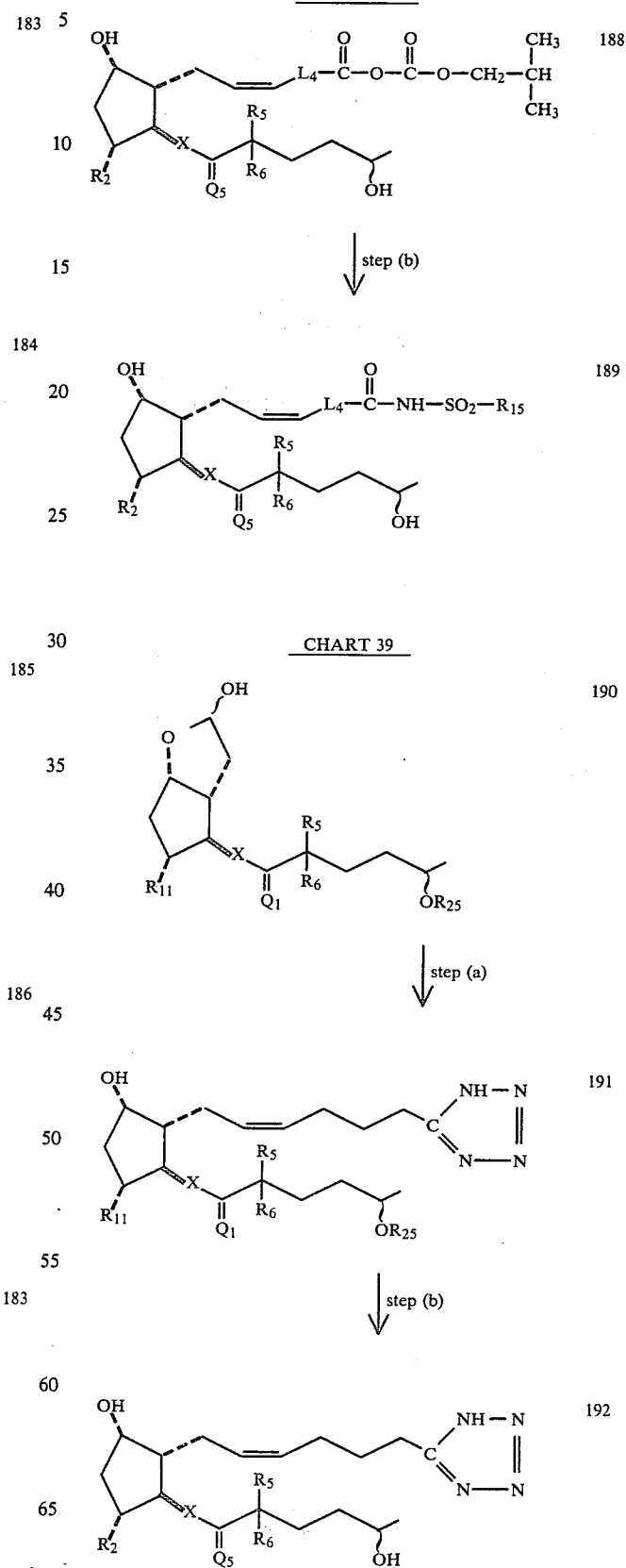

CHART 40
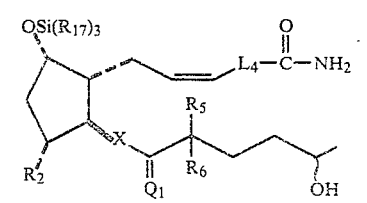  193
↓ step (a)
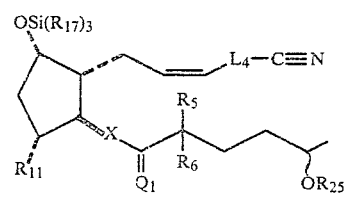  194
↓ step (b)
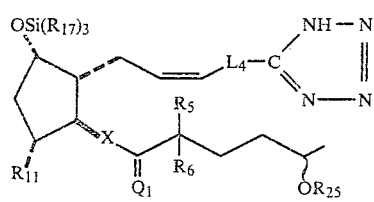  195
↓ step (c)
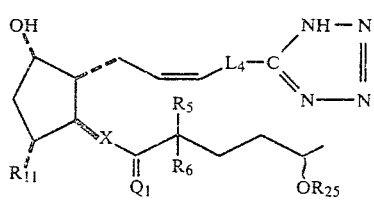  196
↓ step (d)
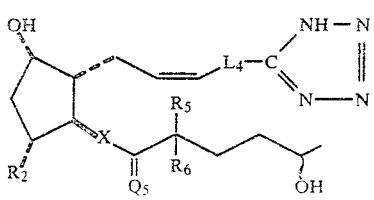  197
CHART 41
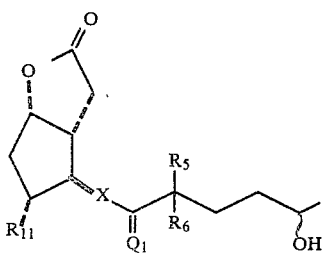  198
↓ step (a)
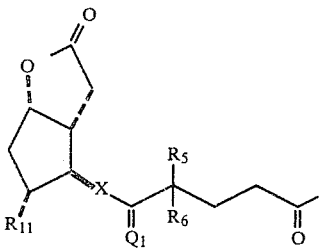  199
↓ step (b)
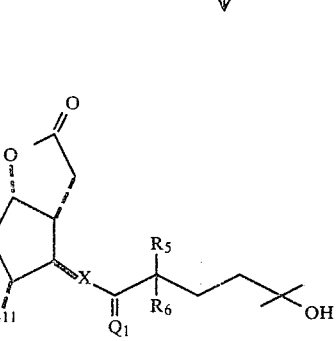  200
↓ step (c)
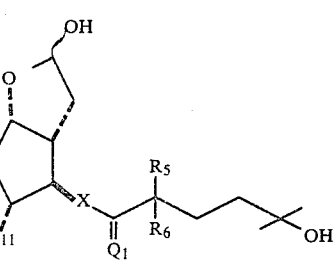  201
↓ step (d)

-continued
CHART 41
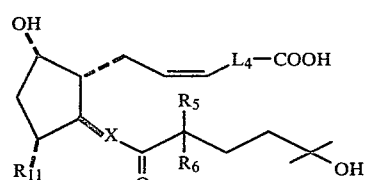 202
↓ step (e)
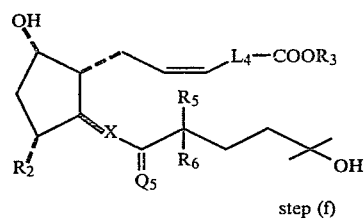 203
↓ step (f)
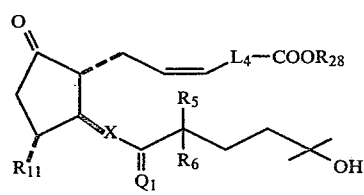 204
↓ step (g)
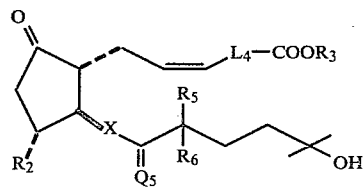 205
CHART 42
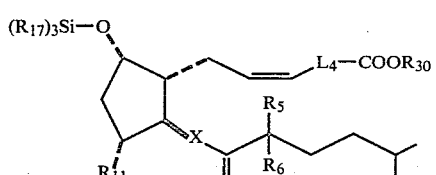 206
↓ step (a)
-continued
CHART 42
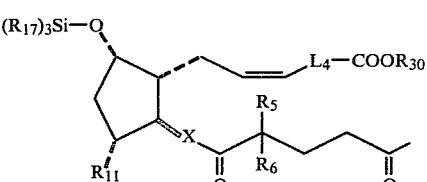 207
↓ step (b)
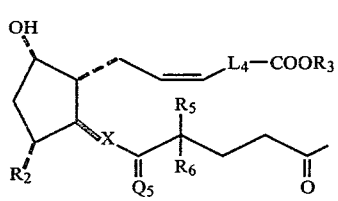 208
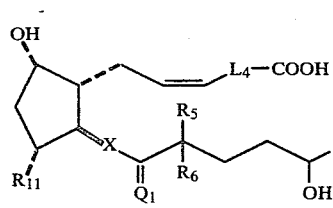 209
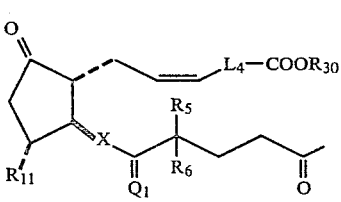 210
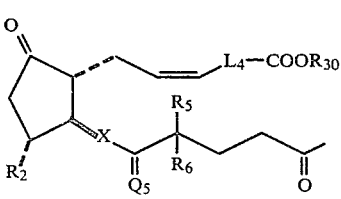 211

CHART 43
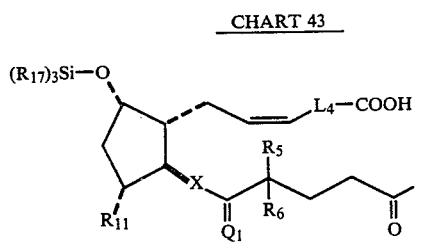
↓ step (a)
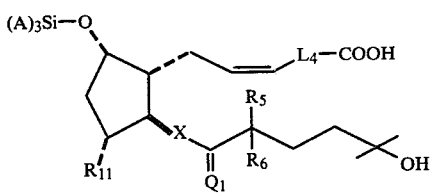
↓ step (b)
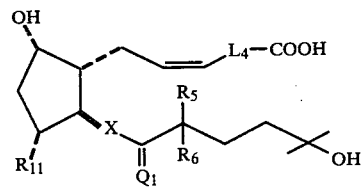
↓ step (c)
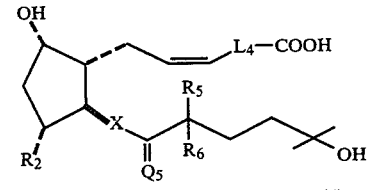
step (d)
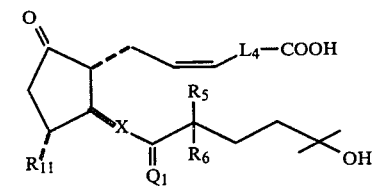
↓ step (e)
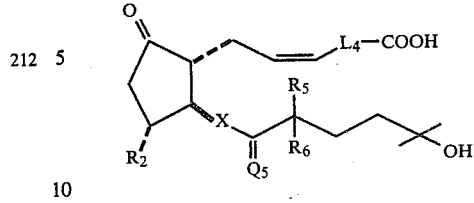
↓
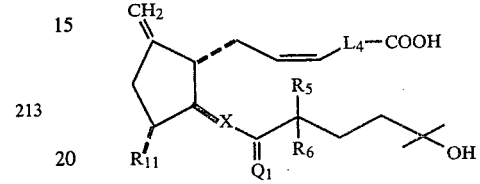
↓ step (f)
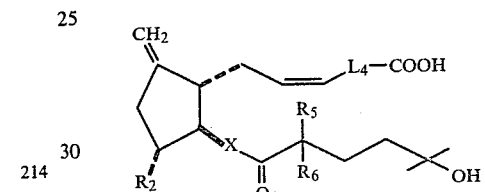
↓ step (g)
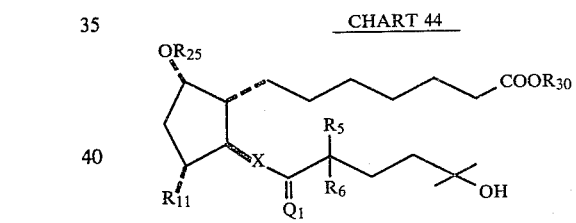
CHART 44
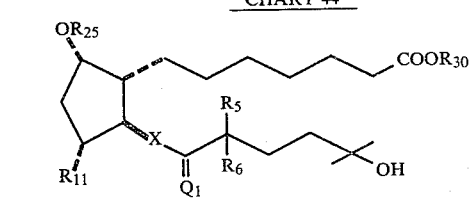
↓ step (a)
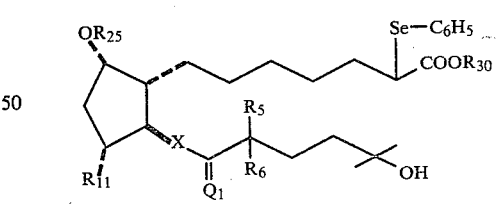
↓ step (b)
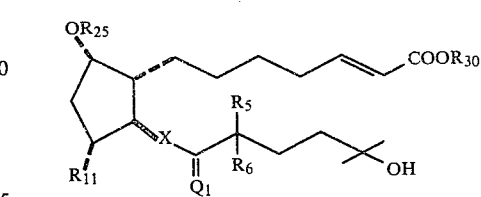
↓ step (c)

-continued
CHART 44

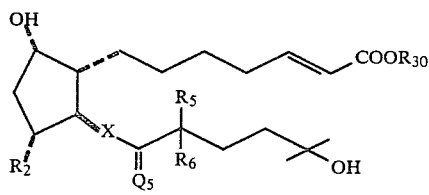

CHART 45

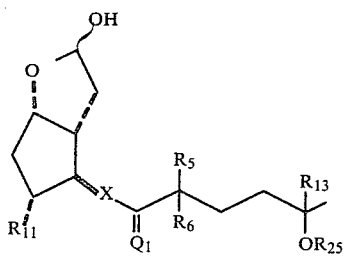

↓ step (a)

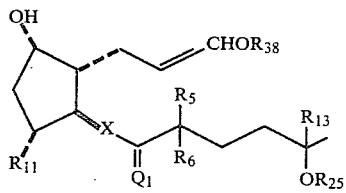

↓ step (b)

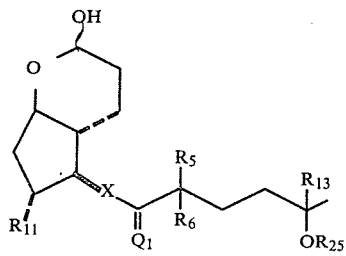

↓ step (c)

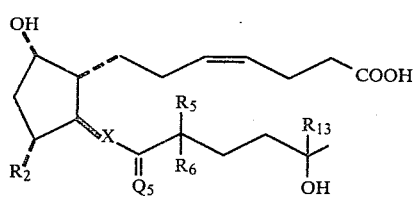

I claim:
1. A prostacyclin-type compound of the formula

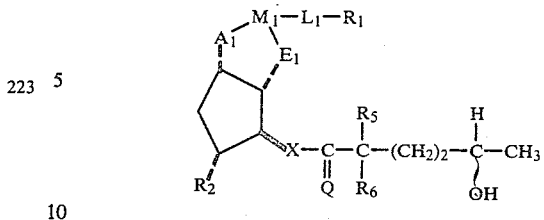

wherein $A_1$ is —O—(oxa) and $E_1$ is —CH$_2$—
wherein $L_1$ is
 (1) —(CH$_2$)$_n$— wherein n is one to 5, inclusor
 (2) —(CH$_2$)$_p$—CF$_2$— wherein P is 2, 3, or 4,
wherein $M_1$ is

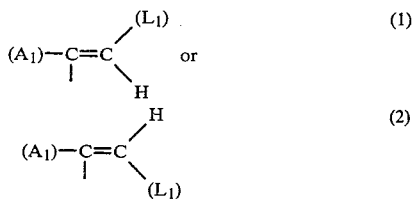

wherein ~ indicates attachment in alpha or beta configuration,
wherein Q is

wherein $R_4$ is hydrogen or alkyl of one to 4 carbon atoms, inclusive,
wherein $R_1$ is
 (1) —COOR$_3$
 (2) —CH$_2$OH
 (3) —CH$_2$N(R$_7$)(R$_8$)

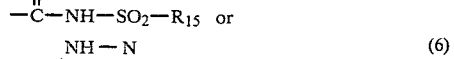

wherein $R_3$ is (a) hydrogen, (b) alkyl of one to 12 carbon atoms, inclusive, (c) cycloalkyl of 3 to 10 carbon atoms, inclusive, (d) aralkyl of 7 to 12 carbon atoms, inclusive, (e) phenyl, (f) phenyl substituted with one, 2, or 3 chloro or alkyl groups of one to 3 carbon atoms, inclusive;

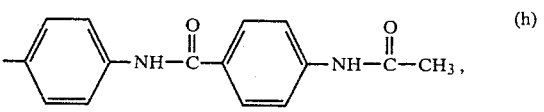

-continued

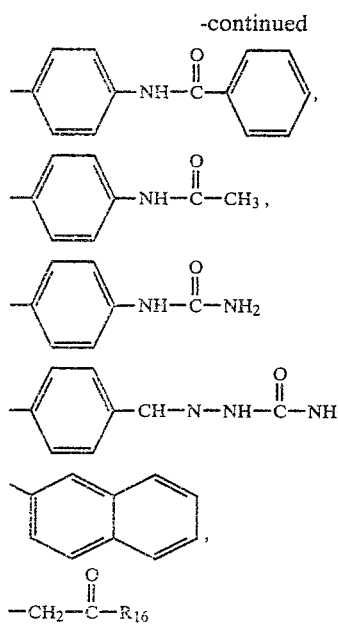

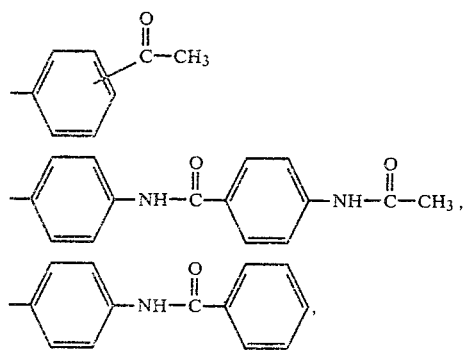

wherein $R_{16}$ is phenyl, p-bromophenyl, p-biphenylyl, p-nitrophenyl, p-benzamidophenyl, or 2-naphthyl, or (o) a pharmacologically acceptable cation; wherein $R_7$ and $R_8$ are hydrogen, alkyl of one to 12 carbon atoms, inclusive, benzyl, or phenyl, being the same or different, and wherein $R_{15}$ is hydrogen, alkyl of one to 12 carbon atoms, inclusive, phenyl, phenyl substituted with one, 2, or 3 chloro or alkyl groups of one to 3 carbon atoms, inclusive, or phenyl substituted with hydroxycarbonyl or alkoxycarbonyl of one to 4 carbon atoms, inclusive, wherein $R_2$ is hydrogen, hydroxyl, or hydroxymethyl, wherein $R_5$ and $R_6$ are hydrogen, alkyl of one to 4 carbon atoms, inclusive, or fluoro, being the same or different, with the proviso that one of $R_5$ and $R_6$ is fluoro only when the other is hydrogen or fluoro, and wherein X is (1) trans-CH=CH—
(2) cis-CH=CH—
(3) -C≡C— or
(4) —CH$_2$CH$_2$—.

2. A compound according to claim 1 wherein $R_1$ is —COOR$_3$ wherein $R_3$ is (a) hydrogen, (b) alkyl of one to 12 carbon atoms, inclusive, (c) cycloalkyl of 3 to 10 carbon atoms, inclusive, (d) aralkyl of 7 to 12 carbon atoms, inclusive, (e) phenyl, (f) phenyl substituted with one, 2, or 3 chloro or alkyl groups of one to 3 carbon atoms, inclusive;

wherein $R_{16}$ is phenyl, p-bromophenyl, p-biphenylyl, p-nitrophenyl, p-benzamidophenyl, or 2-naphthyl, or (o) a pharmacologically acceptable cation.

3. A compound according to claim 2 wherein $M_1$ is

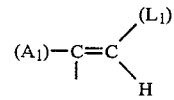

with bonds to $A_1$ and $L_1$ as shown.

4. A compound according to claim 3 wherein $L_1$ is —(CH$_2$)$_3$—, Q is

$R_2$ is hydroxyl, X is trans-CH=CH—, and $R_5$ and $R_6$ are hydrogen.

5. A compound according to claim 4 wherein $R_3$ is hydrogen, alkyl of one to 4 carbon atoms, or a pharmacologically acceptable cation.

6. (5Z)-9-Deoxy-6,9α-epoxy-Δ$^5$-19ξ-hydroxy-PGF$_1$, methyl ester, a compound according to claim 5.

7. (5Z)-9-Deoxy-6,9α-epoxy-Δ$^5$-19ξ-hydroxy-PGF$_1$, sodium salt, a compound according to claim 5.

8. A compound according to claim 1 wherein $R_1$ is —CH$_2$OH.

9. A compound according to claim 8 wherein $M_1$ is

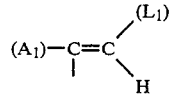

with bonds to $A_1$ and $L_1$ as shown.

10. A compound according to claim 9 wherein $L_1$ is —(CH$_2$)$_3$—, Q is

$R_2$ is hydroxyl, and X is trans-CH=CH—.

11. (5Z)-2-Decarboxy-2-hydroxymethyl-9-deoxy-6,9α-epoxy-Δ$^5$-19ξ-hydroxy-PGF$_1$, a compound according to claim 10.

12. (5Z)-2-Decarboxy-2-hydroxymethyl-9-deoxy-6,9α-epoxy-Δ$^5$-16,16-difluoro-19ξ-hydroxy-PGF$_1$, a compound according to claim 10.

* * * * *

UNITED STATES PATENT OFFICE
CERTIFICATE OF CORRECTION

Patent No. 4,225,508      Dated 30 September 1980

Inventor(s) John C. Sih

It is certified that error appears in the above-identified patent and that said Letters Patent are hereby corrected as shown below:

Column 15, line 38, "$R_{37})_4NO_2$" should read -- $(R_{37})_4NO_2$ --; line 41, "1,5-diazabicyclo[4.3.9]nonene-5" should read -- 1,5-diazabicyclo[4.3.0]-nonene-5 --;

Column 21, line 7, "9 deoxy-6ε,9α-epoxy-" should read -- 9-deoxy-6ξ,9α-epoxy- --; line 13, "-$CH_2CH=CH$-" should read -- -$CH_2$-$CH=CH$- --;

Column 24, line 31, "dehalo-" should read -- dehalogenation. --;

Column 25, line 13, "$R_{31}$-O-1($R_{32}$)-$CHR_{33}R_{34}$" should read -- $R_{31}$-O-C($R_{32}$)-$CHR_{33}R_{34}$ --;

Column 26, line 16, "when X' is -CH-C(Hal)-" should read -- when $X_1$ is -CH=C(Hal)- --; line 17, "yields -C=C-" should read -- yields -C≡C- --;

Column 29, line 35, "$(R_{24})_2o$" should read -- $(R_{24})_2O$ --; line 38, "$((R_{24})_2o)$" should read -- $((R_{24})_2O)$ --;

Column 38, line 29, "5α-hydroxy-2δ-" should read -- 5α-hydroxy-2β- --; line 63, "(step f, 1.8 1 g.)" should read -- (step f, 1.8 g.) --;

Column 39, line 4, "Preparation" should read -- Preparation 2 --;

Column 42, line 26, "5.184.81" should read -- 5.18-4.81 --;

Column 50, line 3, "9-deoxy-5ξ,0α-epoxy-" should read -- 9-deoxy-5ξ,9α-epoxy- --; lines 21-22, "13,14-dihydro-9ξ-hydroxy-" should read -- 13,14-dihydro-19ξ-hydroxy- --;

Column 51, line 11 and 25, "5ξ,9 -dihydroxy-" should read -- 5ξ,19ξ-dihydroxy- --; line 53, "(2E,4E)-9-deoxy-6ν,9α-epoxy-" should read -- (2E,4E)-9-deoxy-6ξ,9α-epoxy- --;

Column 52, line 67, "6ξ,9α-epoxy-66⁶-11-deoxy-" should read -- 6ξ,9α-epoxy-$\Delta^6$-11-deoxy- --;

Column 54, line 6, "19Ξ-hydroxy-" should read -- 19ξ-hydroxy- --; line 58, "19ε-hydroxy-" should read -- 19ξ-hydroxy- --;

Column 55, line 26, "6Ξ,9α-epoxy-" should read -- 6ξ,9α-epoxy- --;

Column 56, line 47, "19Ξ-hydroxy-" should read -- 19ξ-hydroxy- --; line 49, "16,16-difluoro-$PGF_1α$" should read -- 16,16-difluoro-19ξ-hydroxy-$PGF_1α$ --;

UNITED STATES PATENT OFFICE
CERTIFICATE OF CORRECTION

Patent No. 4,225,508    Dated 30 September 1980

Inventor(s) John C. Sih

It is certified that error appears in the above-identified patent and that said Letters Patent are hereby corrected as shown below:

Column 58, lines 6-15, that portion of formula 9 reading

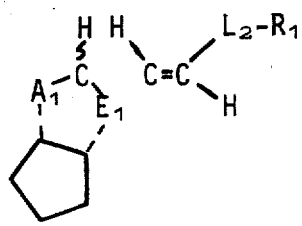    should read    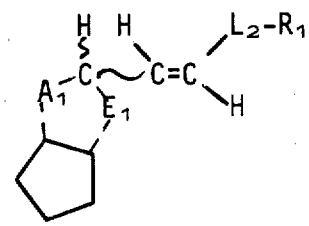

Column 68, lines 57-68, that portion of formula 48 reading should read

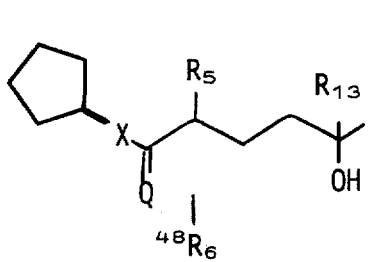    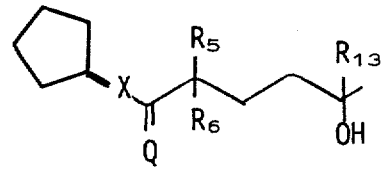

Column 69, lines 14-23, that portion of formula 50 reading

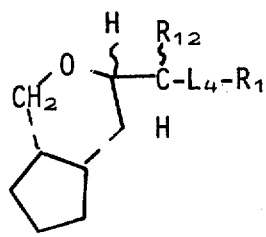    should read    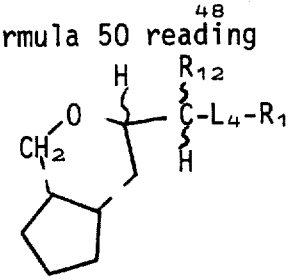

UNITED STATES PATENT OFFICE
CERTIFICATE OF CORRECTION

Patent No. 4,225,508  Dated 30 September 1980

Inventor(s) John C. Sih

It is certified that error appears in the above-identified patent and that said Letters Patent are hereby corrected as shown below:

Column 77, lines 28-52, that portion of formulas 85 and 86 reading

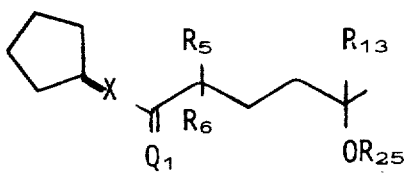   should read   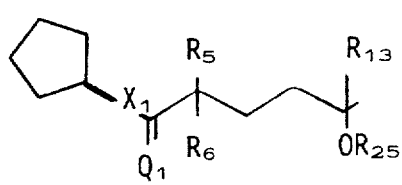

Column 94, lines 27-35, that portion of formula 158 reading

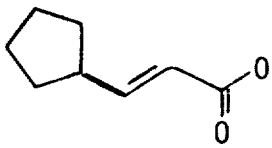   should read   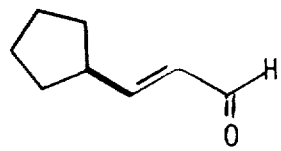

Signed and Sealed this

Twenty-sixth Day of October 1982

[SEAL]

Attest:

GERALD J. MOSSINGHOFF

Attesting Officer   Commissioner of Patents and Trademarks